(12) United States Patent
Atkins et al.

(10) Patent No.: US 11,911,557 B2
(45) Date of Patent: Feb. 27, 2024

(54) HEATING ELEMENT

(71) Applicant: JUUL Labs, Inc., San Francisco, CA (US)

(72) Inventors: Ariel Atkins, San Francisco, CA (US); Christopher L. Belisle, Somerset, WI (US); Steven Christensen, Burlingame, CA (US); Alexander M. Hoopai, San Francisco, CA (US); Eric Joseph Johnson, San Francisco, CA (US); Jason King, San Francisco, CA (US); Esteban Leon Duque, Berkeley, CA (US); Christopher James Rosser, Cambridge (GB)

(73) Assignee: JUUL Labs, Inc., San Francisco, CA (US)

( * ) Notice: Subject to any disclaimer, the term of this patent is extended or adjusted under 35 U.S.C. 154(b) by 276 days.

(21) Appl. No.: 17/161,590

(22) Filed: Jan. 28, 2021

(65) Prior Publication Data

US 2021/0220576 A1    Jul. 22, 2021

Related U.S. Application Data

(63) Continuation of application No. 16/653,455, filed on Oct. 15, 2019, now Pat. No. 10,905,835.
(Continued)

(51) Int. Cl.
*A61M 11/04* (2006.01)
*A24F 40/46* (2020.01)
*H05B 3/44* (2006.01)

(52) U.S. Cl.
CPC ........... *A61M 11/042* (2014.02); *A24F 40/46* (2020.01); *H05B 3/44* (2013.01); *H05B 2203/021* (2013.01)

(58) Field of Classification Search
CPC .. H05B 3/44; H05B 2203/021; A61M 11/042; A24F 40/46
See application file for complete search history.

(56) References Cited

U.S. PATENT DOCUMENTS

| 3,271,719 A | 9/1966 | Ovshinsky |
|---|---|---|
| 6,084,616 A | 7/2000 | Nakata et al. |

(Continued)

FOREIGN PATENT DOCUMENTS

| CN | 202873795 U | 4/2013 |
|---|---|---|
| CN | 302396126 | 4/2013 |

(Continued)

OTHER PUBLICATIONS

U.S. Appl. No. 16/653,455, filed Oct. 15, 2019, now U.S. Pat. No. 10,905,835.
(Continued)

*Primary Examiner* — Brian W Jennison
(74) *Attorney, Agent, or Firm* — Mintz Levin Cohn Ferris Glovsky and Popeo, P.C.

(57) ABSTRACT

A heating element for a vaporizer cartridge is provided. The vaporizer cartridge may include a reservoir containing vaporizable material and a wicking element in fluid communication with the reservoir. The heating element may include a heating portion, a cartridge contact, and a leg. The heating portion includes at least two tines spaced apart from one another. The cartridge contact may be in in electrical communication with a power source. The leg extends between the heating portion and the cartridge contact. The heating portion may be crimped around the wicking element such that the heating portion secures the wicking element to the heating element and contacts at least two surfaces of the wicking element.

18 Claims, 48 Drawing Sheets

Related U.S. Application Data

(60) Provisional application No. 62/913,135, filed on Oct. 9, 2019, provisional application No. 62/812,161, filed on Feb. 28, 2019, provisional application No. 62/747,099, filed on Oct. 17, 2018, provisional application No. 62/745,589, filed on Oct. 15, 2018.

(56) References Cited

U.S. PATENT DOCUMENTS

| | | |
|---|---|---|
| 6,155,268 A | 12/2000 | Takeuchi |
| 6,708,846 B1 | 3/2004 | Fuchs et al. |
| 8,528,569 B1 | 9/2013 | Newton |
| 8,752,545 B2 | 6/2014 | Buchberger |
| 9,146,246 B2 | 9/2015 | Battrell et al. |
| 9,427,022 B2 | 8/2016 | Levin et al. |
| 9,498,588 B2 | 11/2016 | Benassayag et al. |
| 9,549,573 B2 | 1/2017 | Monsees et al. |
| 9,609,893 B2 | 4/2017 | Novak, III et al. |
| 9,723,877 B2 | 8/2017 | Wong et al. |
| 9,781,953 B2 | 10/2017 | Verleur et al. |
| 9,986,761 B2 | 6/2018 | Thorens et al. |
| 10,045,568 B2 | 8/2018 | Monsees et al. |
| 10,085,481 B2 | 10/2018 | Verleur et al. |
| 10,104,915 B2 | 10/2018 | Bowen et al. |
| 10,130,123 B2 | 11/2018 | Hatton et al. |
| 10,159,282 B2 | 12/2018 | Monsees et al. |
| 2002/0186283 A1 | 12/2002 | Smith et al. |
| 2003/0215335 A1 | 11/2003 | Crivelli |
| 2004/0050382 A1 | 3/2004 | Goodchild |
| 2006/0047368 A1 | 3/2006 | Maharajh et al. |
| 2007/0277816 A1 | 12/2007 | Morrison et al. |
| 2009/0230117 A1 | 9/2009 | Fernando et al. |
| 2010/0253281 A1 | 10/2010 | Li |
| 2011/0155153 A1 | 6/2011 | Thorens et al. |
| 2011/0226236 A1 | 9/2011 | Buchberger |
| 2013/0042865 A1 | 2/2013 | Monsees et al. |
| 2013/0104916 A1 | 5/2013 | Bellinger et al. |
| 2013/0192615 A1 | 8/2013 | Tucker et al. |
| 2013/0228190 A1 | 9/2013 | Weiss et al. |
| 2013/0255675 A1 | 10/2013 | Liu |
| 2013/0284192 A1 | 10/2013 | Peleg et al. |
| 2013/0306064 A1 | 11/2013 | Thorens et al. |
| 2014/0007891 A1 | 1/2014 | Liu |
| 2014/0144429 A1 | 5/2014 | Wensley et al. |
| 2014/0144453 A1 | 5/2014 | Capuano et al. |
| 2014/0190496 A1 | 7/2014 | Wensley et al. |
| 2014/0202454 A1 | 7/2014 | Buchberger |
| 2014/0216483 A1 | 8/2014 | Alima |
| 2014/0224244 A1 | 8/2014 | Liu |
| 2014/0261408 A1 | 9/2014 | DePiano et al. |
| 2014/0261495 A1 | 9/2014 | Novak, III et al. |
| 2014/0270729 A1 | 9/2014 | DePiano et al. |
| 2014/0270730 A1 | 9/2014 | DePiano et al. |
| 2014/0299125 A1 | 10/2014 | Buchberger |
| 2014/0305454 A1 | 10/2014 | Rinker et al. |
| 2014/0332020 A1 | 11/2014 | Li et al. |
| 2014/0332022 A1 | 11/2014 | Li et al. |
| 2014/0363145 A1 | 12/2014 | Plojoux et al. |
| 2014/0366898 A1 | 12/2014 | Monsees et al. |
| 2014/0376895 A1 | 12/2014 | Han |
| 2015/0013696 A1 | 1/2015 | Plojoux et al. |
| 2015/0027457 A1 | 1/2015 | Janardhan et al. |
| 2015/0027460 A1 | 1/2015 | Liu |
| 2015/0027471 A1 | 1/2015 | Feldman et al. |
| 2015/0034104 A1 | 2/2015 | Zhou |
| 2015/0083147 A1 | 3/2015 | Schiff et al. |
| 2015/0101606 A1 | 4/2015 | White |
| 2015/0101626 A1 | 4/2015 | Li et al. |
| 2015/0136158 A1 | 5/2015 | Stevens et al. |
| 2015/0157055 A1 | 6/2015 | Lord |
| 2015/0164147 A1 | 6/2015 | Verleur et al. |
| 2015/0181944 A1 | 7/2015 | Li et al. |
| 2015/0189919 A1 | 7/2015 | Liu |
| 2015/0196060 A1 | 7/2015 | Wensley et al. |
| 2015/0208729 A1 | 7/2015 | Monsees et al. |
| 2015/0216237 A1 | 8/2015 | Wensley et al. |
| 2015/0217068 A1 | 8/2015 | Wakalopulos |
| 2015/0237916 A1 | 8/2015 | Farine et al. |
| 2015/0245669 A1 | 9/2015 | Cadieux et al. |
| 2015/0264979 A1 | 9/2015 | Thorens et al. |
| 2015/0305408 A1 | 10/2015 | Liu |
| 2015/0327595 A1 | 11/2015 | Scatterday |
| 2015/0327596 A1 | 11/2015 | Alarcon et al. |
| 2015/0327597 A1 | 11/2015 | Li et al. |
| 2015/0335071 A1 | 11/2015 | Brinkley et al. |
| 2015/0357839 A1 | 12/2015 | Cai et al. |
| 2016/0007651 A1 | 1/2016 | Ampolini et al. |
| 2016/0021933 A1 | 1/2016 | Thorens et al. |
| 2016/0057811 A1 | 2/2016 | Alarcon et al. |
| 2016/0157523 A1 | 6/2016 | Liu |
| 2016/0198767 A1 | 7/2016 | Verleur |
| 2016/0198768 A1 | 7/2016 | Liu |
| 2016/0219934 A1 | 8/2016 | Li et al. |
| 2016/0270442 A1 | 9/2016 | Liu |
| 2016/0309786 A1 | 10/2016 | Holtz et al. |
| 2016/0331035 A1 | 11/2016 | Cameron |
| 2016/0341419 A1 | 11/2016 | Fluhrer |
| 2016/0366725 A1 | 12/2016 | Tucker et al. |
| 2016/0374393 A1 | 12/2016 | Chen |
| 2017/0043106 A1 | 2/2017 | Hyland et al. |
| 2017/0043910 A1 | 2/2017 | Hopps et al. |
| 2017/0056883 A1 | 3/2017 | Aarts et al. |
| 2017/0135399 A1 | 5/2017 | Gavrielov et al. |
| 2017/0163046 A1 | 6/2017 | Patil et al. |
| 2017/0196263 A1 | 7/2017 | Sur |
| 2017/0224021 A1 | 8/2017 | Xiang et al. |
| 2017/0231276 A1 | 8/2017 | Mironov et al. |
| 2017/0258134 A1 | 9/2017 | Kane |
| 2017/0259170 A1 | 9/2017 | Bowen et al. |
| 2017/0280779 A1 | 10/2017 | Qiu |
| 2017/0367402 A1 | 12/2017 | Lau et al. |
| 2018/0020736 A1 | 1/2018 | Silvestrini et al. |
| 2018/0027877 A1 | 2/2018 | Tucker et al. |
| 2018/0027879 A1 | 2/2018 | Gavrielov et al. |
| 2018/0077967 A1 | 3/2018 | Hatton et al. |
| 2018/0116292 A1 | 5/2018 | Atkins et al. |
| 2018/0125120 A1 | 5/2018 | Gavrielov et al. |
| 2018/0132536 A1 | 5/2018 | Henry, Jr. |
| 2018/0146711 A1 | 5/2018 | Mazur et al. |
| 2018/0199627 A1 | 7/2018 | Bowen et al. |
| 2018/0220707 A1 | 8/2018 | Biel et al. |
| 2018/0279682 A1 | 10/2018 | Guo et al. |
| 2018/0279685 A1 | 10/2018 | Thorens et al. |
| 2018/0280637 A1 | 10/2018 | Mayle et al. |
| 2018/0297047 A1 | 10/2018 | Tong |
| 2019/0099561 A1 | 4/2019 | Nettenstrom |
| 2019/0104764 A1 | 4/2019 | Tucker et al. |
| 2019/0166913 A1 | 6/2019 | Trzecieski |
| 2019/0246693 A1* | 8/2019 | Nettenstrom ............ F16J 15/10 |
| 2019/0373953 A1 | 12/2019 | Atkins et al. |
| 2020/0022417 A1 | 1/2020 | Atkins et al. |
| 2020/0046033 A1 | 2/2020 | Robert et al. |
| 2020/0107585 A1 | 4/2020 | Atkins et al. |
| 2020/0114094 A1 | 4/2020 | Atkins et al. |
| 2020/0128874 A1 | 4/2020 | Atkins et al. |
| 2020/0205474 A1 | 7/2020 | Tong |

FOREIGN PATENT DOCUMENTS

| | | |
|---|---|---|
| CN | 103859604 A | 6/2014 |
| CN | 104738816 A | 7/2015 |
| CN | 105011375 A | 11/2015 |
| CN | 207011686 U | 2/2018 |
| CN | 108158039 A | 6/2018 |
| CN | 108158044 A | 6/2018 |
| CN | 109259313 A | 1/2019 |
| CN | 109588779 A | 4/2019 |
| CN | 110226778 A | 9/2019 |
| EP | 2404515 A1 | 1/2012 |
| EP | 2888964 A1 | 7/2015 |
| EP | 2944207 A1 | 11/2015 |
| EP | 3170414 A1 | 5/2017 |
| EP | 3220987 A1 | 9/2017 |
| EP | 3337341 A1 | 6/2018 |

(56) References Cited

FOREIGN PATENT DOCUMENTS

| | | |
|---|---|---|
| EP | 3488715 A2 | 5/2019 |
| EP | 3694357 A1 | 8/2020 |
| EP | 3863436 A1 | 8/2021 |
| EP | 3664630 B1 | 2/2022 |
| GB | 2548647 A | 9/2017 |
| JP | 2013/113551 A | 6/2013 |
| JP | 2015-198985 A | 11/2015 |
| JP | 2018-509158 A | 4/2018 |
| JP | 2018-523976 A | 8/2018 |
| KR | 20130107658 A | 10/2013 |
| KR | 1020180088806 A | 8/2017 |
| RU | 2527351 C2 | 8/2014 |
| RU | 2611487 C2 | 2/2017 |
| RU | 2656089 C2 | 5/2018 |
| WO | WO-2011147691 A1 | 12/2011 |
| WO | WO-2013060781 A1 | 5/2013 |
| WO | WO-2013113173 A1 | 8/2013 |
| WO | WO-2014150979 A2 | 9/2014 |
| WO | WO-2015077645 A1 | 5/2015 |
| WO | WO-2016023809 A1 | 2/2016 |
| WO | WO-2016/079155 A1 | 5/2016 |
| WO | WO-2016123763 A1 | 8/2016 |
| WO | WO-2016145072 A1 | 9/2016 |
| WO | WO-2017093535 A1 | 6/2017 |
| WO | WO-2017139595 A1 | 8/2017 |
| WO | WO-2017163050 A1 | 9/2017 |
| WO | WO-2017163052 A1 | 9/2017 |
| WO | WO-2018024742 A1 | 2/2018 |
| WO | WO-2018/122380 A1 | 7/2018 |
| WO | WO-2018172765 A1 | 9/2018 |
| WO | WO-2018202403 A1 | 11/2018 |
| WO | WO-2019073010 A1 | 4/2019 |
| WO | WO-2020025644 A1 | 2/2020 |

OTHER PUBLICATIONS

U.S. Appl. No. 16/657,857, filed Oct. 18, 2019, US 2020-0120991.
U.S. Appl. No. 16/656,360, filed Oct. 17, 2019, US 2020-0128874.
U.S. Appl. No. 16/805,672, filed Feb. 28, 2020, US 2020-0275696.

* cited by examiner

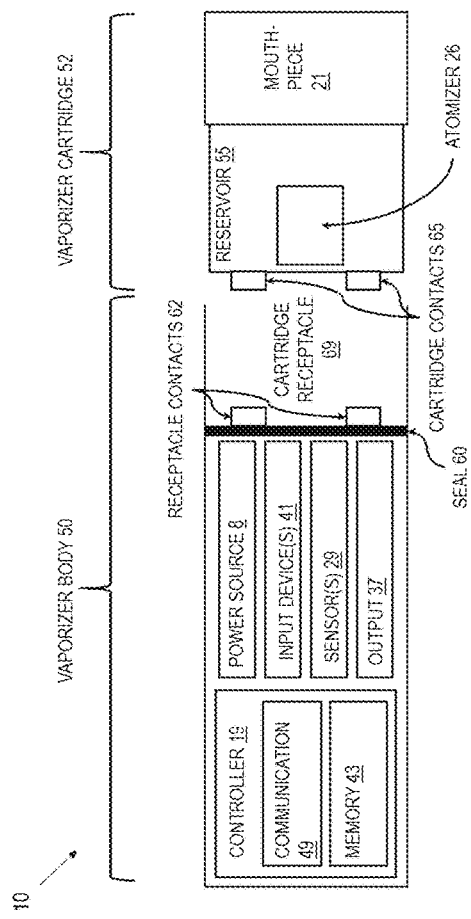
FIG. 1A
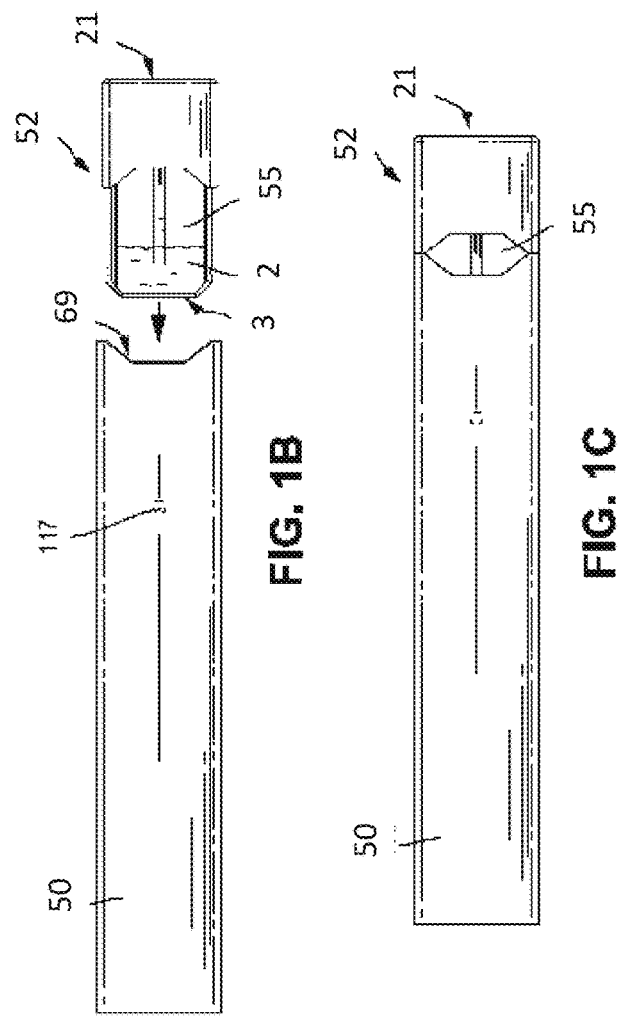
FIG. 1B
FIG. 1C

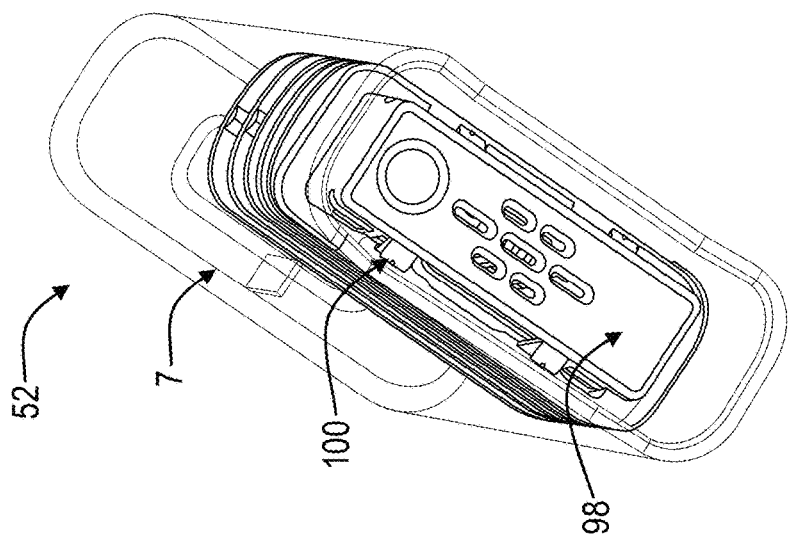
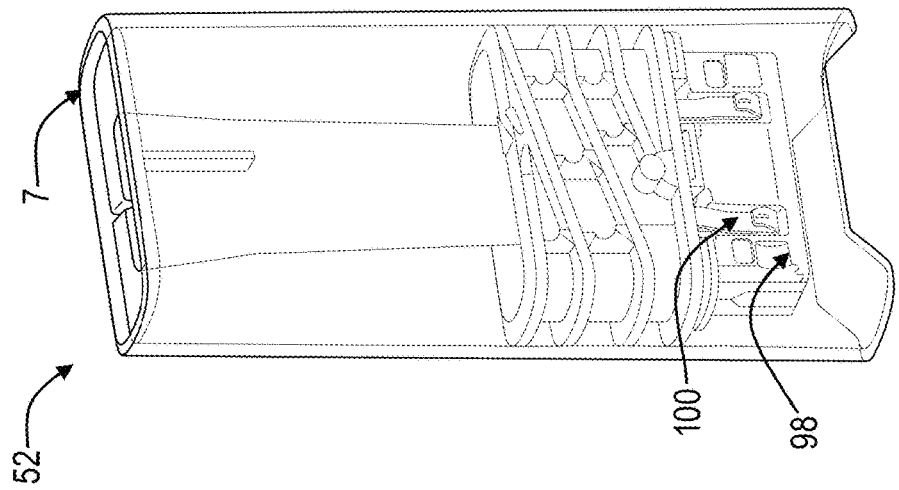
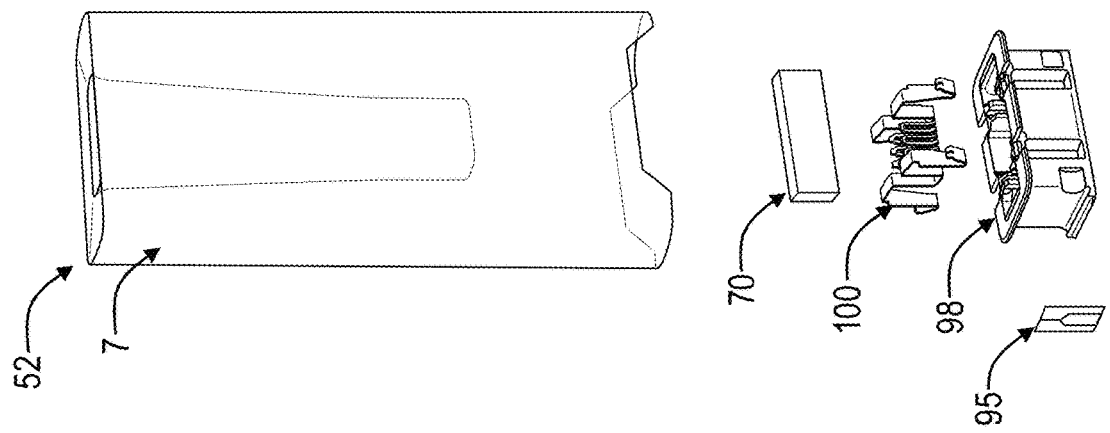

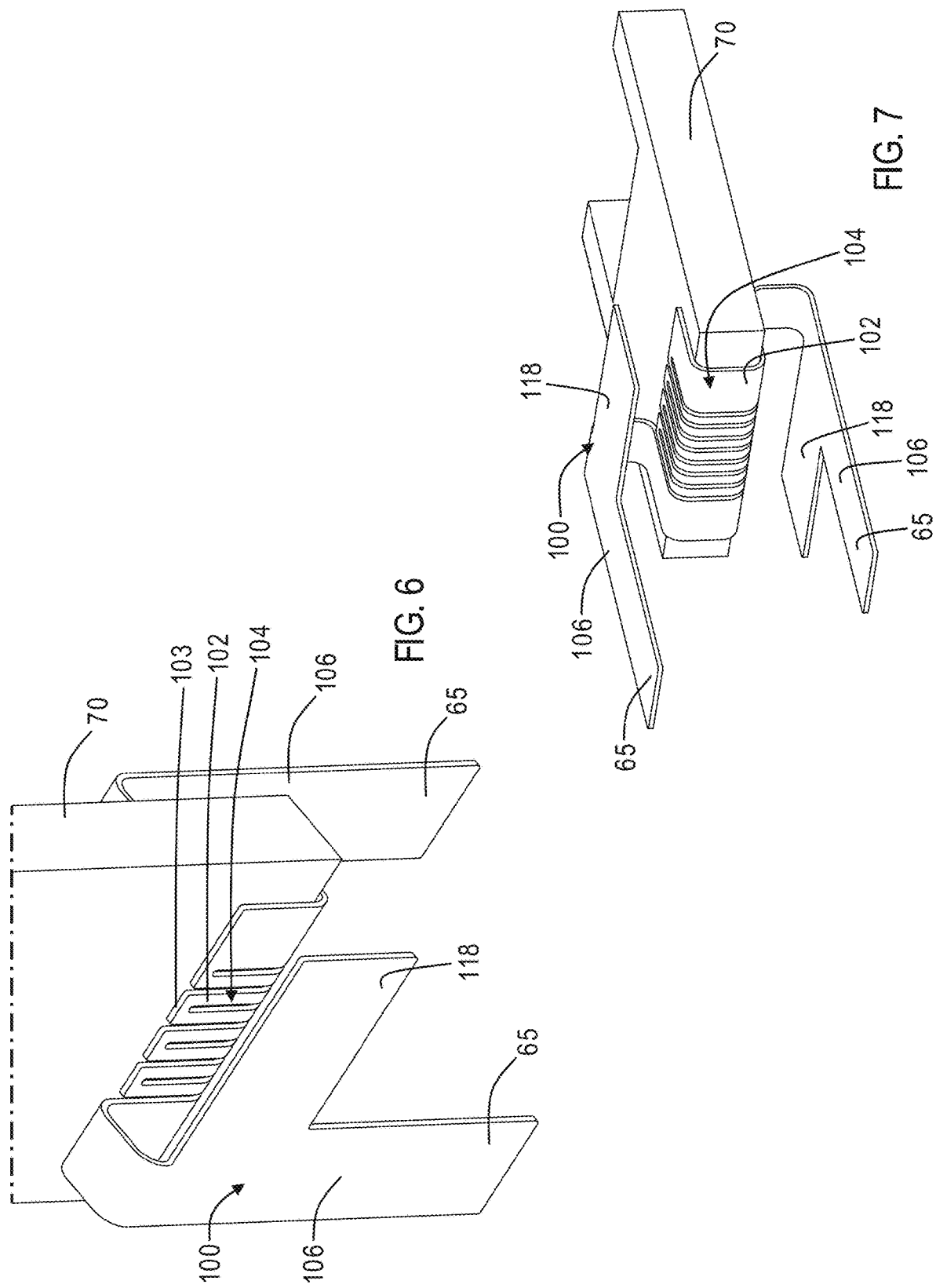

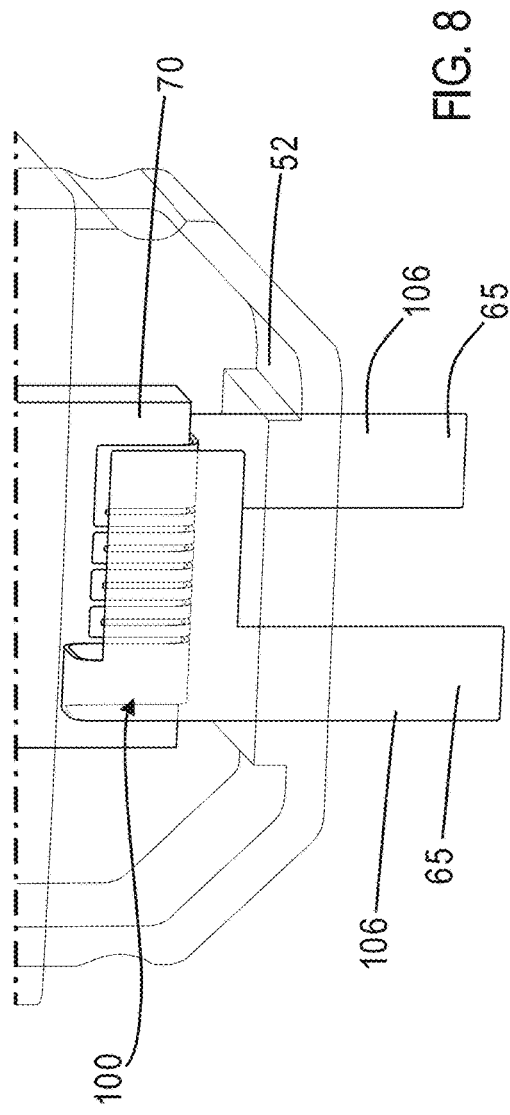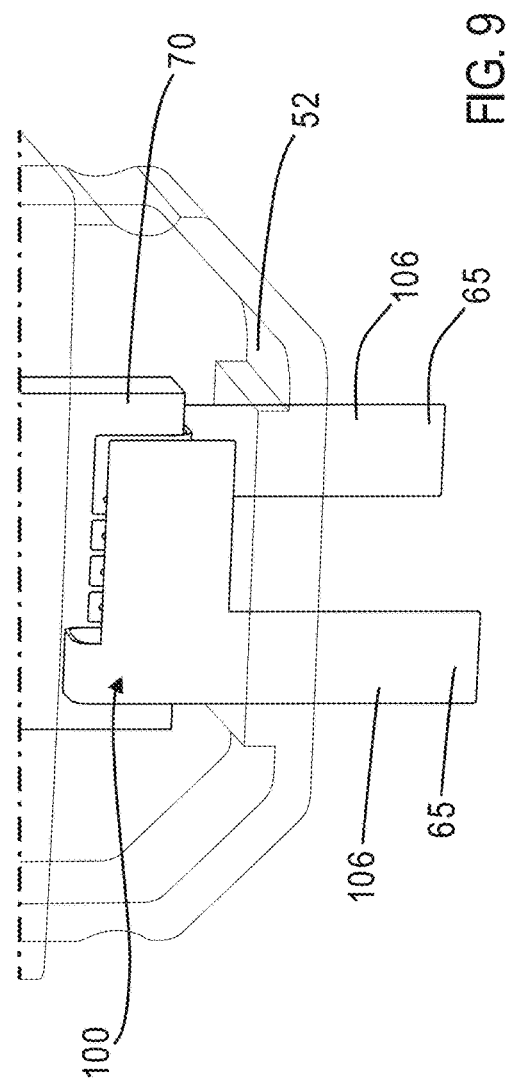

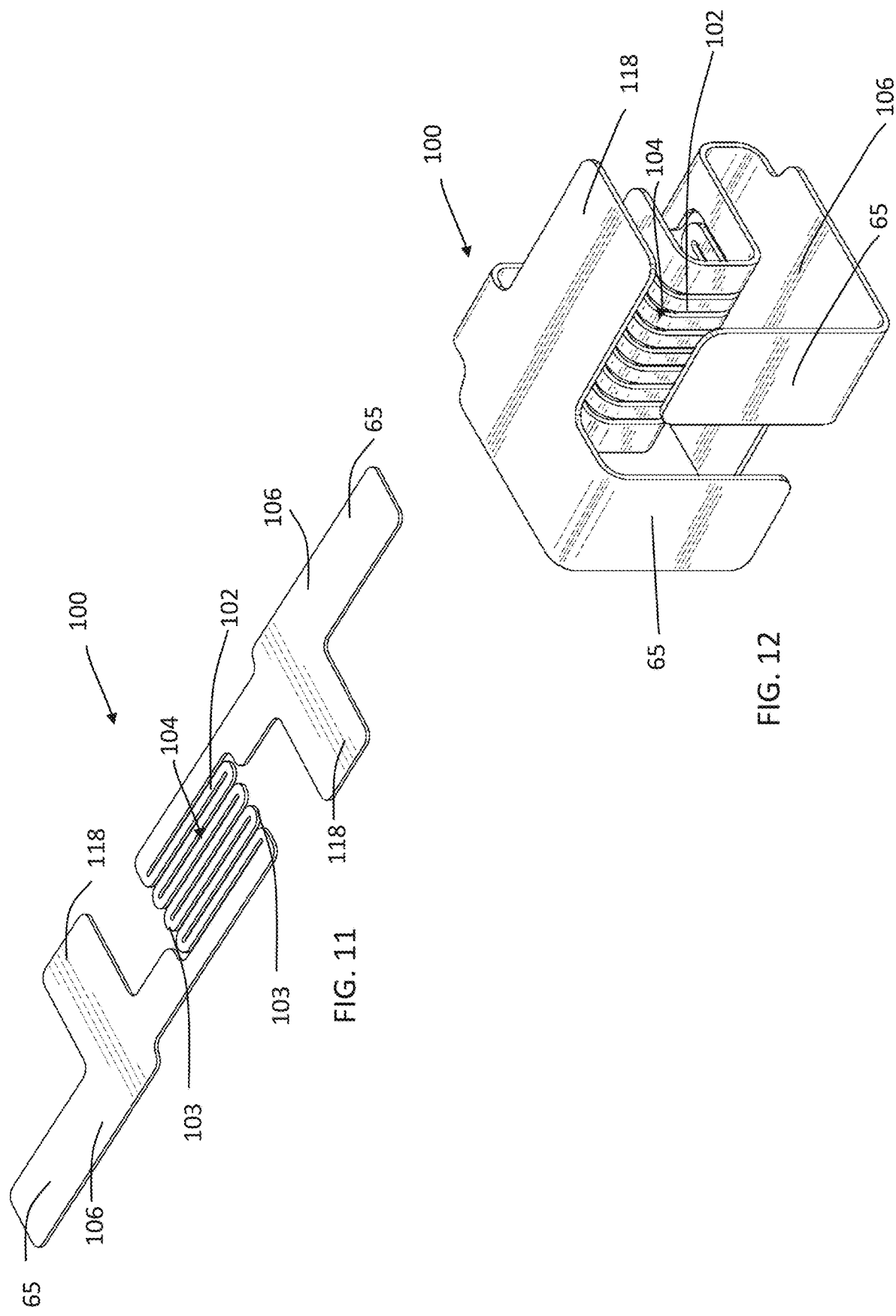

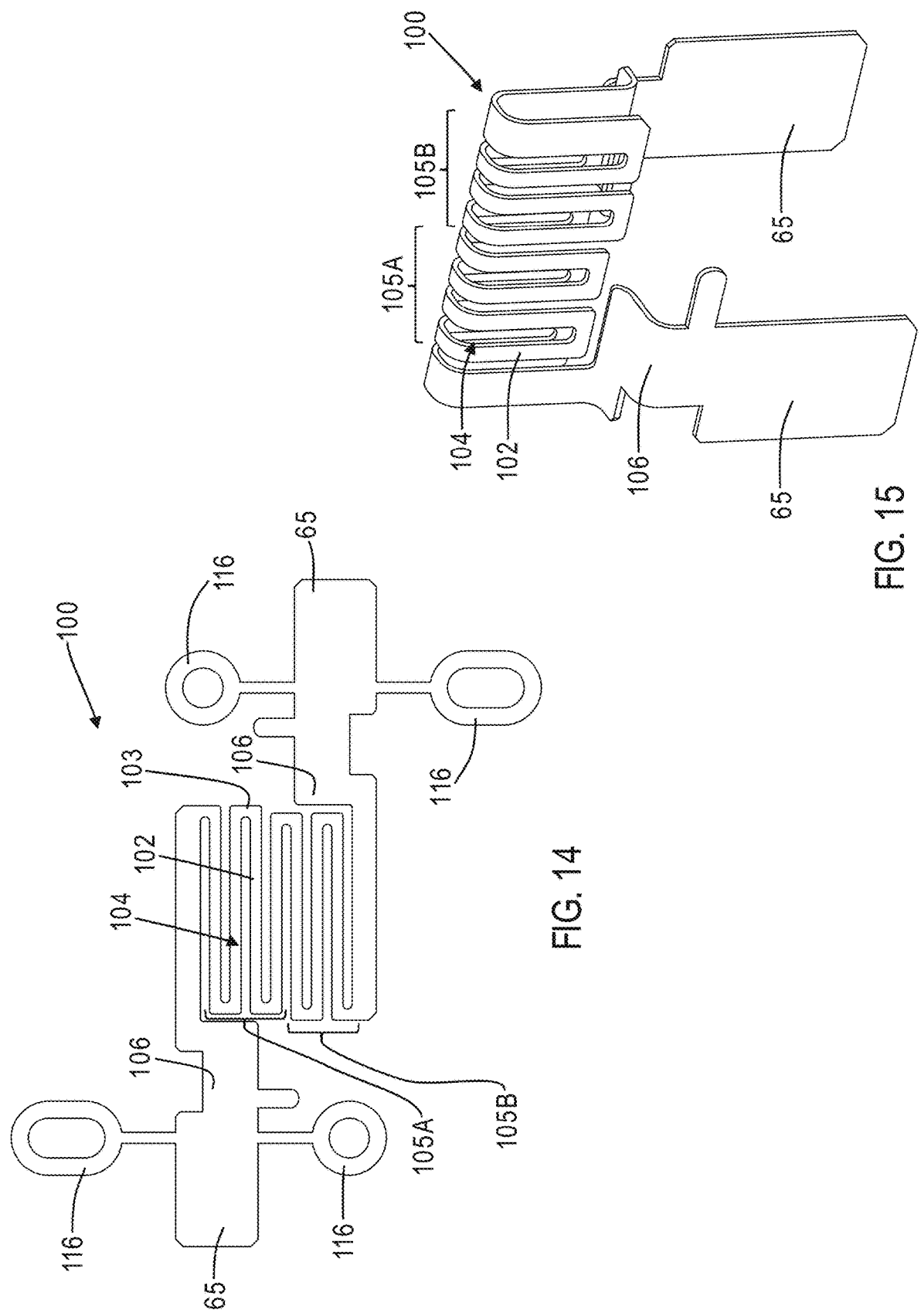

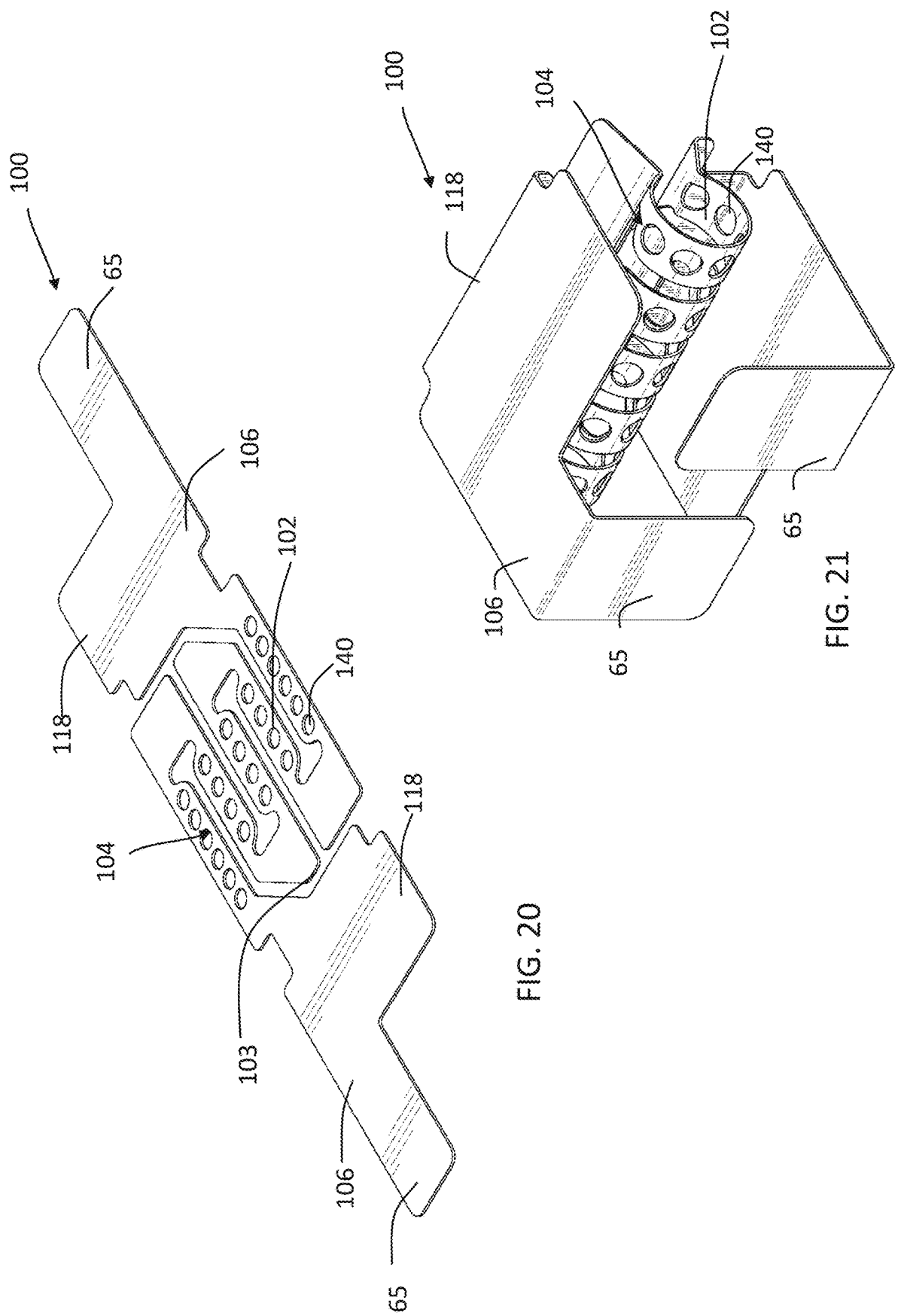

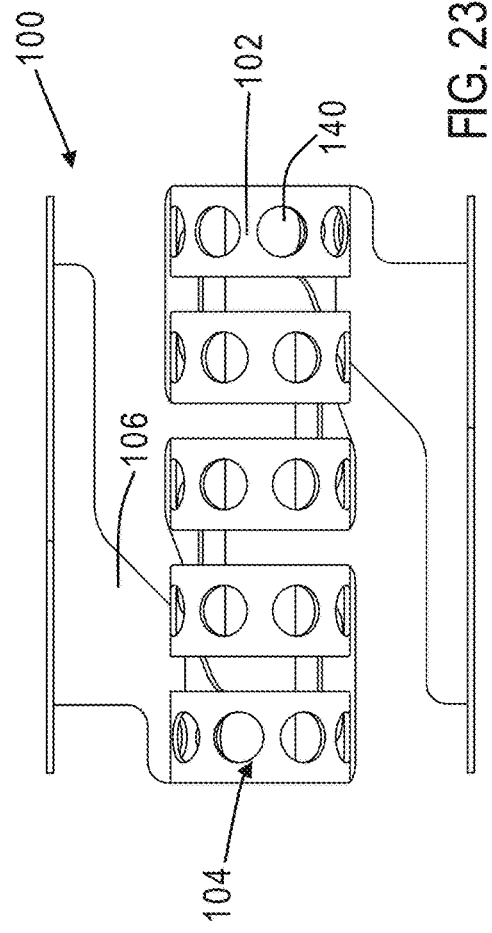
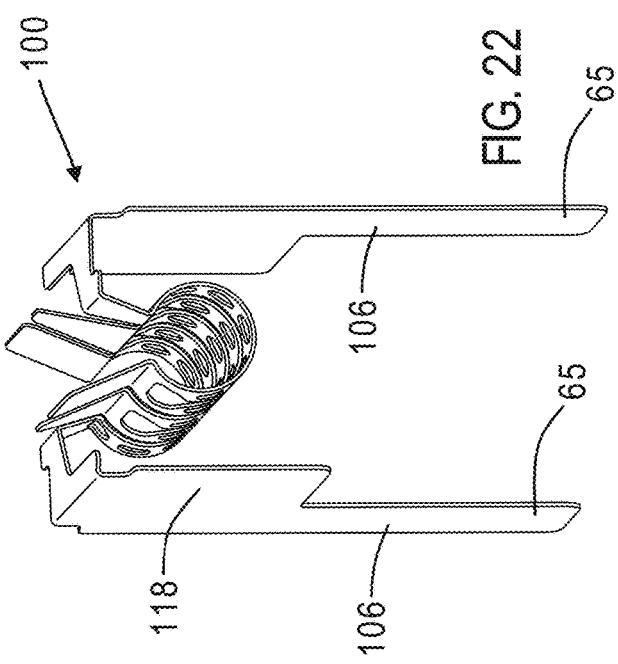
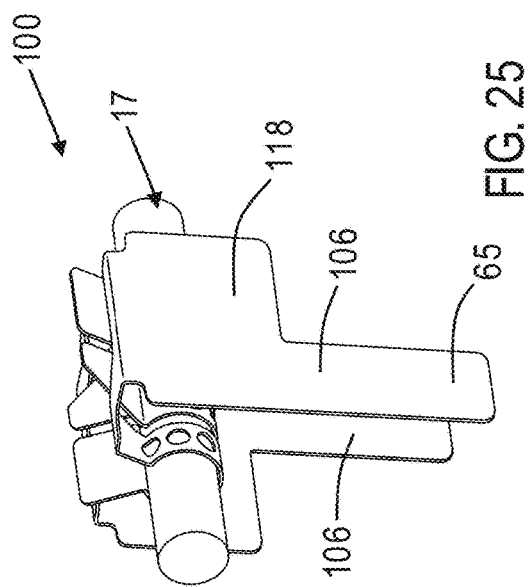

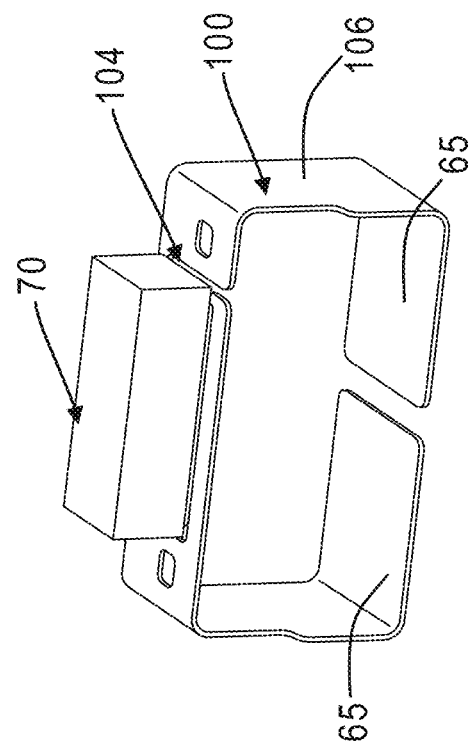
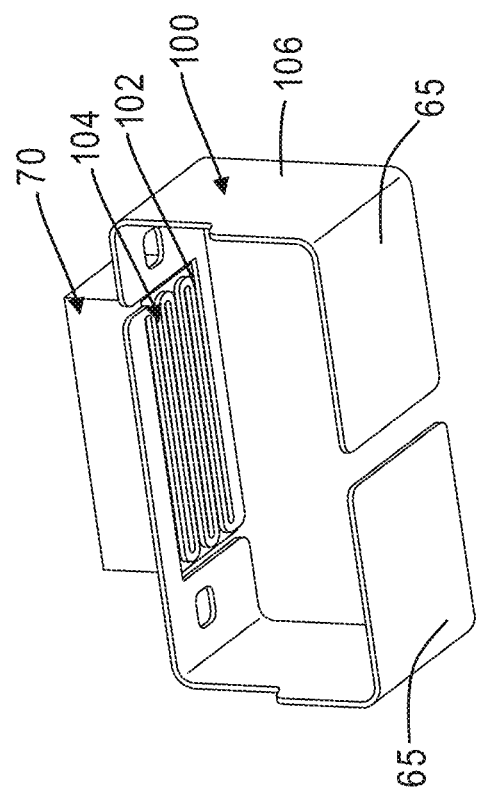

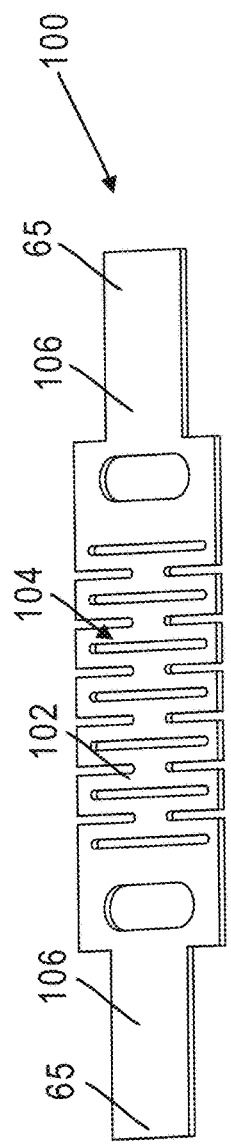
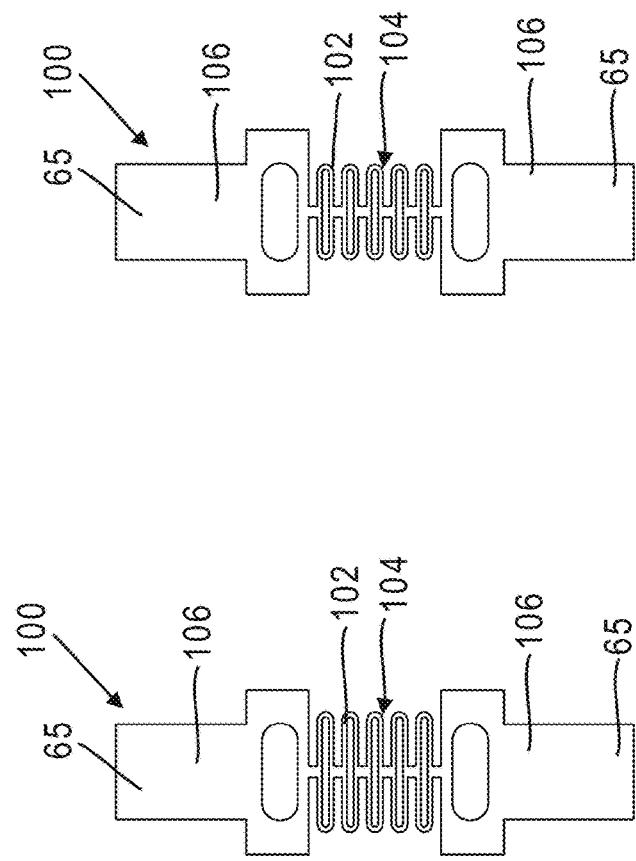
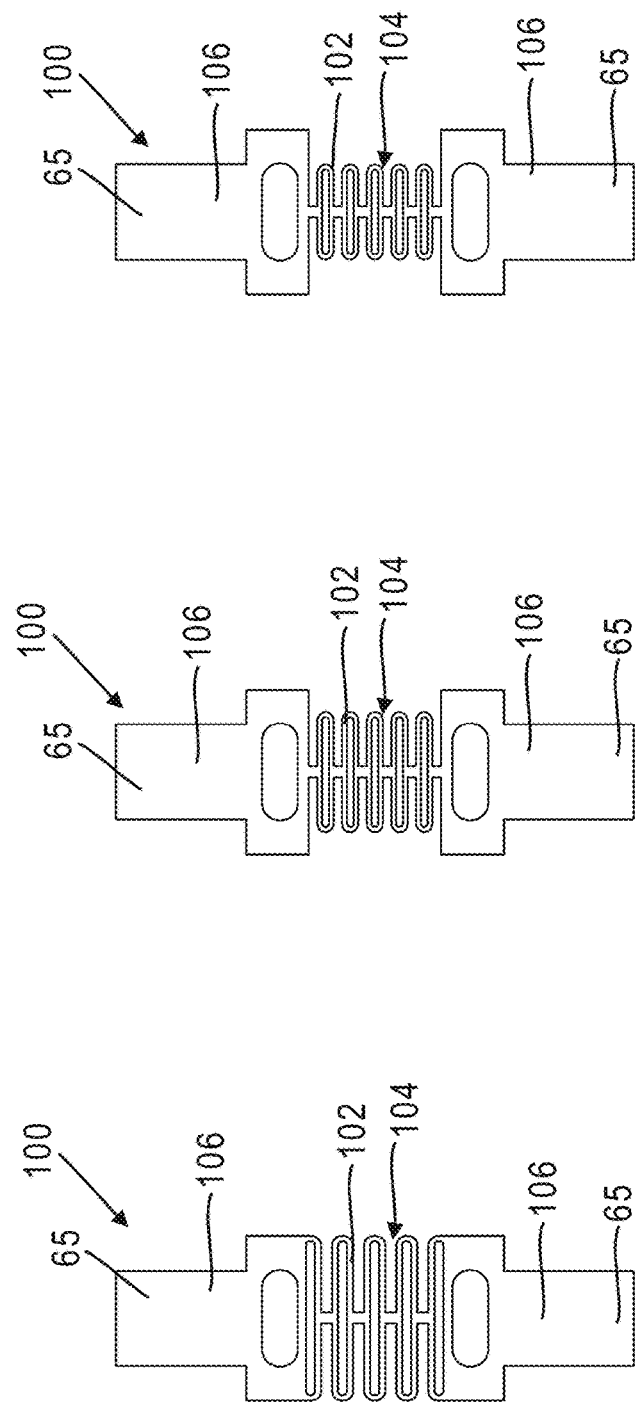
FIG. 28
FIG. 29
FIG. 30
FIG. 31

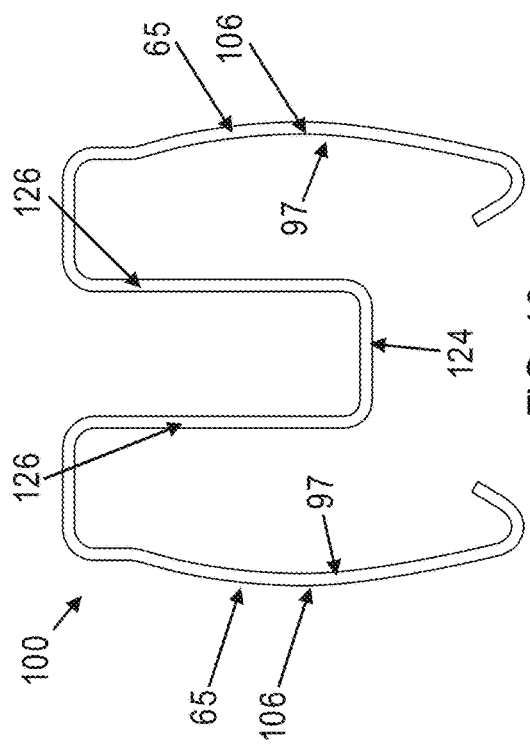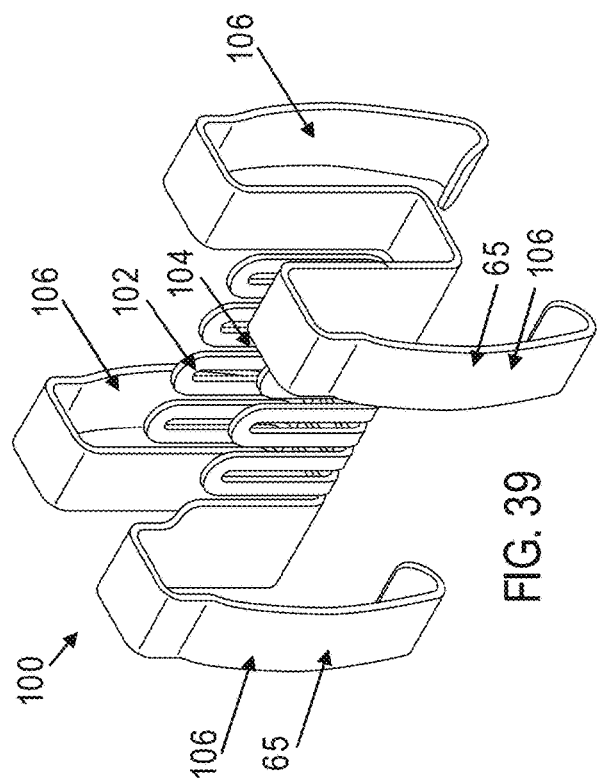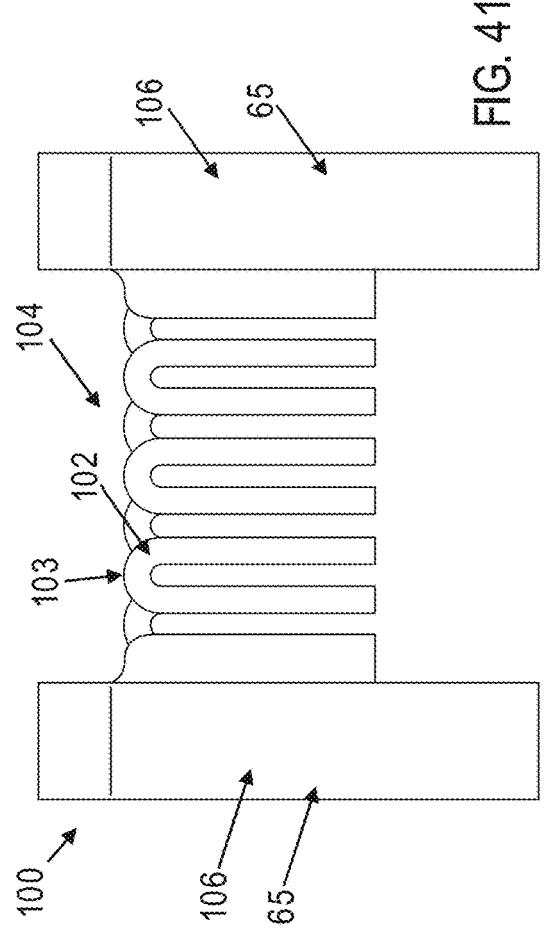

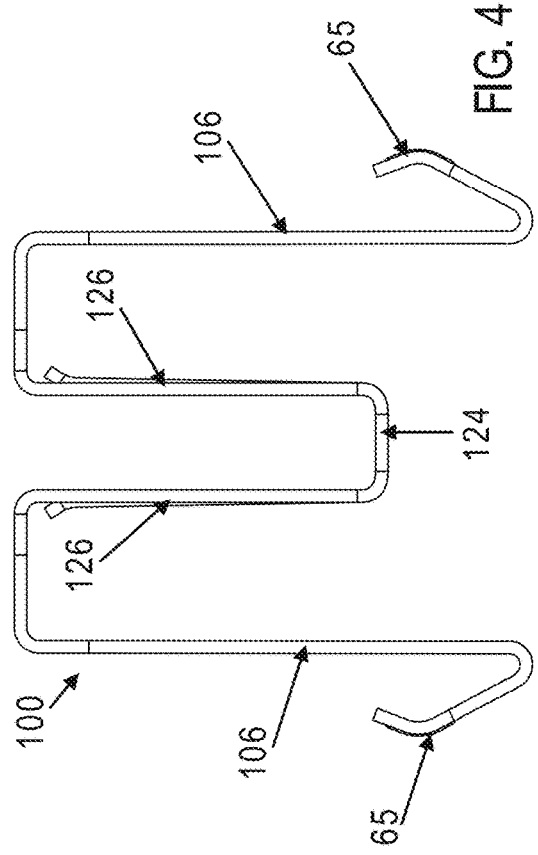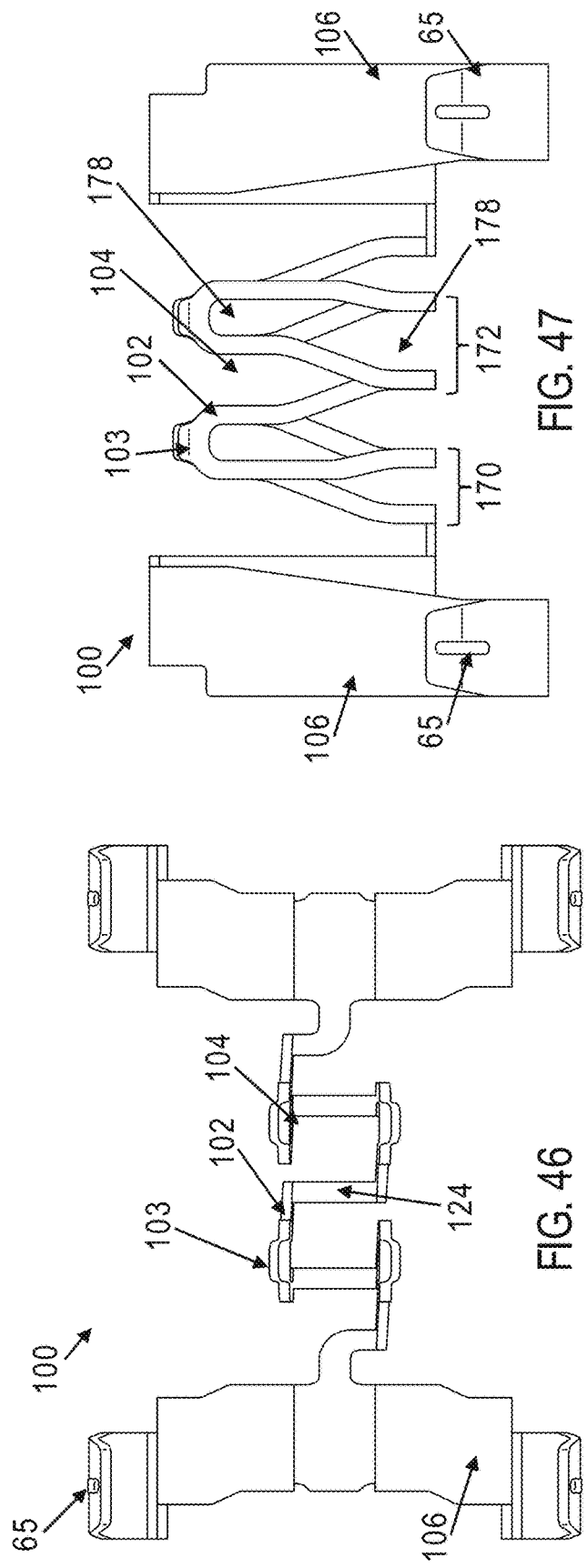

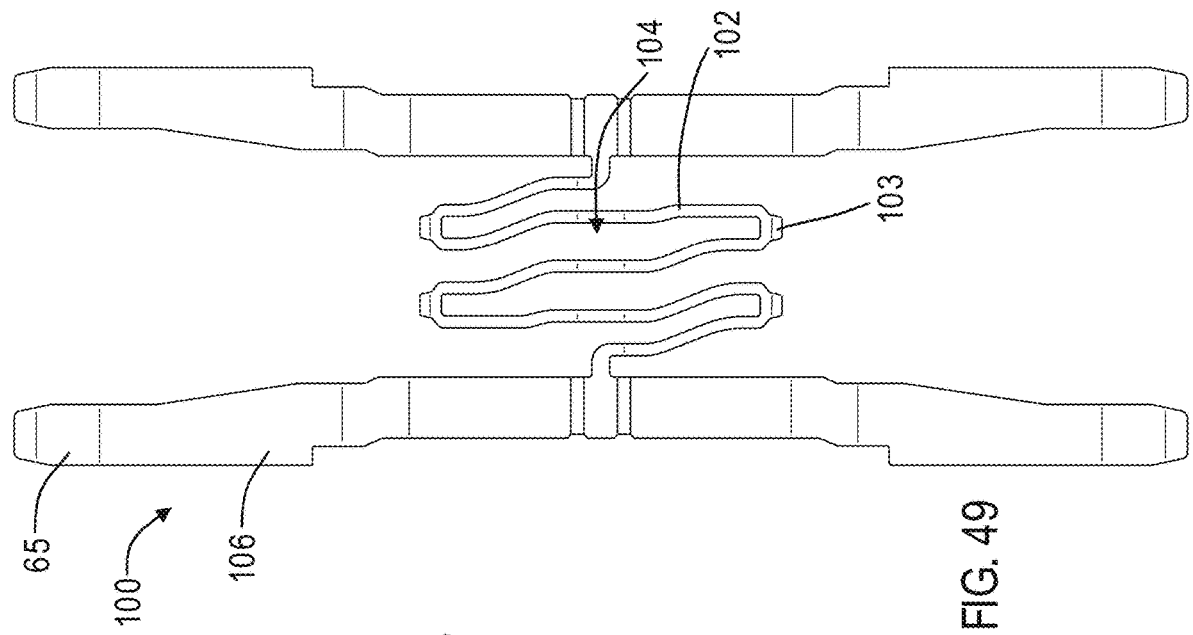
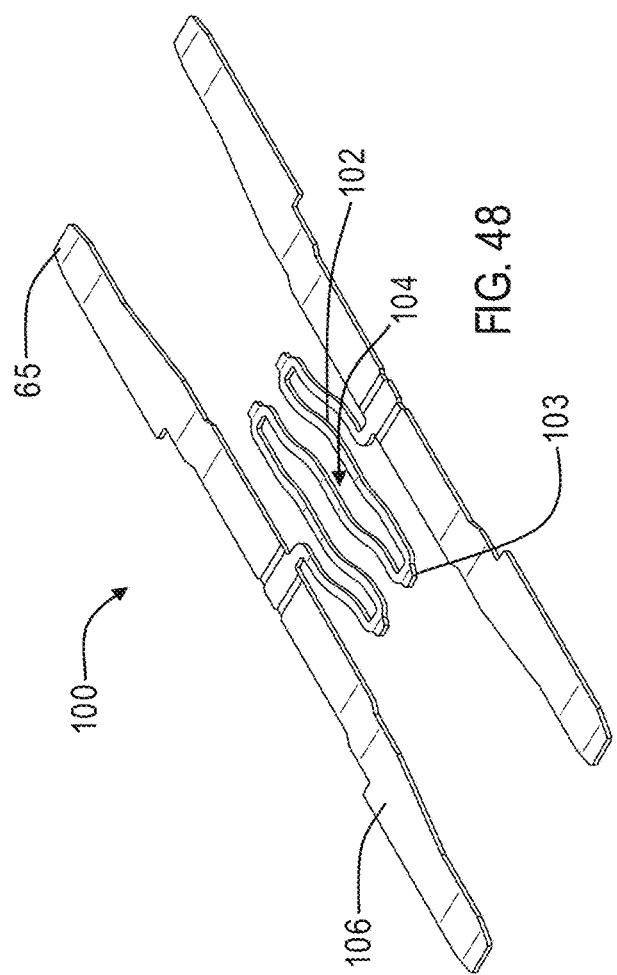

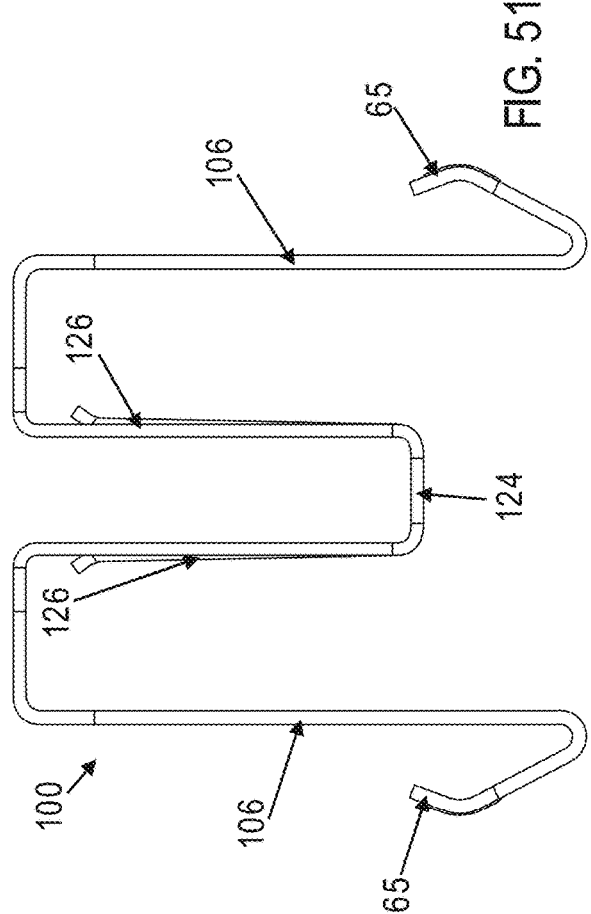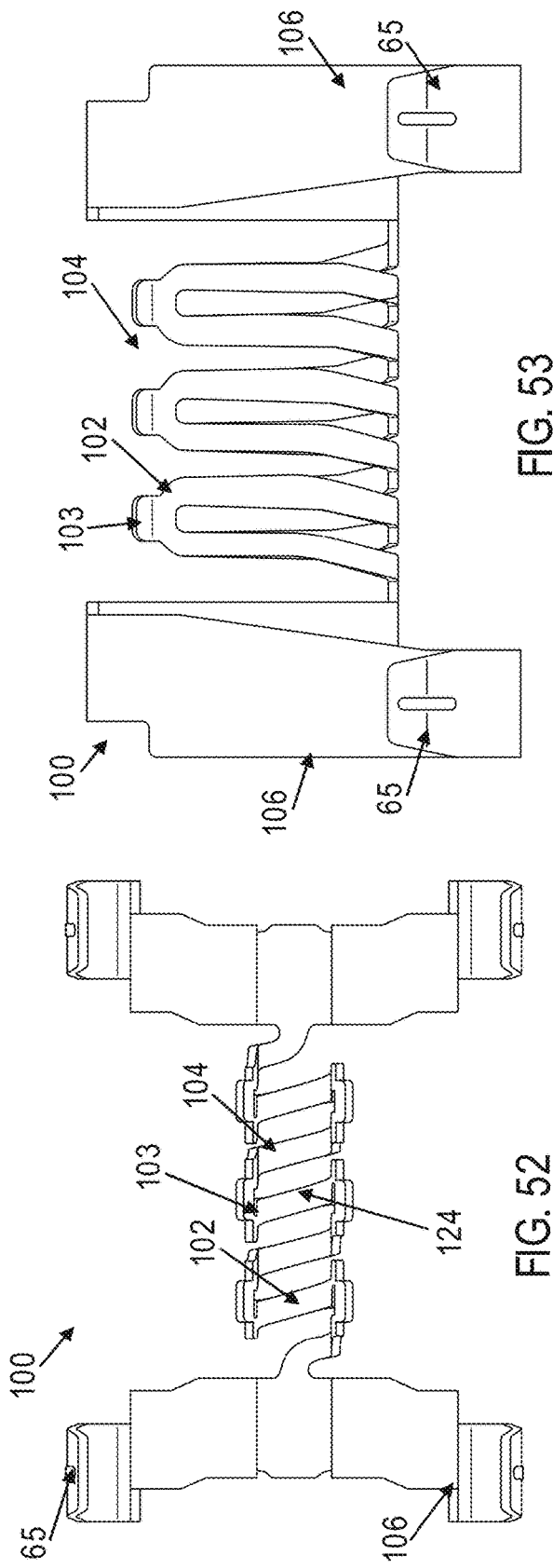

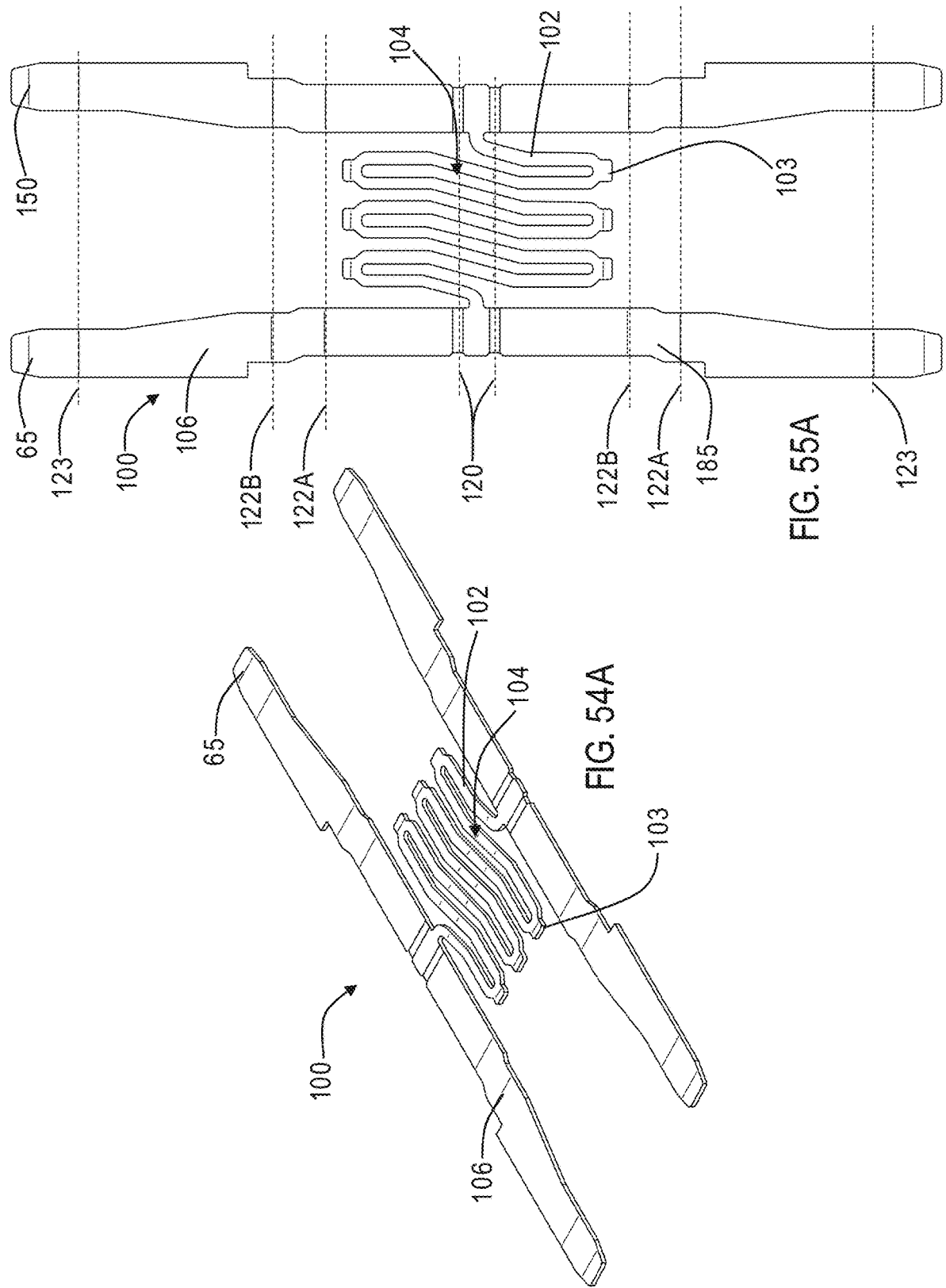

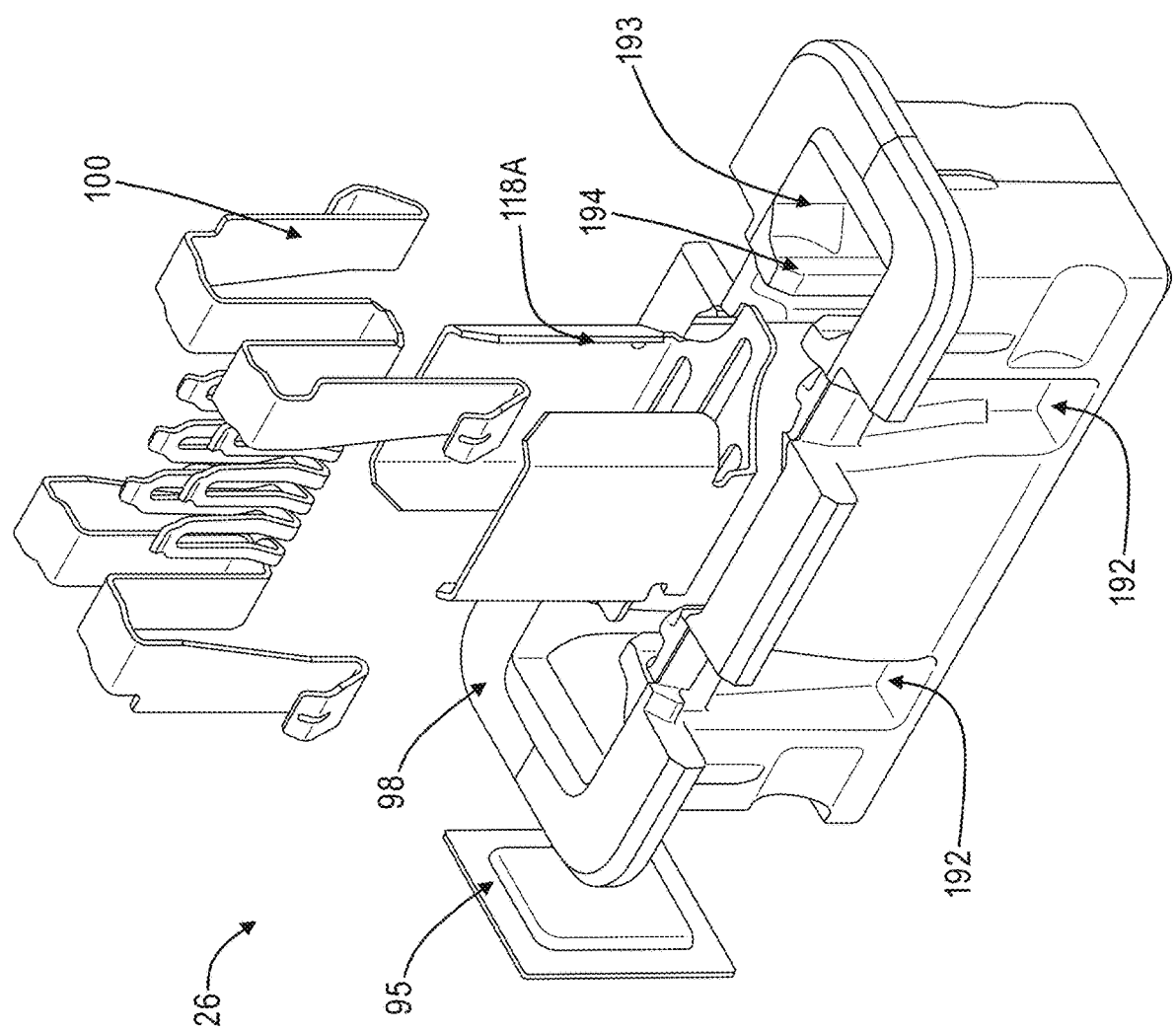

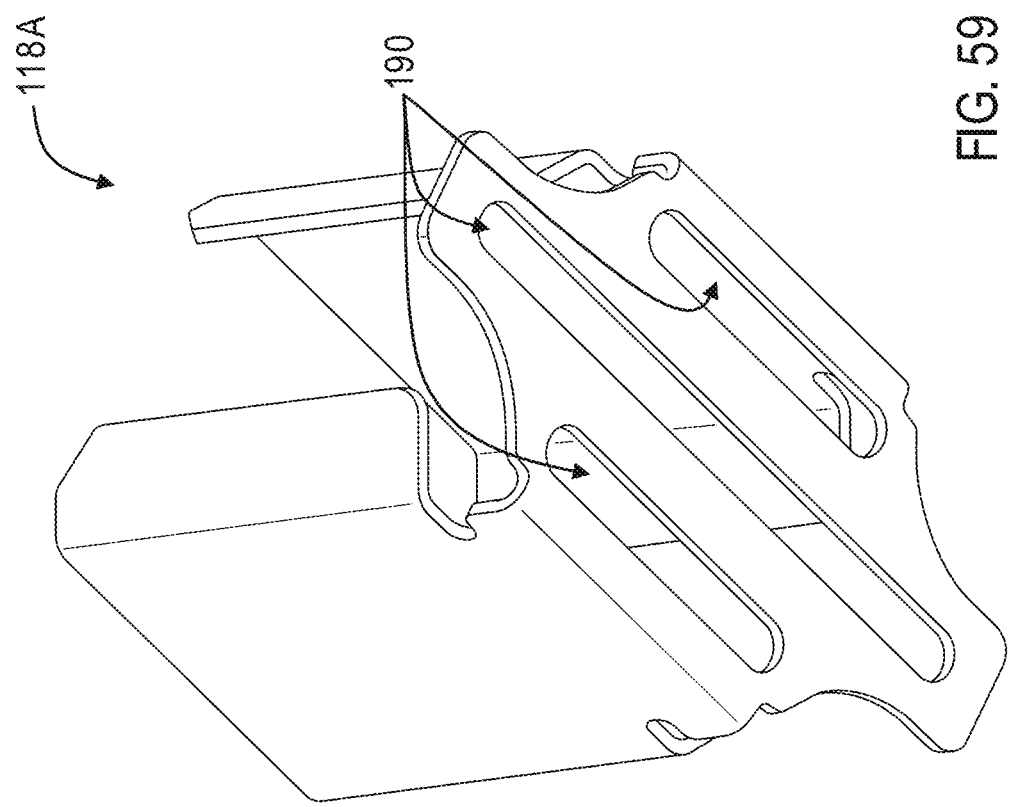

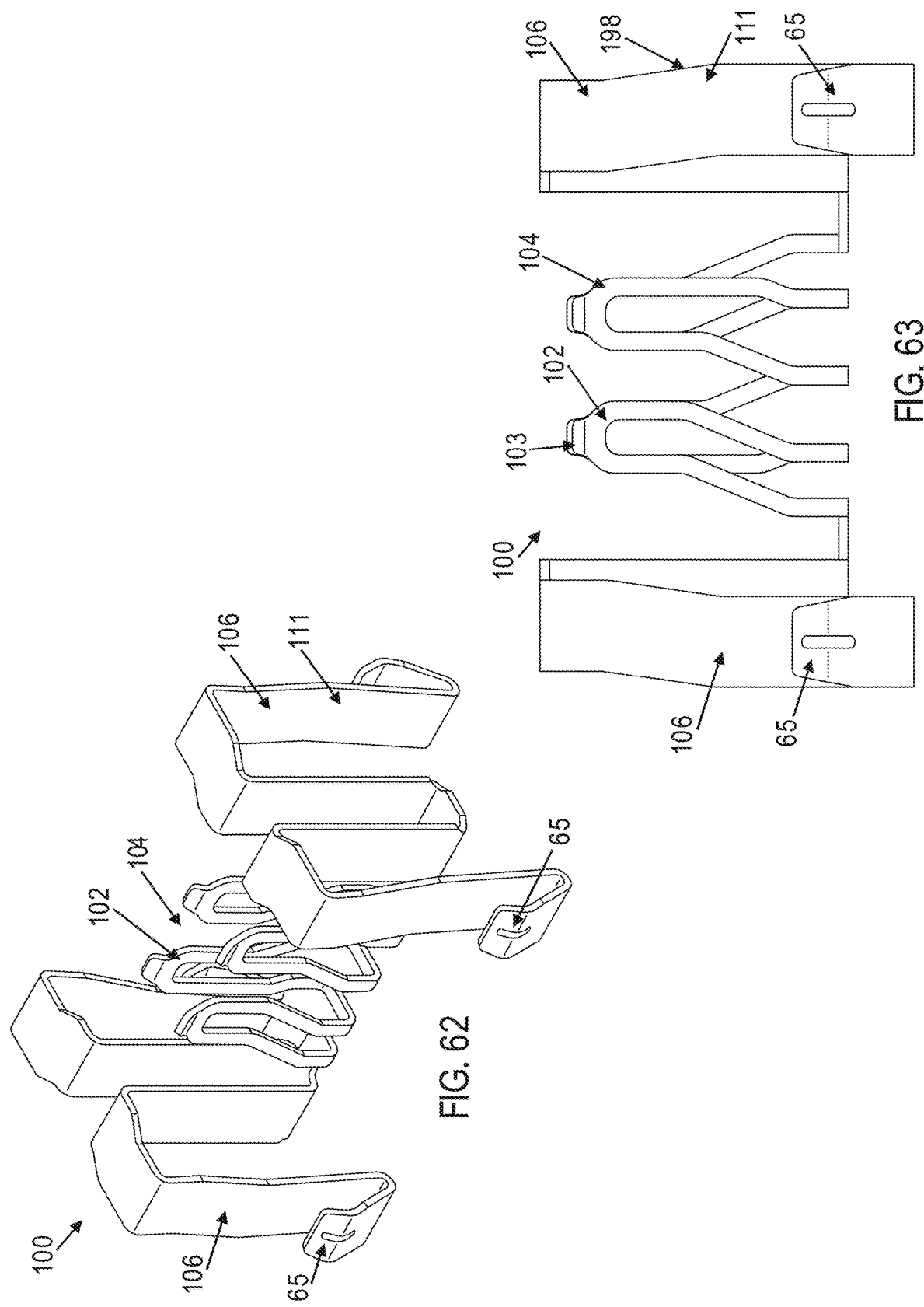

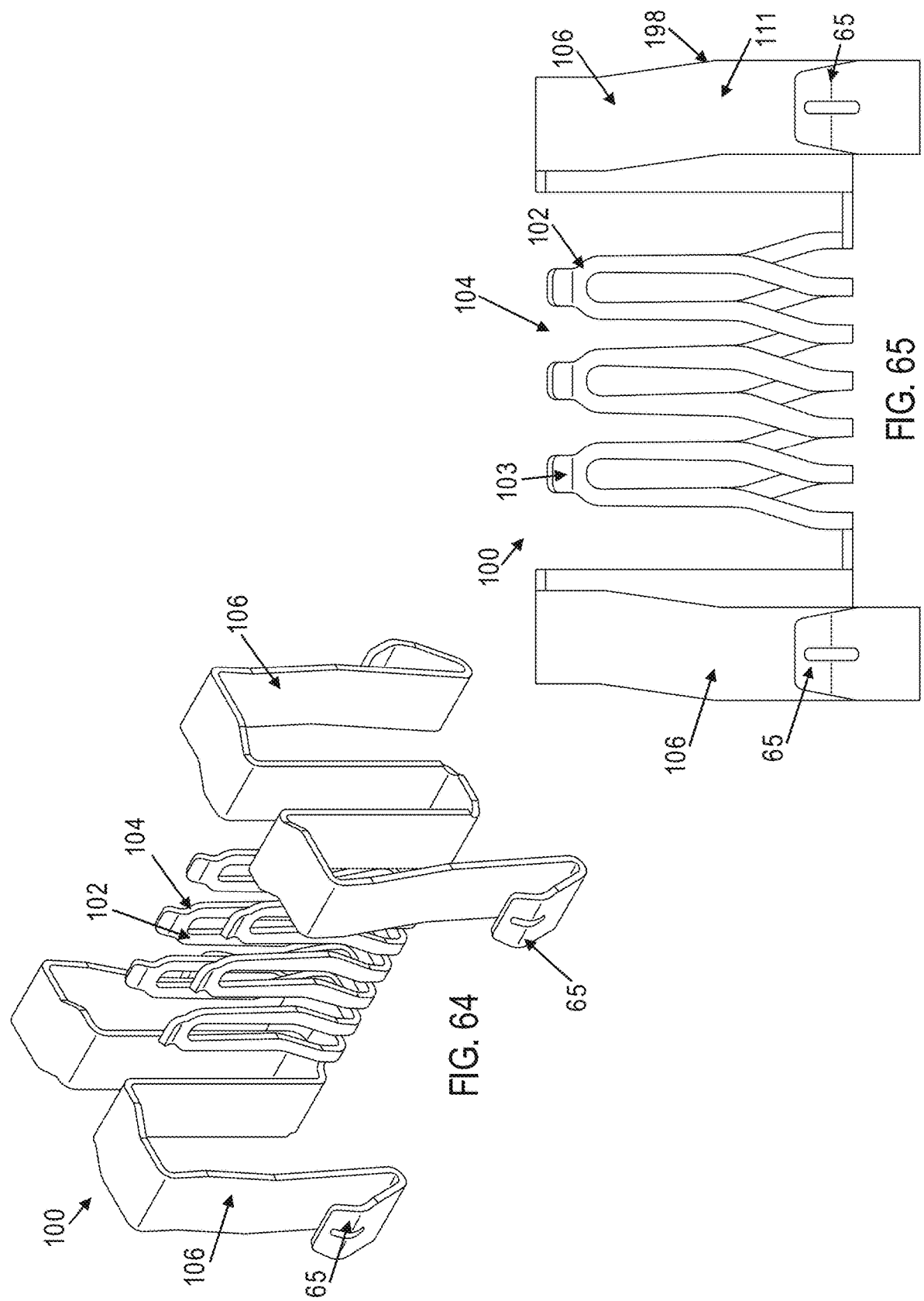

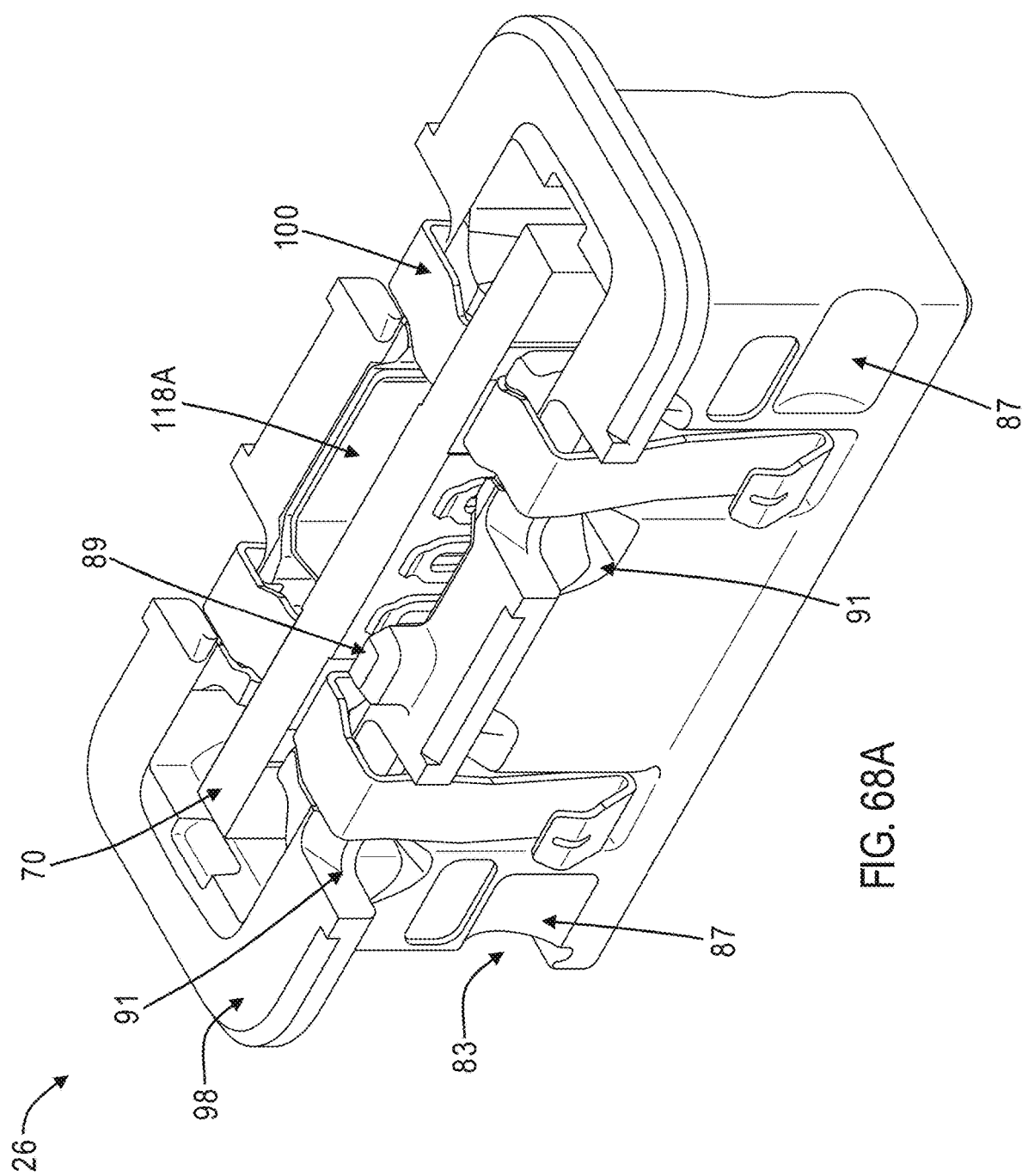

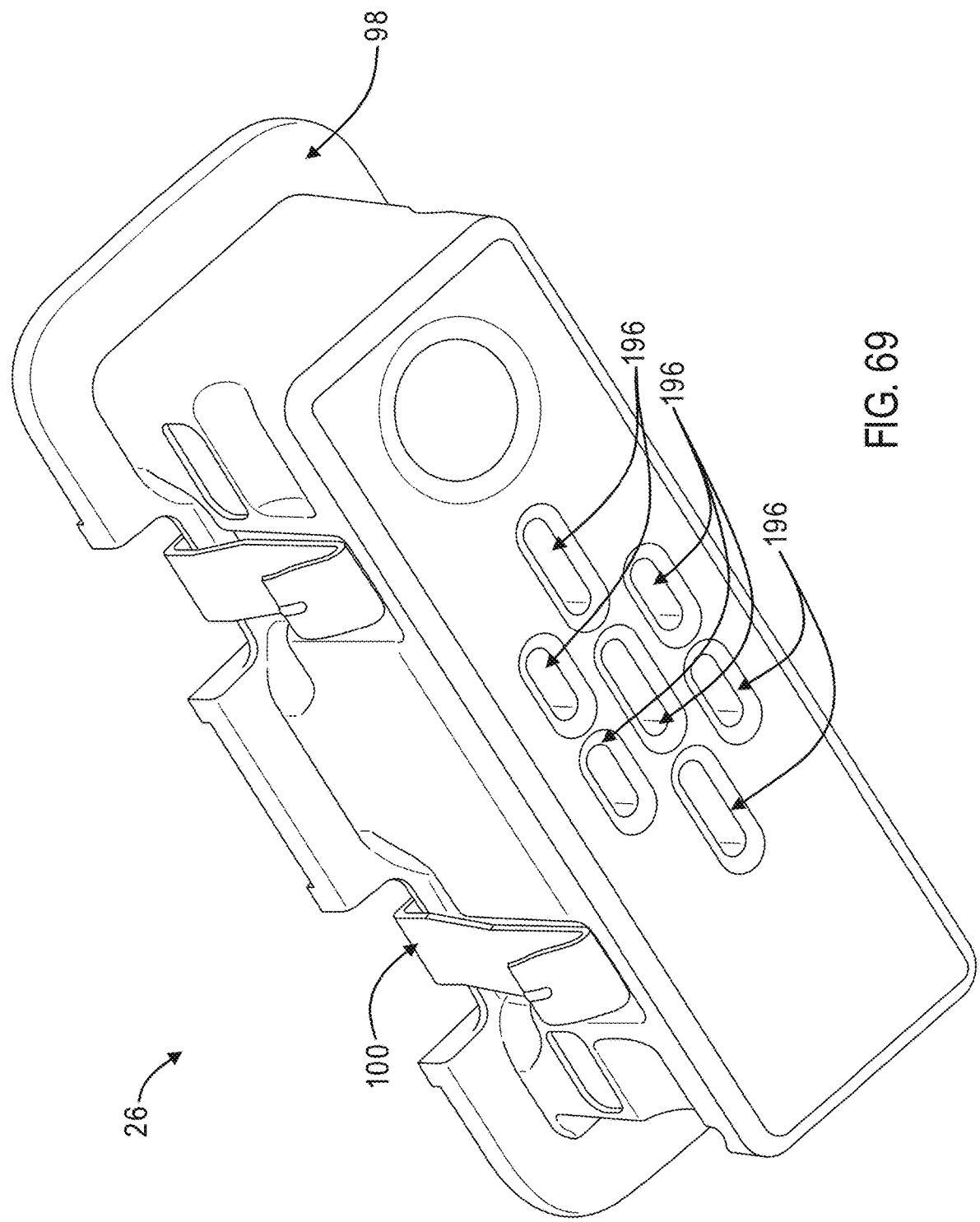

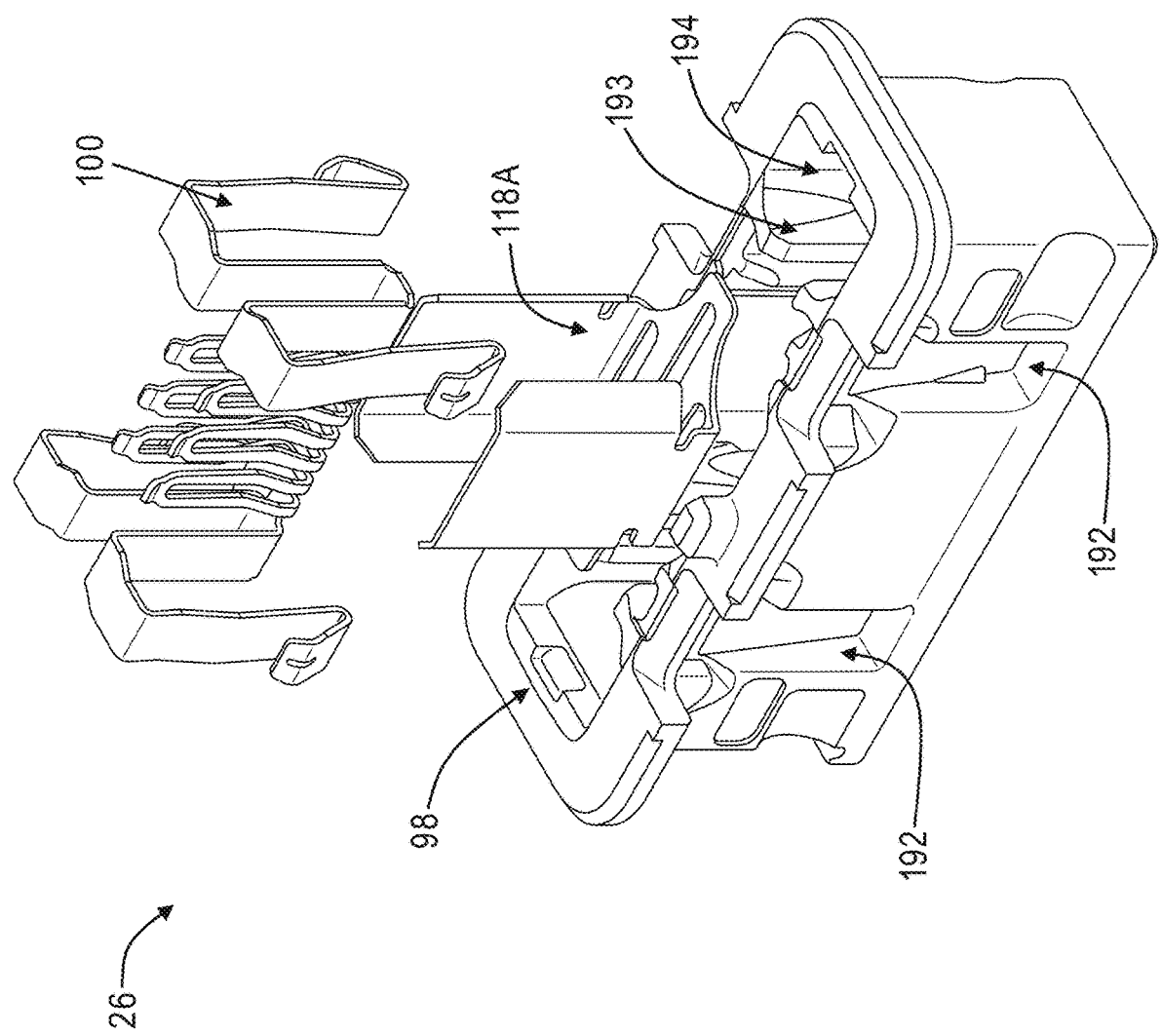

HEATING ELEMENT

CROSS-REFERENCE TO RELATED APPLICATIONS

This application is a continuation of U.S. Nonprovisional patent application Ser. No. 16/653,455, filed on Oct. 15, 2019, and titled "HEATING ELEMENT," which claims priority to U.S. Provisional Application No. 62/913,135, filed on Oct. 9, 2019, and titled "HEATING ELEMENT," U.S. Provisional Application No. 62/745,589, filed on Oct. 15, 2018, and titled "HEATING ELEMENT," U.S. Provisional Application No. 62/812,161, filed on Feb. 28, 2019, and titled "CARTRIDGE FOR A VAPORIZER DEVICE," and U.S. Provisional Application No. 62/747,099, filed on Oct. 17, 2018, and titled "WICK FEED AND HEATING ELEMENTS IN A VAPORIZER DEVICE," the entirety of each of which is incorporated by reference herein.

TECHNICAL FIELD

The subject matter described herein relates to vaporizer devices, including heating elements for vaporizer devices.

BACKGROUND

Vaporizing devices, which can be referred to as vaporizers, electronic vaporizer devices or e-vaporizer devices, can be used for delivery of an aerosol (or "vapor") containing one or more active ingredients by inhalation of the aerosol by a user of the vaporizer device. For example, electronic nicotine delivery systems (ENDS) include a class of vaporizer devices that are battery powered and that may be used to simulate the experience of smoking, but without burning of tobacco or other substances.

In use of a vaporizer device, the user inhales an aerosol, commonly called vapor, which may be generated by a heating element that vaporizes (e.g., causing a liquid or solid to at least partially transition to the gas phase) a vaporizable material, which may be liquid, a solution, a solid, a wax, or any other form as may be compatible with use of a specific vaporizer device. The vaporizable material used with a vaporizer can be provided within a cartridge (e.g., a separable part of the vaporizer that contains the vaporizable material in a reservoir) that includes a mouthpiece (e.g., for inhalation by a user).

To receive the inhalable aerosol generated by a vaporizer device, a user may, in certain examples, activate the vaporizer device by taking a puff, by pressing a button, or by some other approach. A puff, as the term is generally used (and also used herein), refers to inhalation by the user in a manner that causes a volume of air to be drawn into the vaporizer device such that the inhalable aerosol is generated by a combination of vaporized vaporizable material with the air.

A typical approach by which a vaporizer device generates an inhalable aerosol from a vaporizable material involves heating the vaporizable material in a vaporization chamber (or a heater chamber) to cause the vaporizable material to be converted to the gas (or vapor) phase. A vaporization chamber generally refers to an area or volume in the vaporizer device within which a heat source (e.g., conductive, convective, and/or radiative) causes heating of a vaporizable material to produce a mixture of air and vaporized vaporizable material to form a vapor for inhalation by a user of the vaporization device.

The term vaporizer device, as used herein consistent with the current subject matter, generally refers to portable, self-contained devices that are convenient for personal use. Typically, such devices are controlled by one or more switches, buttons, touch sensitive devices, or other user input functionality or the like (which can be referred to generally as controls) on the vaporizer, although a number of devices that may wirelessly communicate with an external controller (e.g., a smartphone, a smart watch, other wearable electronic devices, etc.) have recently become available. Control, in this context, refers generally to an ability to influence one or more of a variety of operating parameters, which may include without limitation any of causing the heater to be turned on and/or off, adjusting a minimum and/or maximum temperature to which the heater is heated during operation, various games or other interactive features that a user might access on a device, and/or other operations.

Various vaporizable materials having a variety of contents and proportions of such contents can be contained in the cartridge. Some vaporizable materials, for example, may have a smaller percentage of active ingredients per total volume of vaporizable material, such as due to regulations requiring certain active ingredient percentages. As a result, a user may need to vaporize a large amount of vaporizable material (e.g., compared to the overall volume of vaporizable material that can be stored in a cartridge) to achieve a desired effect.

SUMMARY

Aspects of the current subject matter relate to a heating element for use in a vaporizer device.

A heating element may include a heating portion and at least two legs. The heating portion may include at least two tines spaced apart from one another. The heating portion may be preformed to define an interior volume configured to receive the wicking element such that the heating portion secures at least a portion of the wicking element to the heating element. The heating portion may be configured to contact at least two separate surfaces of the wicking element. The at least two legs may be coupled to the at least two tines and spaced apart from the heating portion. The at least two legs may be configured to electrically communicate with a power source. Power is configured to be supplied to the heating portion from the power source to generate heat, thereby vaporizing the vaporizable material stored within the wicking element.

In some implementations, the at least two legs includes four legs. In some implementations, the heating portion is configured to contact at least three separate surfaces of the wicking element.

In some implementations, the at least two tines includes a first side tine portion, a second side tine portion opposing the first side tine portion, and a platform tine portion connecting the first side tine portion with the second side tine portion. The platform tine portion may be positioned approximately perpendicular to a portion of the first side tine portion and the second side tine portion. The first side tine portion, the second side tine portion, and the platform tine portion defines the interior volume in which the wicking element is positioned. In some implementations, the at least two legs are located away from the heating portion by a bridge.

In some implementations, each of the at least two legs includes a cartridge contact positioned at an end of each of the at least two legs. The cartridge contact may electrically communicate with the power source. The cartridge contact may be angled and extend away from the heating portion.

In some implementations, the at least two tines includes a first pair of tines and a second pair of tines. In some implementations, the tines of the first pair of tines are evenly spaced from one another. In some implementations, the tines of the first pair of tines are spaced apart by a width. In some implementations, the width is greater at an inner region of the heating element adjacent the platform tine portion than the width at an outer region of the heating element adjacent an outer edge of the first side tine portion opposite the inner region.

In some implementations, the vaporizer device is configured to measure a resistance of the heating element at each of the four legs to control a temperature of the heating element. In some implementations, the heating element includes a heat shield configured to insulate the heating portion from a body of the vaporizer device.

In some implementations, the vaporizer device further includes a heat shield configured to surround at least a portion of the heating element and insulate the heating portion from a body of a wick housing configured to surround at least a portion of the wicking element and the heating element.

In some implementations, the heating portion is folded between the heating portion and the at least two legs to isolate the heating portion from the at least two legs. In some implementations, the heating portion further includes at least one tab that extends from a side of the at least two tines to allow for easier entry of the wicking element to the interior volume of the heating portion. In some implementations, the at least one tab extends away from the interior volume at an angle.

In some implementations, the at least two legs includes a capillary feature. The capillary feature may cause an abrupt change in capillary pressure to thereby prevent the vaporizable material from flowing beyond the capillary feature. In some implementations, the capillary feature comprises one or more bends in the at least two legs. In some implementations, the at least two legs extend at an angle towards the interior volume of the heating portion, the angled at least two legs defining the capillary feature.

In some implementations, a vaporizer device includes a reservoir containing vaporizable material, a wicking element in fluid communication with the reservoir, and a heating element. The heating element includes a heating portion and at least two legs. The heating portion may include at least two tines spaced apart from one another. The heating portion may be preformed to define an interior volume configured to receive the wicking element such that the heating portion secures at least a portion of the wicking element to the heating element. The heating portion may be configured to contact at least two separate surfaces of the wicking element. At least two legs may be coupled to the at least two tines and spaced apart from the heating portion. The at least two legs may be configured to electrically communicate with a power source. Power is configured to be supplied to the heating portion from the power source to generate heat, thereby vaporizing the vaporizable material stored within the wicking element.

A method of forming an atomizer assembly for a vaporizer device may include securing a wicking element to an interior volume of a heating element. The heating element may include a heating portion comprising at least two tines spaced apart from one another, and at least two legs spaced from the heating portion. The legs may be configured to electrically communicate with a power source of the vaporizer device. The heating portion is configured to contact at least two surfaces of the wicking element. The method may also include coupling the heating element to a wick housing configured to surround at least a portion of the wicking element and the heating element. The securing may also include sliding the wicking element into the interior volume of the heating element.

In some implementations, a vaporizer device includes a heating portion comprising one or more heater traces integrally formed and spaced apart from one another, the one or more heater traces configured to contact at least a portion of a wicking element of the vaporizer device, a connecting portion configured to receive power from a power source and direct the power to the heating portion, and a plating layer having a plating material that is different from a material of the heating portion. The plating layer may be configured to reduce contact resistance between the heating element and the power source, thereby localizing heating of the heating element to the heating portion.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings:

FIG. 1A shows a block diagram of a vaporizer consistent with implementations of the current subject matter;

FIG. 1B illustrates a top view of an embodiment of the vaporizer of FIG. 1A, showing a cartridge separated from a vaporizer body;

FIG. 1C illustrates a top view of an embodiment of the vaporizer of FIG. 1A, showing the cartridge coupled to the vaporizer body;

FIG. 1D illustrates a perspective exploded view of an embodiment of a cartridge, consistent with implementations of the current subject matter;

FIG. 1E illustrates a top perspective view of an embodiment of a cartridge consistent with implementations of the current subject matter;

FIG. 1F illustrates a bottom perspective view of an embodiment of a cartridge consistent with implementations of the current subject matter;

FIG. 6 shows a heating element and a wicking element consistent with implementations of the current subject matter;

FIG. 7 shows a heating element and a wicking element consistent with implementations of the current subject matter;

FIG. 8 shows a heating element and a wicking element positioned within a vaporizer cartridge consistent with implementations of the current subject matter;

FIG. 9 shows a heating element and a wicking element positioned within a vaporizer cartridge consistent with implementations of the current subject matter;

FIG. 11 shows a heating element in an unbent position consistent with implementations of the current subject matter;

FIG. 12 shows a heating element in a bent position consistent with implementations of the current subject matter;

FIG. 14 shows a heating element in an unbent position consistent with implementations of the current subject matter;

FIG. 15 shows a heating element in a partially bent position consistent with implementations of the current subject matter;

FIG. 20 shows a heating element in an unbent position consistent with implementations of the current subject matter;

FIG. 21 shows a heating element in a bent position consistent with implementations of the current subject matter;

FIG. 22 shows a heating element in a partially bent position consistent with implementations of the current subject matter;

FIG. 23 shows a heating element in a partially bent position consistent with implementations of the current subject matter;

FIG. 24 shows a heating element in a partially bent position consistent with implementations of the current subject matter;

FIG. 25 shows a heating element in a partially bent position and a wicking element consistent with implementations of the current subject matter;

FIG. 26 shows a heating element in a bent position and a wicking element consistent with implementations of the current subject matter;

FIG. 27 shows a heating element in a bent position and a wicking element consistent with implementations of the current subject matter;

FIG. 28 shows a heating element in an unbent position consistent with implementations of the current subject matter;

FIG. 29 shows a heating element in an unbent position consistent with implementations of the current subject matter;

FIG. 30 shows a heating element in an unbent position consistent with implementations of the current subject matter;

FIG. 31 shows a heating element in an unbent position consistent with implementations of the current subject matter;

FIG. 39 shows a perspective view of a heating element in a bent position consistent with implementations of the current subject matter;

FIG. 40 shows a side view of a heating element in a bent position consistent with implementations of the current subject matter;

FIG. 41 shows a front view of a heating element in a bent position consistent with implementations of the current subject matter;

FIG. 45 shows a side view of a heating element in a bent position consistent with implementations of the current subject matter;

FIG. 46 shows a top view of a heating element in a bent position consistent with implementations of the current subject matter;

FIG. 47 shows a front view of a heating element in a bent position consistent with implementations of the current subject matter;

FIG. 48 shows a perspective view of a heating element in an unbent position consistent with implementations of the current subject matter;

FIG. 49 shows a top view of a heating element in an unbent position consistent with implementations of the current subject matter;

FIG. 51 shows a side view of a heating element in a bent position consistent with implementations of the current subject matter;

FIG. 52 shows a top view of a heating element in a bent position consistent with implementations of the current subject matter;

FIG. 53 shows a front view of a heating element in a bent position consistent with implementations of the current subject matter;

FIG. 54A shows a perspective view of a heating element in an unbent position consistent with implementations of the current subject matter;

FIG. 55A shows a top view of a heating element in an unbent position consistent with implementations of the current subject matter;

FIG. 58 shows an exploded perspective view of an atomizer assembly consistent with implementations of the current subject matter;

FIG. 59 shows a perspective view of a heat shield consistent with implementations of the current subject matter;

FIG. 62 shows a perspective view of a heating element in a bent position consistent with implementations of the current subject matter;

FIG. 63 shows a side view of a heating element in a bent position consistent with implementations of the current subject matter;

FIG. 64 shows a perspective view of a heating element in a bent position consistent with implementations of the current subject matter;

FIG. 65 shows a side view of a heating element in a bent position consistent with implementations of the current subject matter;

FIG. 68A shows a top perspective view of an atomizer assembly consistent with implementations of the current subject matter;

FIG. 69 shows a bottom perspective view of an atomizer assembly consistent with implementations of the current subject matter;

FIG. 70 shows an exploded perspective view of an atomizer assembly consistent with implementations of the current subject matter;

DETAILED DESCRIPTION

Figure 3:
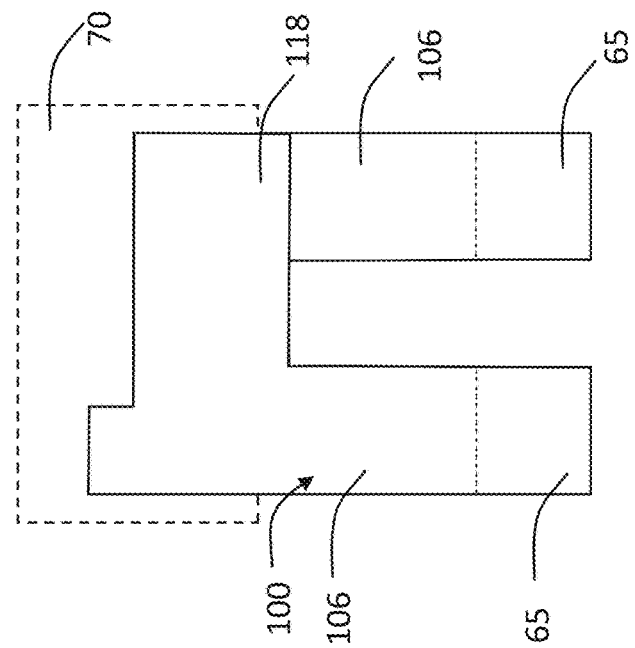
FIG. 3 shows a schematic view of a heating element for use in a vaporizer device consistent with implementations of the current subject matter.

Implementations of the current subject matter include devices relating to vaporizing of one or more materials for inhalation by a user. Examples of vaporizers consistent with implementations of the current subject matter include electronic vaporizers, electronic cigarettes, e-cigarettes, or the like.

The vaporizable material used with a vaporizer may optionally be provided within a cartridge (e.g., a part of the vaporizer that contains the vaporizable material in a reservoir or other container and that can be refillable when empty or disposable in favor of a new cartridge containing additional vaporizable material of a same or different type). A vaporizer may be a cartridge-using vaporizer, a cartridge-less vaporizer, or a multi-use vaporizer capable of use with or without a cartridge. For example, a multi-use vaporizer may include a heating chamber (e.g., an oven) configured to receive a vaporizable material directly in the heating chamber and also to receive a cartridge or other replaceable device having a reservoir, a volume, or the like for at least partially containing a usable amount of vaporizable material. In various implementations, a vaporizer may be configured for use with liquid vaporizable material (e.g., a carrier solution in which an active and/or inactive ingredient(s) are suspended or held in solution or a neat liquid form of the vaporizable material itself) or a solid vaporizable material. Some vaporizers consistent with this disclosure may be capable of use with both solid and liquid vaporizable material. A solid vaporizable material may include a plant material that emits some part of the plant material as the vaporizable material (e.g., such that some part of the plant material remains as waste after the vaporizable material is emitted for inhalation by a user) or optionally can be a solid form of the vaporizable material itself (e.g., a "wax") such that all of the solid material can eventually be vaporized for inhalation. A liquid vaporizable material can likewise be capable of being completely vaporized or can include some part of the liquid material that remains after all of the material suitable for inhalation has been consumed.

Referring to the block diagram of FIG. 1A, a vaporizer 10 typically includes a power source 8 (such as a battery which may be a rechargeable battery), and a controller 19 (e.g., a processor, circuitry, etc. capable of executing logic) for controlling delivery of heat to an atomizer 26 (also referred to herein as an "atomizer assembly") to cause a vaporizable material to be converted from a condensed form (e.g., a solid, a liquid, a solution, a suspension, a part of an at least partially unprocessed plant material, etc.) to the gas phase. The controller 19 may be part of one or more printed circuit boards (PCBs) consistent with certain implementations of the current subject matter. After conversion of the vaporizable material to the gas phase, and depending on the type of vaporizer, the physical and chemical properties of the vaporizable material, and/or other factors, at least some of the gas-phase vaporizable material may condense to form particulate matter in at least a partial local equilibrium with the gas phase as part of an aerosol, which can form some or all of an inhalable dose provided by the vaporizer 10 for a given puff or draw on the vaporizer. It will be understood that the interplay between gas and condensed phases in an aerosol generated by a vaporizer can be complex and dynamic, as factors such as ambient temperature, relative humidity, chemistry, flow conditions in airflow paths (both inside the vaporizer and in the airways of a human or other animal), mixing of the gas-phase or aerosol-phase vaporizable material with other air streams, etc., may affect one or more physical parameters of an aerosol. In some vaporizers, and particularly for vaporizers for delivery of more volatile vaporizable materials, the inhalable dose may exist predominantly in the gas phase (i.e., formation of condensed phase particles may be very limited). In other examples, the converse may be true.

Vaporizers for use with liquid vaporizable materials (e.g., neat liquids, suspensions, solutions, mixtures, etc.) typically include an atomizer 26 in which a wicking element (also referred to herein as a wick (not shown in FIG. 1A), which can include any component (e.g., a fibrous wick, a sintered material, a structure having a narrow gap or channel between surfaces wettable by a liquid vaporizable material) capable of drawing liquid from a reservoir or fluid storage component under capillary pressure), conveys an amount of a liquid vaporizable material to a part of the atomizer that includes a heating element (also not shown in FIG. 1A). The wicking element is generally configured to draw liquid vaporizable material from a reservoir configured to contain (and that may in use contain) the liquid vaporizable material such that the liquid vaporizable material may be vaporized by heat delivered from a heating element. The wicking element may also optionally allow air to enter the reservoir to replace the volume of liquid removed. In other words, capillary action pulls liquid vaporizable material into the wick for vaporization by the heating element (described below), and air may, in some implementations of the current subject matter, return to the reservoir through the wick to at least partially equalize pressure in the reservoir. However, as vaporizable material is drawn out of the reservoir, the pressure inside the reservoir is reduced, thereby creating a vacuum and acting against the capillary action. This can reduce the effectiveness of the wick to draw the vaporizable material into the atomizer, thereby reducing the effectiveness of the vaporization device to vaporize a desired amount of vaporizable material, such as when a user takes a puff on the vaporizer device. Furthermore, the vacuum created in the reservoir can ultimately result in the inability to draw all of the vaporizable material into the atomizer, thereby wasting vaporizable material. As such, improved vaporization devices and/or vaporization cartridges that improve upon or overcome these issues is desired. Other approaches to allowing air back into the reservoir to equalize pressure are also within the scope of the current subject matter.

The heating element can be or include one or more of a conductive heater, a radiative heater, and a convective heater. One type of heating element is a resistive heating element, which can be constructed of or at least include a material (e.g., a metal or alloy, for example a nickel-chromium alloy, or a non-metallic resistor) configured to dissipate electrical power in the form of heat when electrical current is passed through one or more resistive segments of the heating element. In some implementations of the current subject matter, an atomizer can include a heating element that includes a resistive coil or other heating element wrapped around, positioned within, integrated into a bulk shape of, pressed into thermal contact with, or otherwise arranged to deliver heat to a wicking element to cause a liquid vaporizable material drawn by the wicking element from a reservoir to be vaporized for subsequent inhalation by a user in a gas and/or a condensed (e.g., aerosol particles or droplets) phase. Other wicking element, heating element, and/or atomizer assembly configurations are also possible, as discussed further below. For example, a heating element consistent with implementations of the current subject matter may desirably be shaped to receive a wicking element and/or crimped or pressed at least partially around the wicking element. The heating element may be bent such that the heating element is configured to secure the wicking element between at least two or three portions of the heating element. The heating element may be bent to conform to a shape of at least a portion of the wicking element. The heating element may be more easily manufacturable than typical heating elements. The heating element consistent with implementations of the current subject matter may also be made of an electrically conductive metal suitable for resistive heating and in some implementations, the heating element may include selective plating of another material to allow the heating element (and thus, the vaporizable material) to be more efficiently heated.

Certain vaporizers may also or alternatively be configured to create an inhalable dose of gas-phase and/or aerosol-phase vaporizable material via heating of a non-liquid vaporizable material, such as for example a solid-phase vaporizable material (e.g., a wax or the like) or plant material (e.g., tobacco leaves and/or parts of tobacco leaves) containing the vaporizable material. In such vaporizers, a resistive heating element may be part of or otherwise incorporated into or in thermal contact with the walls of an oven or other heating chamber into which the non-liquid vaporizable material is placed. Alternatively, a resistive heating element or elements may be used to heat air passing through or past the non-liquid vaporizable material to cause convective heating of the non-liquid vaporizable material. In still other examples, a resistive heating element or elements may be disposed in intimate contact with plant material such that direct conductive heating of the plant material occurs from within a mass of the plant material (e.g., as opposed to only by conduction inward from walls of an oven).

The heating element may be activated (e.g., a controller, which is optionally part of a vaporizer body as discussed below, may cause current to pass from the power source through a circuit including the resistive heating element, which is optionally part of a vaporizer cartridge as discussed below), in association with a user puffing (e.g., drawing, inhaling, etc.) on a mouthpiece 21 of the vaporizer to cause air to flow from an air inlet, along an airflow path that passes an atomizer (e.g., one or more wicking elements and one or more heating elements in combination), optionally through one or more condensation areas or chambers, to an air outlet in the mouthpiece. Incoming air passing along the airflow path passes over, around, through, etc., the atomizer, where gas phase vaporizable material is entrained into the air. As noted above, the entrained gas-phase vaporizable material may condense as it passes through the remainder of the airflow path such that an inhalable dose of the vaporizable material in an aerosol form can be delivered from the air outlet (e.g., in a mouthpiece 21 for inhalation by a user).

Activation of the heating element may be caused by automatic detection of the puff based on one or more of signals generated by one or more sensors 29, such as for example a pressure sensor or sensors disposed to detect pressure along the airflow path relative to ambient pressure (or optionally to measure changes in absolute pressure), one or more motion sensors of the vaporizer, one or more flow sensors of the vaporizer, and/or a capacitive lip sensor of the vaporizer; in response to detection of interaction of a user with one or more input devices 41 (e.g., buttons or other tactile control devices of the vaporizer 10), receipt of one or more signals from a computing device in communication with the vaporizer; and/or via other approaches for determining that a puff is occurring or imminent.

As alluded to in the previous paragraph, a vaporizer consistent with implementations of the current subject matter may be configured to connect (e.g., wirelessly or via a wired connection) to a computing device (or optionally two or more devices) in communication with the vaporizer. To this end, the controller 19 may include communication hardware 49. The controller may also include a memory 43. A computing device can be a component of a vaporizer system that also includes the vaporizer 10, and can include its own communication hardware, which can establish a wireless communication channel with the communication hardware 49 of the vaporizer 10. For example, a computing device used as part of a vaporizer system may include a general purpose computing device (e.g., a smartphone, a tablet, a personal computer, some other portable device such as a smartwatch, or the like) that executes software to produce a user interface for enabling a user of the device to interact with a vaporizer. In other implementations of the current subject matter, such a device used as part of a vaporizer system can be a dedicated piece of hardware such as a remote control or other wireless or wired device having one or more physical or soft (e.g., configurable on a screen or other display device and selectable via user interaction with a touch-sensitive screen or some other input device like a mouse, pointer, trackball, cursor buttons, or the like) interface controls. The vaporizer can also include one or more output 37 features or devices for providing information to the user.

A computing device that is part of a vaporizer system as defined above can be used for any of one or more functions, such as controlling dosing (e.g., dose monitoring, dose setting, dose limiting, user tracking, etc.), controlling sessioning (e.g., session monitoring, session setting, session limiting, user tracking, etc.), controlling nicotine delivery (e.g., switching between nicotine and non-nicotine vaporizable material, adjusting an amount of nicotine delivered, etc.), obtaining locational information (e.g., location of other users, retailer/commercial venue locations, vaping locations, relative or absolute location of the vaporizer itself, etc.), vaporizer personalization (e.g., naming the vaporizer, locking/password protecting the vaporizer, adjusting one or more parental controls, associating the vaporizer with a user group, registering the vaporizer with a manufacturer or warranty maintenance organization, etc.), engaging in social activities (e.g., games, social media communications, interacting with one or more groups, etc.) with other users, or the like. The terms "sessioning", "session", "vaporizer session," or "vapor session," are used generically to refer to a period devoted to the use of the vaporizer. The period can include a time period, a number of doses, an amount of vaporizable material, and/or the like.

In the example in which a computing device provides signals related to activation of the resistive heating element, or in other examples of coupling of a computing device with a vaporizer for implementation of various control or other functions, the computing device executes one or more computer instructions sets to provide a user interface and underlying data handling. In one example, detection by the computing device of user interaction with one or more user interface elements can cause the computing device to signal the vaporizer 10 to activate the heating element, either to a full operating temperature for creation of an inhalable dose of vapor/aerosol or to a lower temperature to begin heating the heating element. Other functions of the vaporizer may be controlled by interaction of a user with a user interface on a computing device in communication with the vaporizer.

The temperature of a resistive heating element of a vaporizer may depend on a number of factors, including a material of the heating element, an amount of electrical power delivered to the resistive heating element and/or a duty cycle at which the electrical power is delivered, conductive heat transfer to other parts of the electronic vaporizer and/or to the environment, latent heat losses due to vaporization of a vaporizable material from the wicking element and/or the atomizer as a whole, and convective heat losses due to airflow (e.g., air moving across the heating element or the atomizer as a whole when a user inhales on the electronic vaporizer). As noted above, to reliably activate the heating element or heat the heating element to a desired temperature, a vaporizer may, in some implementations of the current subject matter, make use of signals from a pressure sensor to determine when a user is inhaling. The pressure sensor can be positioned in the airflow path and/or can be connected (e.g., by a passageway or other path) to an airflow path connecting an inlet for air to enter the device and an outlet via which the user inhales the resulting vapor and/or aerosol such that the sensor experiences pressure changes concurrently with air passing through the vaporizer device from the air inlet to the air outlet. In some implementations of the current subject matter, the heating element may be activated in association with a user's puff, for example by automatic detection of the puff, for example by the pressure sensor detecting a pressure change in the airflow path. As noted above, the heating element may be entirely and/or selectively plated with one or more other materials to enhance heating performance of the heating element.

Typically, the pressure sensor (and/or any other sensors 29) can be positioned on or coupled (e.g., electrically or electronically connected, either physically or via a wireless connection) to the controller 19 (e.g., a printed circuit board assembly or other type of circuit board). To take measurements accurately and maintain durability of the vaporizer, it can be beneficial to provide a resilient seal 60 to separate an airflow path from other parts of the vaporizer. The seal 60, which can be a gasket, may be configured to at least partially surround the pressure sensor such that connections of the pressure sensor to internal circuitry of the vaporizer are separated from a part of the pressure sensor exposed to the airflow path.

In an example of a cartridge-based vaporizer, the seal or gasket 60 may also separate parts of one or more electrical connections between a vaporizer body 50 and a vaporizer cartridge 52. Such arrangements of a gasket or seal 60 in a vaporizer 10 can be helpful in mitigating against potentially disruptive impacts on vaporizer components resulting from interactions with environmental factors such as water in the vapor or liquid phases, other fluids such as the vaporizable material, etc., and/or to reduce escape of air from the designed airflow path in the vaporizer. Unwanted air, liquid or other fluid passing over and/or contacting circuitry of the vaporizer can cause various unwanted effects, such as altered pressure readings, and/or can result in the buildup of unwanted material, such as moisture, the vaporizable material, etc., in parts of the vaporizer where they may result in poor pressure signal, degradation of the pressure sensor or other components, and/or a shorter life of the vaporizer. Leaks in the seal or gasket 60 can also result in a user inhaling air that has passed over parts of the vaporizer device containing or constructed of materials that may not be desirable to be inhaled.

A general class of vaporizers that have recently gained popularity includes a vaporizer body 50 that includes a controller 19, a power source 8 (e.g., battery), one or more sensors, charging contacts, a gasket or seal 60, and a cartridge receptacle 69 configured to receive a vaporizer cartridge 52 for coupling with the vaporizer body 50 through one or more of a variety of attachment structures. In some examples, vaporizer cartridge 52 includes a reservoir 55 for containing a liquid vaporizable material and a mouthpiece 21 for delivering an inhalable dose to a user. The vaporizer cartridge can include an atomizer 26 having a wicking element and a heating element, or alternatively, one or both of the wicking element and the heating element can be part of the vaporizer body 50. In implementations in which any part of the atomizer 26 (e.g., heating element and/or wicking element) is part of the vaporizer body 50, the vaporizer can be configured to supply liquid vaporizable material from a reservoir in the vaporizer cartridge to the atomizer part(s) included in the vaporizer body.

Cartridge-based configurations for vaporizers that generate an inhalable dose of a non-liquid vaporizable material via heating of a non-liquid vaporizable material are also within the scope of the current subject matter. For example, a vaporizer cartridge may include a mass of a plant material that is processed and formed to have direct contact with parts of one or more resistive heating elements, and such a vaporizer cartridge may be configured to be coupled mechanically and electrically to a vaporizer body that includes a processor, a power source, and electrical contacts for connecting to corresponding cartridge contacts for completing a circuit with the one or more resistive heating elements.

In vaporizers in which the power source 8 is part of a vaporizer body 50 and a heating element is disposed in a vaporizer cartridge 52 configured to couple with the vaporizer body 50, the vaporizer 10 may include electrical connection features (e.g., means for completing a circuit) for completing a circuit that includes the controller (e.g., a printed circuit board, a microcontroller, or the like), the power source, and the heating element. These features may include at least two, four, or more contacts on a bottom, side, internal, external, or other surface of the vaporizer cartridge 52 (referred to herein as cartridge contacts 65) and at least two, four, or more contacts disposed near a base of the cartridge receptacle (referred to herein as receptacle contacts 62) of the vaporizer 10 such that the cartridge contacts 65 and the receptacle contacts 62 make electrical connections when the vaporizer cartridge 52 is inserted into and coupled with the cartridge receptacle 69.

In some implementations, at least a portion of the cartridge contacts 65 may face a direction that is approximately perpendicular to the bottom surface of the vaporizer cartridge. For example, at least a portion of the cartridge contacts 65 may be approximately parallel to sides of the vaporizer cartridge and/or may face outwardly towards lateral sides of the vaporizer cartridge. In such configurations, the cartridge contacts 65 may either be exposed and accessible external to an outer shell of the vaporizer cartridge and/or be positioned within a portion of the vaporizer cartridge, such as within an outer shell of the vaporizer cartridge. For example, the cartridge contacts 65 may face an interior wall of the outer shell of the vaporizer cartridge or another portion of the vaporizer cartridge. The receptacle contacts 62 of the vaporizer 10 may pass into a portion of the vaporizer cartridge, such as the outer shell of the vaporizer cartridge to electrically connect with the cartridge contacts 65 when the vaporizer cartridge 52 is inserted into and coupled with the cartridge receptacle 69. In some implementation, when the vaporizer cartridge 52 is inserted into and coupled with the cartridge receptacle 69, the receptacle contacts 65 may be positioned between a portion of the vaporizer cartridge 52 (e.g., the outer shell of the vaporizer cartridge) and the cartridge contacts 65. Thus, at least a portion of the vaporizer cartridge 52, such as near a base of the vaporizer cartridge 52, may include a female portion that receives at least a portion of the cartridge receptacle 69 that includes the receptacle contacts 62 such that the cartridge contacts 65 and the receptacle contacts 62 mate within at least a portion of the vaporizer cartridge 52.

The cartridge contacts 65 and/or the receptacle contacts 62 may include one or more wiping or brush-type contacts that are configured to clean the connection between the contacts 65, 62 and other contacts or power source. For example, the wiping and/or brush type contacts may include two parallel, but offset, bosses that frictionally engage and slide against one another in a direction that is parallel or perpendicular to the insertion direction. The cartridge contacts 65, as explained below, may form a portion of the heating element of the vaporizer cartridge. The circuit completed by these electrical connections between the cartridge contacts 65 and the receptacle contacts 62 can allow delivery of electrical current to the resistive heating element and may further be used for additional functions, such as for example for measuring a resistance of the resistive heating element for use in determining and/or controlling a temperature of the resistive heating element based on a thermal coefficient of resistivity of the resistive heating element, for identifying a cartridge based on one or more electrical characteristics of a resistive heating element or the other circuitry of the vaporizer cartridge, etc.

In some examples of the current subject matter, the cartridge contacts and the receptacle contacts can be configured to electrically connect in either of at least two orientations. In other words, one or more circuits necessary for operation of the vaporizer can be completed by insertion of a vaporizer cartridge 52 in the cartridge receptacle 69 in a first rotational orientation (around an axis along which the end of the vaporizer cartridge 52 having the cartridge contacts 65 is inserted into the cartridge receptacle 69 of the vaporizer body 50 and/or at least a portion of the cartridge receptacle 69 having the receptacle contacts 62 is inserted into at least a portion of the vaporizer cartridge 52 having the cartridge contacts 65) such that a first cartridge contact of the cartridge contacts 65 is electrically connected to a first receptacle contact of the receptacle contacts 62, a second cartridge contact opposite the first cartridge contact of the cartridge contacts 65 is electrically connected to a second receptacle contact of the receptacle contacts 62, and so on. Furthermore, the one or more circuits necessary for operation of the vaporizer can be completed by insertion of a vaporizer cartridge 52 in the cartridge receptacle 69 in a second rotational orientation such that the first cartridge contact is electrically connected to the second receptacle contact and the second cartridge contact is electrically connected to the first receptacle contact. This feature of a vaporizer cartridge 52 being reversibly insertable into a cartridge receptacle 69 of the vaporizer body 50 is described further below. For example, the cartridge contacts 65 and the receptacle contacts 62 may mate, such as face-to-face, or as interlocking, with one another. In some implementations, the one or more cartridge and/or receptacle contacts 65, 62 can include angled or shaped surfaces, which are symmetrical, so as to be able to mate with one another in any one of two reversible orientations.

In one example of an attachment structure for coupling a vaporizer cartridge 52 to a vaporizer body, the vaporizer body 50 includes a detent (e.g., a dimple, protrusion, spring, etc.) protruding inwardly from an inner surface the cartridge receptacle 69. One or more exterior surfaces (e.g., surfaces positioned along an exterior of the vaporizer cartridge or an externally accessible surface positioned within the vaporizer cartridge) of the vaporizer cartridge 52 can include corresponding recesses (not shown in FIG. 1A) that can fit, receive, and/or otherwise snap over such detents when an end of the vaporizer cartridge 52 is inserted into the cartridge receptacle 69 on the vaporizer body 50. When the vaporizer cartridge 52 and the vaporizer body 50 are coupled (e.g., by insertion of an end of the vaporizer cartridge 52 into the cartridge receptacle 69 of the vaporizer body 50), the detent in the vaporizer body 50 may fit within and/or otherwise be held within the recesses of the vaporizer cartridge 52 to hold the vaporizer cartridge 52 in place when assembled. Such a detent-recess assembly can provide enough support to hold the vaporizer cartridge 52 in place to ensure good contact between the at least two cartridge contacts 65 and the at least two receptacle contacts 62, while allowing release of the vaporizer cartridge 52 from the vaporizer body 50 when a user pulls with reasonable force on the vaporizer cartridge 52 to disengage the vaporizer cartridge 52 from the cartridge receptacle 69.

Further to the discussion above about the electrical connections between a vaporizer cartridge and a vaporizer body 50 being reversible such that at least two rotational orientations of the vaporizer cartridge 52 in the cartridge receptacle 69 are possible, in some vaporizers the shape of the vaporizer cartridge 52, or at least a shape of the end of the vaporizer cartridge that is configured for insertion into the cartridge receptacle 69 may have rotational symmetry of at least order two. In other words, the vaporizer cartridge 52 or at least the insertable end of the vaporizer cartridge 52 may be symmetric upon a rotation of 180° around an axis along which the vaporizer cartridge 52 is inserted into the cartridge receptacle 69. In such a configuration, the circuitry of the vaporizer may support identical operation regardless of which symmetrical orientation of the vaporizer cartridge 52 occurs.

In some examples, the vaporizer cartridge 52, or at least an end of the vaporizer cartridge 52 configured for insertion in the cartridge receptacle 69 may have a non-circular cross-section transverse to the axis along which the vaporizer cartridge 52 is inserted into the cartridge receptacle 69. For example, the non-circular cross-section may be approximately rectangular, approximately elliptical (e.g., have an approximately oval shape), non-rectangular but with two sets of parallel or approximately parallel opposing sides (e.g., having a parallelogram-like shape), or other shapes having rotational symmetry of at least order two. In this context, approximately having a shape indicates that a basic likeness to the described shape is apparent, but that sides of the shape in question need not be completely linear and vertices need not be completely sharp. Rounding of both or either of edges or vertices of the cross-sectional shape is contemplated in the description of any non-circular cross-section referred to herein.

The at least two cartridge contacts 65 and the at least two receptacle contacts 62 can take various forms. For example, one or both sets of contacts may include conductive pins, tabs, posts, receiving holes for pins or posts, or the like. Some types of contacts may include springs or other urging features to cause better physical and electrical contact between the contacts on the vaporizer cartridge and the vaporizer body. The electrical contacts may optionally be gold-plated, and/or can include other materials.

FIG. 1B illustrates an embodiment of the vaporizer body 50 having a cartridge receptacle 69 into which the vaporizer cartridge 52 may be releasably inserted. FIG. 1B shows a top view of the vaporization device 10 illustrating the cartridge being positioned for insertion into the vaporizer body 50. When a user puffs on the vaporization device 10, air may pass between an outer surface of the vaporizer cartridge 52 and an inner surface of a cartridge receptacle 69 on the vaporizer body 50. Air can then be drawn into an insertable end 3 of the cartridge, through the vaporization chamber that includes or contains the heating element and wick, and out through an outlet of the mouthpiece 21 for delivery of the inhalable aerosol to a user. The reservoir 55 of the vaporizer cartridge 52 may be formed in whole or in part from translucent material such that a level of vaporizable material 2 is visible along the vaporizer cartridge 52. FIG. 1C illustrates example features that can be included in embodiments of the vaporizer device 10 consistent with implementations of the current subject matter. For example, FIG. 1C shows a top view of an example of the vaporizer device 10 after connecting the vaporizer cartridge 52 to the vaporizer body 50. FIG. 1D illustrates an exploded view of an embodiment of the vaporizer cartridge 52, FIG. 1E illustrates a perspective view of an embodiment of the vaporizer cartridge 52, and FIG. 1F illustrates a bottom perspective view of an embodiment of the vaporizer cartridge 52. As shown in FIGS. 1D-1F, the vaporizer cartridge 52 includes a housing 7 and an atomizer assembly (or the atomizer) 26.

The atomizer assembly 26 (see FIGS. 56-58) may include a wicking element 70, a heating element 100, and a wick housing 98. As explained in more detail below, at least a portion of the heating element 100 is positioned between the housing 7 and the wick housing 98 and is exposed to be coupled with a portion of the vaporizer body 50 (e.g., electrically coupled with the receptacle contacts 62). The wick housing 98 may include four sides. For example, the wick housing 98 may include two opposing short sides and two opposing long sides. The two opposing long sides may each include at least one (two or more) recess 87 (see FIGS. 56, 68A). The recesses 87 may be positioned along the long side of the wick housing 98 and adjacent to respective intersections between the long sides and the short sides of the wick housing 98. The recesses 87 may be shaped to releasably couple with a corresponding feature (e.g., a spring) on the vaporizer body 50 to secure the vaporizer cartridge 52 to the vaporizer body 50 within the cartridge receptacle 69. The recesses 87 provides a mechanically stable securement means to couple the vaporizer cartridge 52 to the vaporizer body 50.

In some implementations, the wick housing 98 also includes an identification chip 95, which may be configured to communicate with a corresponding chip reader located on the vaporizer. The identification chip 95 may be glued and/or otherwise adhered to the wick housing 98, such as on a short side of the wick housing 98. The wick housing 98 may additionally or alternatively include a chip recess 83 (see FIG. 57) that is configured to receive the identification chip 95. The chip recess 83 may be surrounded by two, four, or more walls. The chip recess 83 may be shaped to secure the identification chip 95 to the wick housing 98.

As noted above, the vaporizer cartridge 52 may generally include a reservoir, an air path, and an atomizer 26. In some configurations, the heating element and/or atomizer described in accordance with implementations of the current subject matter can be implemented directly into a vaporizer body and/or may not be removable from the vaporizer body. In some implementations, the vaporizer body may not include a removable cartridge.

Various advantages and benefits of the current subject matter may relate to improvements relative to current vaporizer configurations, methods of manufacture, and the like. For example, a heating element of a vaporizer device consistent with implementations of the current subject matter may desirably be made (e.g., stamped) from a sheet of material and either crimped around at least a portion of a wicking element or bent to provide a preformed element configured to receive the wicking element (e.g., the wicking element is pushed into the heating element and/or the heating element is held in tension and is pulled over the wicking element). The heating element may be bent such that the heating element secures the wicking element between at least two or three portions of the heating element. The heating element may be bent to conform to a shape of at least a portion of the wicking element. Configurations of the heating element allows for more consistent and enhanced quality manufacturing of the heating element. Consistency of manufacturing quality of the heating element may be especially important during scaled and/or automated manufacturing processes. For example, the heating element consistent with implementations of the current subject matter helps to reduce tolerance issues that may arise during manufacturing processes when assembling a heating element having multiple components.

In some implementations, accuracy of measurements taken from the heating element (e.g., a resistance, a current, a temperature, etc.) may be improved due at least in part to the improved consistency in manufacturability of the heating element having reduced tolerance issues. Greater accuracy in measurements can provide an enhanced user experience when using the vaporizer device. For example, as mentioned above, the vaporizer 10 may receive a signal to activate the heating element, either to a full operating temperature for creation of an inhalable dose of vapor/aerosol or to a lower temperature to begin heating the heating element. The temperature of the heating element of the vaporizer may depend on a number of factors, as noted above, and several of these factors can be made more predictable by elimination of potential variations in fabrication and assembly of atomizer components. A heating element made (e.g., stamped) from a sheet of material and either crimped around at least a portion of a wicking element or bent to provide a preformed element desirably helps to minimize heat losses and helps to ensure that the heating element behaves predictably to be heated to the appropriate temperature.

Additionally, as noted above, the heating element may be entirely and/or selectively plated with one or more materials to enhance heating performance of the heating element. Plating all or a portion of the heating element may help to minimize heat losses. Plating may also help in concentrating the heated portion of the heating element in the proper location, providing a more efficiently heated heating element and further reducing heat losses. Selective plating may help to direct the current provided to the heating element to the proper location. Selective plating may also help to reduce the amount of plating material and/or costs associated with manufacturing the heating element.

Once the heating element is formed into the appropriate shape via one or more processes discussed below, the heating element may be crimped around the wicking element and/or bent into the proper position to receive the wicking element. The wicking element may, in some implementations, be a fibrous wick, formed as an at least approximately flat pad or with other cross-sectional shapes such as circles, ovals, etc. A flat pad can allow for the rate that the vaporizable material is drawn into the wicking element to be controlled more precisely and/or accurately. For example, a length, width, and/or thickness can be adjusted for optimal performance. A wicking element forming a flat pad may also provide a greater transfer surface area, which may allow for increased flow of the vaporizable material from the reservoir into the wicking element for vaporization by the heating element (in other words, larger mass transfer of vaporizable material), and from the wicking element to air flowing past it. In such configurations, the heating element may contact the wicking element in multiple directions (e.g., on at least two sides of the wicking element) to increase efficiency of the process of drawing vaporizable material into the wicking element and vaporizing the vaporizable material. The flat pad may also be more easily shaped and/or cut, and thus may be more easily assembled with the heating element. In some implementations, as discussed in more detail below, the heating element may be configured to contact the wicking element on only one side of the wicking element.

The wicking element may include one or more rigid or compressible materials, such as cotton, silica, ceramic, and/or the like. Relative to some other materials, a cotton wicking element may allow for an increased and/or more controllable flow rate of vaporizable material from the reservoir of the vaporizer cartridge into the wicking element to be vaporized. In some implementations, the wicking element forms an at least approximately flat pad that is configured to contact the heating element and/or be secured between at least two portions of the heating element. For example, the at least approximately flat pad may have at least a first pair of opposing sides that are approximately parallel to one another. In some implementations, the at least approximately flat pad may also have at least a second pair of opposing sides that are approximately parallel to one another, and approximately perpendicular to the first pair of opposing sides.

Figure 2:
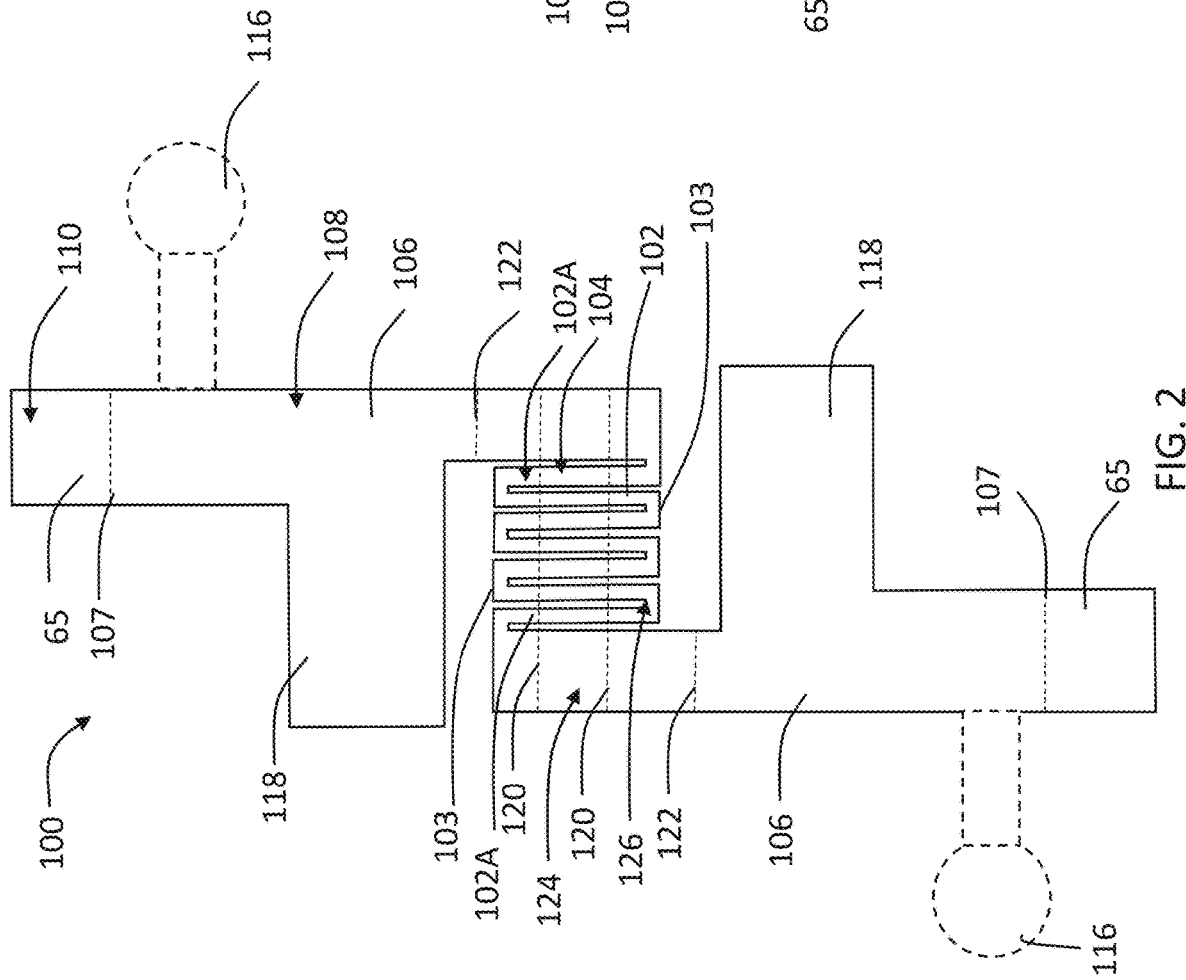
FIG. 2 shows a schematic view of a heating element for use in a vaporizer device consistent with implementations of the current subject matter.

FIGS. 2-5 illustrate schematic views of a heating element 100 consistent with implementations of the current subject matter. For example, FIG. 2 illustrates a schematic view of a heating element 100 in an unfolded position. As shown, in the unfolded position, the heating element 100 forms a planar heating element. The heating element 100 may be initially formed of a substrate material. The substrate material is then cut and/or stamped into the proper shape via various mechanical processes, including but not limited to stamping, laser cutting, photo-etching, chemical etching, and/or the like.

The substrate material may be made of an electrically conductive metal suitable for resistive heating. In some implementations, the heating element 100 includes a nickel-chromium alloy, a nickel alloy, stainless steel, and/or the like. As discussed below, the heating element 100 may be plated with a coating in one or more locations on a surface of the substrate material to enhance, limit, or otherwise alter the resistivity of the heating element in the one or more locations of the substrate material (which can be all or a portion of the heating element 100).

The heating element 100 includes one or more tines 102 (e.g., heating segments) located in a heating portion 104, one or more legs or connecting portions 106 (e.g., one, two, or more) located in a transition region 108, and a cartridge contact 65 located in an electrical contact region 110 and formed at an end portion of each of the one or more legs 106. The tines 102, the legs 106, and the cartridge contacts 65 may be integrally formed. For example, the tines 102, the legs 106, and the cartridge contacts 65 form portions of the heating element 100 that is stamped and/or cut from the substrate material. In some implementations, the heating element 100 also includes a heat shield 118 that extends from one or more of the legs 106 and also may be integrally formed with the tines 102, the legs 106, and the cartridge contacts 65.

In some implementations, at least a portion of the heating portion 104 of the heating element 100 is configured to interface with the vaporizable material drawn into the wicking element from the reservoir 55 of the vaporizer cartridge 52. The heating portion 104 of the heating element 100 may be shaped, sized, and/or otherwise treated to create a desired resistance. For example, the tines 102 located in the heating portion 104 may be designed so that the resistance of the tines 102 matches the appropriate amount of resistance to influence localized heating in the heating portion 104 to more efficiently and effectively heat the vaporizable material from the wicking element. The tines 102 form thin path heating segments or traces in series and/or in parallel to provide the desired amount of resistance.

The tines 102 (e.g., traces) may include various shapes, sizes, and configurations. In some configurations, one or more of the tines 102 may be spaced to allow the vaporizable material to be wicked out of the wicking element and from there, vaporized off side edges of each of the tines 102. The shape, length, width, composition, etc., among other properties of the tines 102 may be optimized to maximize the efficiency of generating an aerosol by vaporizing vaporizable material from within the heating portion of the heating element 100 and to maximize electrical efficiency. The shape, length, width, composition, etc., among other properties of the tines 102 may additionally or alternatively be optimized to uniformly distribute heat across the length of the tines 102 (or a portion of the tines 102, such as at the heating portion 104). For example, the width of the tines 102 may be uniform or variable along a length of the tines 102 to control the temperature profile across at least the heating portion 104 of the heating element 100. In some examples, the length of the tines 102 may be controlled to achieve a desired resistance along at least a portion of the heating element 100, such as at the heating portion 104. As shown in FIGS. 2-5, the tines 102 each have the same size and shape. For example, the tines 102 include an outer edge 103 that is approximately aligned and have a generally rectangular shape, with flat or squared outer edges 103 (see also FIGS. 6-10, and) or rounded outer edges 103 (see FIGS. 11 and 12). In some implementations, one or more of the tines 102 may include outer edges 103 that are not aligned and/or may be differently sized or shaped (see FIGS. 14-19). In some implementations, the tines 102 may be evenly spaced or have variable spacing between adjacent tines 102 (see FIGS. 44-49). The particular geometry of the tines 102 may be desirably selected to produce a particular localized resistance for heating the heating portion 104, and to maximize performance of the heating element 100 to heat the vaporizable material and generate an aerosol.

Figure 5:
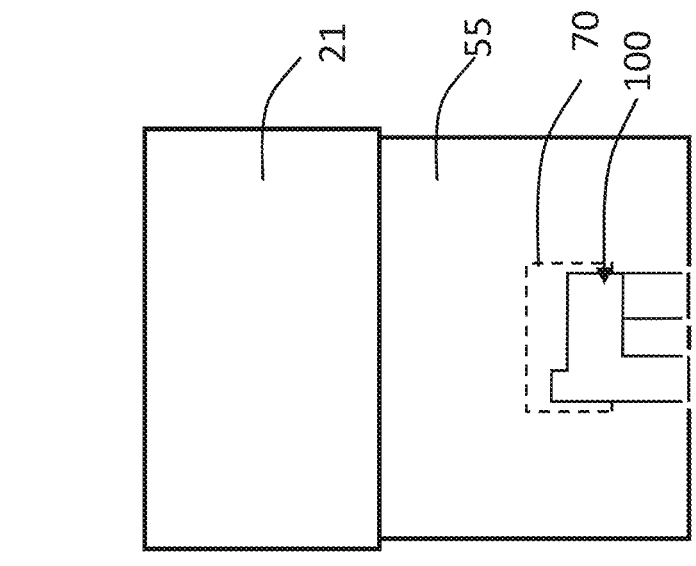
FIG. 5 shows a schematic view of a heating element positioned in a vaporizer cartridge for use in a vaporizer device consistent with implementations of the current subject matter.
Figure 4:
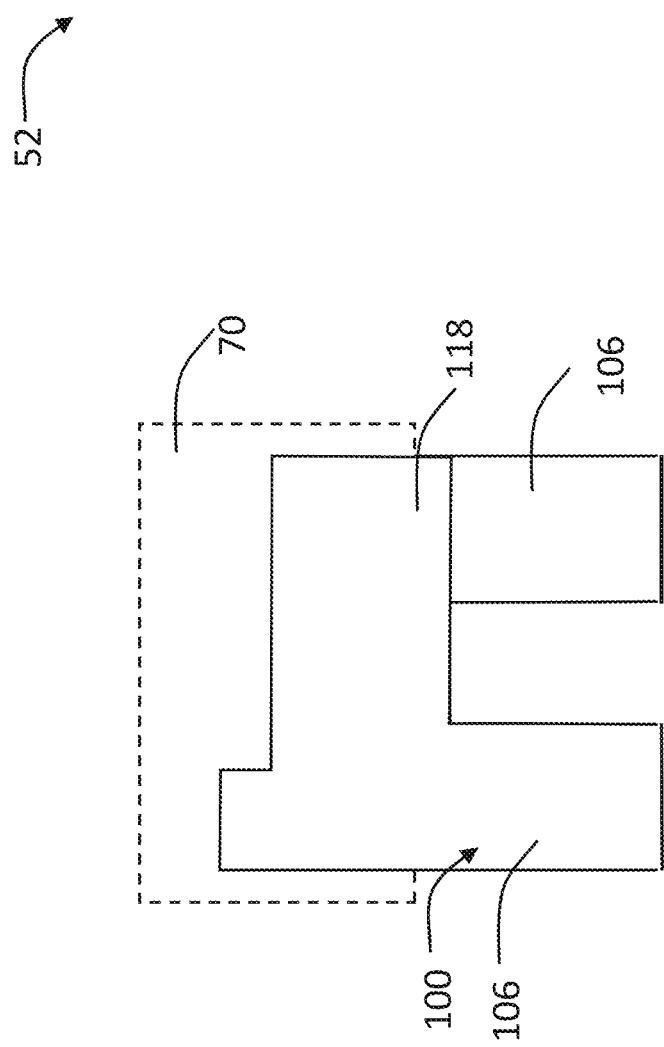
FIG. 4 shows a schematic view of a heating element for use in a vaporizer device consistent with implementations of the current subject matter.
Figure 10:
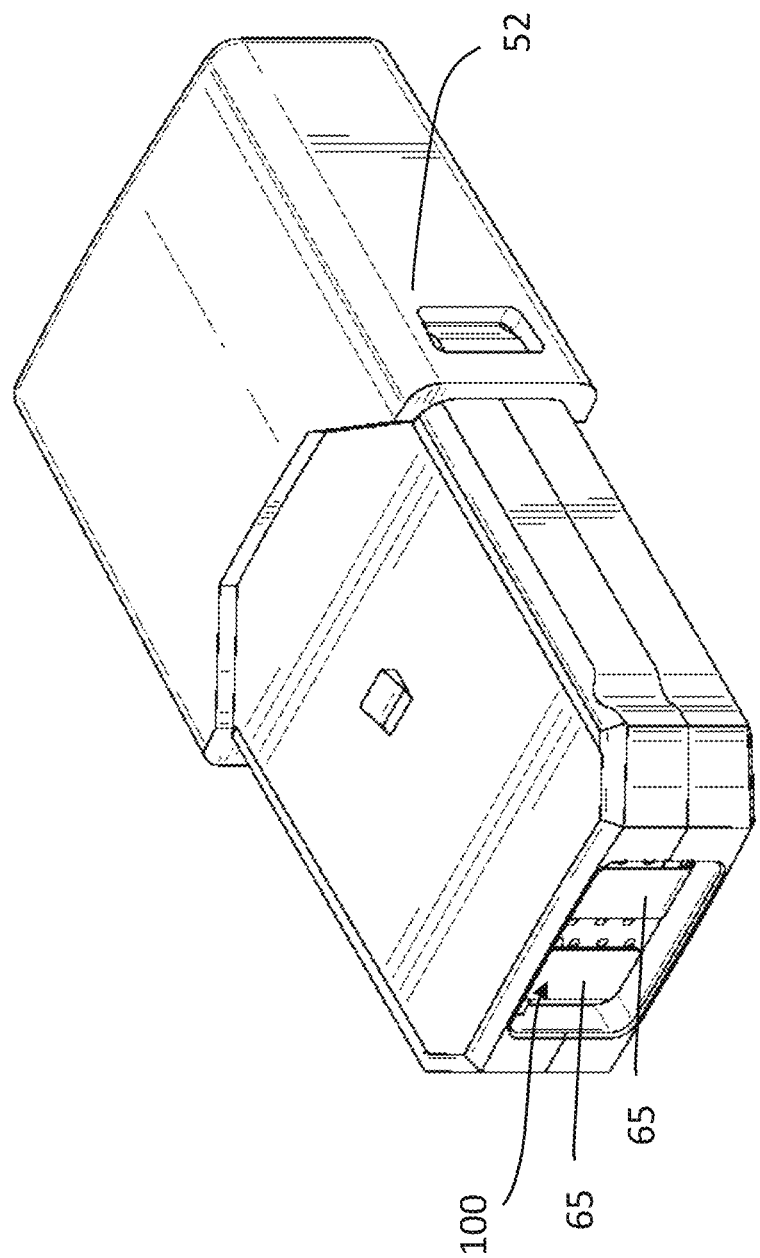
FIG. 10 shows a heating element positioned within a vaporizer cartridge consistent with implementations of the current subject matter.

The heating element 100 may include portions of wider and/or thicker geometry, and/or differing composition relative to the tines 102. These portions may form electrical contact areas and/or more conductive parts, and/or may include features for mounting the heating element 100 within the vaporizer cartridge. The legs 106 of the heating element 100 extend from an end of each outermost tine 102A. The legs 106 form a portion of the heating element 100 that has a width and/or thickness that is typically wider than a width of each of the tines 102. Though, in some implementations, the legs 106 have a width and/or thickness that is the same as or narrower than the width of each of the tines 102. The legs 106 couple the heating element 100 to the wick housing 98 or another portion of the vaporizer cartridge 52, so that the heating element 100 is at least partially or fully enclosed by the housing 7. The legs 106 provide rigidity to encourage the heating element 100 to be mechanically stable during and after manufacturing. The legs 106 also connect the cartridge contacts 65 with the tines 102 located in the heating portion 104. The legs 106 are shaped and sized to allow the heating element 100 to maintain the electrical requirements of the heating portion 104. As shown in FIG. 5, the legs 106 space the heating portion 104 from an end of the vaporizer cartridge 52 when the heating element 100 is assembled with the vaporizer cartridge 52. As discussed in more detail below, with respect to at least FIGS. 39-55 and 60-61, the legs 106 may also include a capillary feature 198, which limits or prevents fluid from flowing out of the heating portion 104 to other portions of the heating element 100.

In some implementations, one or more of the legs 106 includes one or more locating features 116. The locating features 116 may be used for relative locating of the heating element 100 or portions thereof during and/or after assembly by interfacing with other (e.g., adjacent) components of the vaporizer cartridge 52. In some implementations, the locating features 116 may be used during or after manufacturing to properly position the substrate material for cutting and/or stamping the substrate material to form the heating element 100 or post-processing of the heating element 100. The locating features 116 may be sheared off and/or cut off before crimping or otherwise bending the heating element 100.

In some implementations, the heating element 100 includes one or more heat shields 118. The heat shields 118 form a portion of the heating element 100 that extends laterally from the legs 106. When folded and/or crimped, the heat shields 118 are positioned offset in a first direction and/or a second direction opposite the first direction in the same plane from the tines 102. When the heating element 100 is assembled in the vaporizer cartridge 52, the heat shields 118 are configured to be positioned between the tines 102 (and the heating portion 104) and the body (e.g., plastic body) of the vaporizer cartridge 52. The heat shields 118 can help to insulate the heating portion 104 from the body of the vaporizer cartridge 52. The heat shields 118 help to minimize the effects of the heat emanating from the heating portion 104 on the body of the vaporizer cartridge 52 to protect the structural integrity of the body of the vaporizer cartridge 52 and to prevent melting or other deformation of the vaporizer cartridge 52. The heat shields 118 may also help to maintain a consistent temperature at the heating portion 104 by retaining heat within the heating portion 104, thereby preventing or limiting heat losses while vaporization is occurring. In some implementations, the vaporizer cartridge 52 may also or alternatively include a heat shield 118A that is separate from the heating element 100 (see FIG. 59).

As noted above, the heating element 100 includes at least two cartridge contacts 65 that form an end portion of each of the legs 106. For example, as shown in FIGS. 2-5, the cartridge contacts 65 may form the portion of the legs 106 that is folded along a fold line 107. The cartridge contacts 65 may be folded at an angle of approximately 90 degrees relative to the legs 106. In some implementations, the cartridge contacts 65 may be folded at other angles, such as at an angle of approximately 15 degrees, 25 degrees, 35 degrees, 45 degrees, 55 degrees, 65 degrees, 75 degrees or other ranges therebetween, relative to the legs 106. The cartridge contacts 65 may be folded towards or away from the heating portion 104, depending on the implementation. The cartridge contacts 65 may also be formed on another portion of the heating element 100, such as along a length of at least one of the legs 106. The cartridge contacts 65 are configured to be exposed to the environment when assembled in the vaporizer cartridge 52 (see FIG. 10).

The cartridge contacts 65 may form conductive pins, tabs, posts, receiving holes, or surfaces for pins or posts, or other contact configurations. Some types of cartridge contacts 65 may include springs or other urging features to cause better physical and electrical contact between the cartridge contacts 65 on the vaporizer cartridge and receptacle contacts 62 on the vaporizer body 50. In some implementations, the cartridge contacts 65 include wiping contacts that are configured to clean the connection between the cartridge contacts 65 and other contacts or power source. For example, the wiping contacts would include two parallel, but offset, bosses that frictionally engage and slide against one another in a direction that is parallel or perpendicular to the insertion direction.

The cartridge contacts 65 are configured to interface with the receptacle contacts 62 disposed near a base of the cartridge receptacle of the vaporizer 10 such that the cartridge contacts 65 and the receptacle contacts 62 make electrical connections when the vaporizer cartridge 52 is inserted into and coupled with the cartridge receptacle 69. The cartridge contacts 65 may electrically communicate with the power source 8 of the vaporizer device (such as via the receptacle contacts 62, etc.). The circuit completed by these electrical connections can allow delivery of electrical current to the resistive heating element to heat at least a portion of the heating element 100 and may further be used for additional functions, such as for example for measuring a resistance of the resistive heating element for use in determining and/or controlling a temperature of the resistive heating element based on a thermal coefficient of resistivity of the resistive heating element, for identifying a cartridge based on one or more electrical characteristics of a resistive heating element or the other circuitry of the vaporizer cartridge, etc. The cartridge contacts 65 may be treated, as explained in more detail below, to provide improved electrical properties (e.g., contact resistance) using, for example, conductive plating, surface treatment, and/or deposited materials.

In some implementations, the heating element 100 may be processed through a series of crimping and/or bending operations to shape the heating element 100 into a desired three-dimensional shape. For example, the heating element 100 may be preformed to receive or crimped about a wicking element 70 to secure the wicking element between at least two portions (e.g., approximately parallel portions) of the heating element 100 (such as between opposing portions of the heating portion 104). To crimp the heating element 100, the heating element 100 may be bent along fold lines 120 towards one another. Folding the heating element 100 along fold lines 120 forms a platform tine portion 124 defined by the region between the fold lines 120 and side tine portions 126 defined by the region between the fold lines 120 and the outer edges 103 of the tines 102. The platform tine portion 124 is configured to contact one end of the wicking element 70. The side tine portions 126 are configured to contact opposite sides of the wicking element 70. The platform tine portion 124 and the side tine portions 126 form a pocket that is shaped to receive the wicking element 70 and/or conform to the shape of at least a portion of the wicking element 70. The pocket allows the wicking element 70 to be secured and retained by the heating element 100 within the pocket. The platform tine portion 124 and the side tine portions 126 contact the wicking element 70 to provide a multi-dimensional contact between the heating element 100 and the wicking element 70. Multi-dimensional contact between the heating element 100 and the wicking element 70 provides for a more efficient and/or faster transfer of the vaporizable material from the reservoir 55 of the vaporizer cartridge 52 to the heating portion 104 (via the wicking element 70) to be vaporized.

In some implementations, portions of the legs 106 of the heating element 100 may also be bent along fold lines 122 away from one another. Folding the portions of the legs 106 of the heating element 100 along fold lines 122 away from one another locates the legs 106 at a position spaced away from the heating portion 104 (and tines 102) of the heating element 100 in a first and/or second direction opposite the first direction (e.g., in the same plane). Thus, folding the portions of the legs 106 of the heating element 100 along fold lines 122 away from one another spaces the heating portion 104 from the body of the vaporizer cartridge 52. FIG. 3 illustrates a schematic of the heating element 100 that has been folded along the fold lines 120 and fold lines 122 about the wicking element 70. As shown in FIG. 3, the wicking element is positioned within the pocket formed by folding the heating element 100 along fold lines 120 and 122.

In some implementations, the heating element 100 may also be bent along fold lines 123. For example, the cartridge contacts 65 may be bent towards one another (into and out of the page shown in FIG. 4) along the fold lines 123. The cartridge contacts 65 may be exposed to the environment to contact the receptacle contacts, while the remaining portions of the heating element 100 are positioned within the vaporizer cartridge 52 (see FIGS. 5 and 10).

In use, when a user puffs on the mouthpiece 21 of the vaporizer cartridge 52 when the heating element 100 is assembled into the vaporizer cartridge 52, air flows into the vaporizer cartridge and along an air path. In association with the user puff, the heating element 100 may be activated, e.g., by automatic detection of the puff via a pressure sensor, by detection of a pushing of a button by the user, by signals generated from a motion sensor, a flow sensor, a capacitive lip sensor, and/or another approach capable of detecting that a user is taking or about to be taking a puff or otherwise inhaling to cause air to enter the vaporizer device 10 and travel at least along the air path. Power can be supplied from the vaporizer device to the heating element 100 at the cartridge contacts 65, when the heating element 100 is activated.

When the heating element 100 is activated, a temperature increase results due to current flowing through the heating element 100 to generate heat. The heat is transferred to some amount of the vaporizable material through conductive, convective, and/or radiative heat transfer such that at least a portion of the vaporizable material vaporizes. The heat transfer can occur to vaporizable material in the reservoir and/or to vaporizable material drawn into the wicking element 70 retained by the heating element 100. In some implementations, the vaporizable material can vaporize along one or more edges of the tines 102, as mentioned above. The air passing into the vaporizer device flows along the air path across the heating element 100, stripping away the vaporized vaporizable material from the heating element 100. The vaporized vaporizable material can be condensed due to cooling, pressure changes, etc., such that it exits the mouthpiece 21 as an aerosol for inhalation by a user.

As noted above, the heating element 100 may be made of various materials, such as nichrome, stainless steel, or other resistive heater materials. Combinations of two or more materials may be included in the heating element 100, and such combinations can include both homogeneous distributions of the two or more materials throughout the heating element or other configurations in which relative amounts of the two or more materials are spatially heterogeneous. For example, the tines 102 may have portions that are more resistive and thereby be designed to grow hotter than other sections of the tines or heating element 100. In some implementations, at least the tines 102 (such as within the heating portion 104) may include a material that has high conductivity and heat resistance.

The heating element 100 may be entirely or selectively plated with one or more materials. Since the heating element 100 is made of a thermally and/or electrically conductive material, such as stainless steel, nichrome, or other thermally and/or electrically conductive alloy, the heating element 100 may experience electrical or heating losses in the path between the cartridge contacts 65 and the tines 102 in the heating portion 104 of the heating element 100. To help to reduce heating and/or electrical losses, at least a portion of the heating element 100 may be plated with one or more materials to reduce resistance in the electrical path leading to the heating portion 104. In some implementations consistent with the current subject matter, it is beneficial for the heating portion 104 (e.g., the tines 102) to remain unplated, with at least a portion of the legs 106 and/or cartridge contacts 65 being plated with a plating material that reduces resistance (e.g., either or both of bulk and contact resistance) in those portions.

For example, the heating element 100 may include various portions that are plated with different materials. In another example, the heating element 100 may be plated with layered materials. Plating at least a portion of the heating element 100 helps to concentrate current flowing to the heating portion 104 to reduce electrical and/or heat losses in other portions of the heating element 100. In some implementations, it is desirable to maintain a low resistance in the electrical path between the cartridge contacts 65 and the tines 102 of the heating element 100 to reduce electrical and/or heat losses in the electrical path and to compensate for the voltage drop that is concentrated across the heating portion 104.

In some implementations, the cartridge contacts 65 may be selectively plated. Selectively plating the cartridge contacts 65 with certain materials may minimize or eliminate contact resistance at the point where the measurements are taken and the electrical contact is made between the cartridge contacts 65 and the receptacle contacts. Providing a low resistance at the cartridge contacts 65 can provide more accurate voltage, current, and/or resistance measurements and readings, which can be beneficial for accurately determining the current actual temperature of the heating portion 104 of the heating element 100.

In some implementations, at least a portion of the cartridge contacts 65 and/or at least a portion of the legs 106 may be plated with one or more outer plating materials 150. For example, at least a portion of the cartridge contacts 65 and/or at least a portion of the legs 106 may be plated with at least gold, or another material that provides low contact resistance, such as platinum, palladium, silver, copper, or the like.

Figure 36:
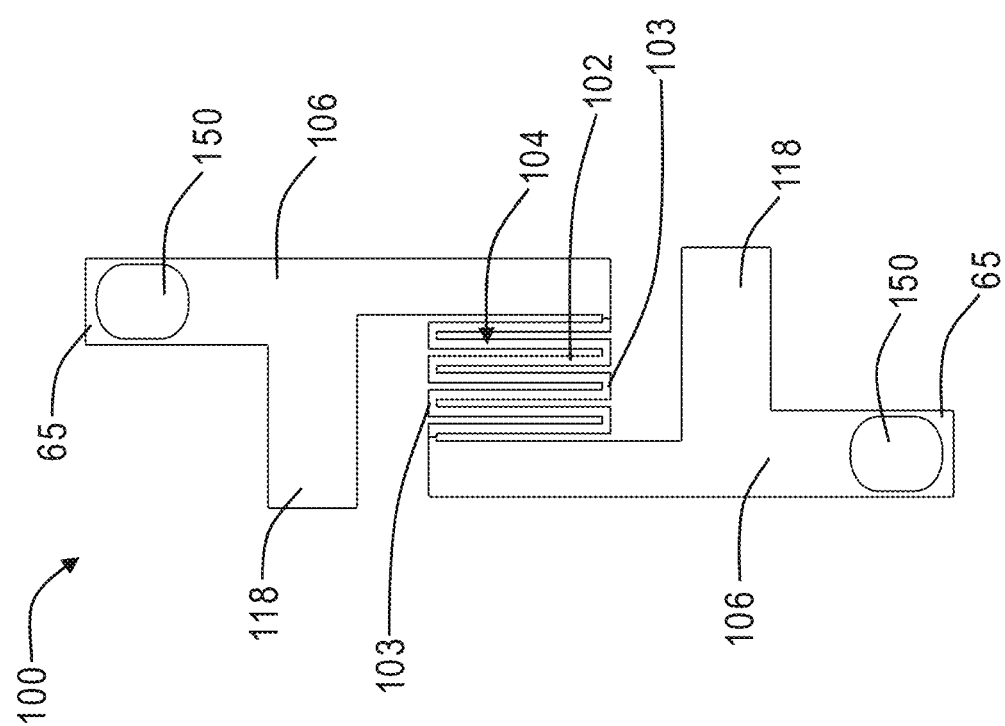
FIG. 36 shows a heating element having a plated portion, in an unbent position consistent with implementations of the current subject matter.
Figure 37:
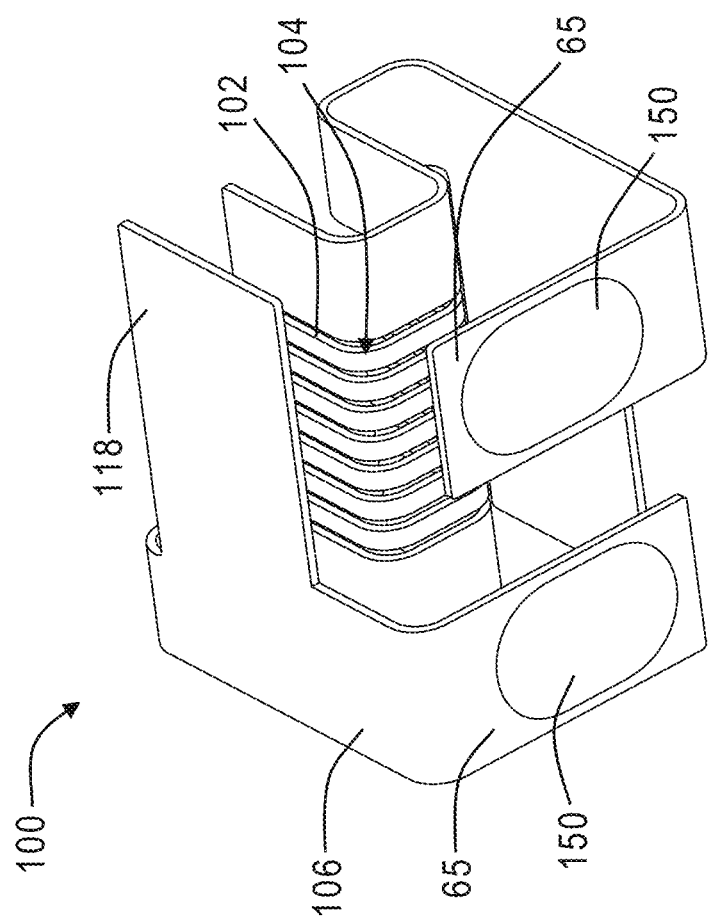
FIG. 37 shows a heating element having a plated portion, in a bent position consistent with implementations of the current subject matter.
Figure 38:
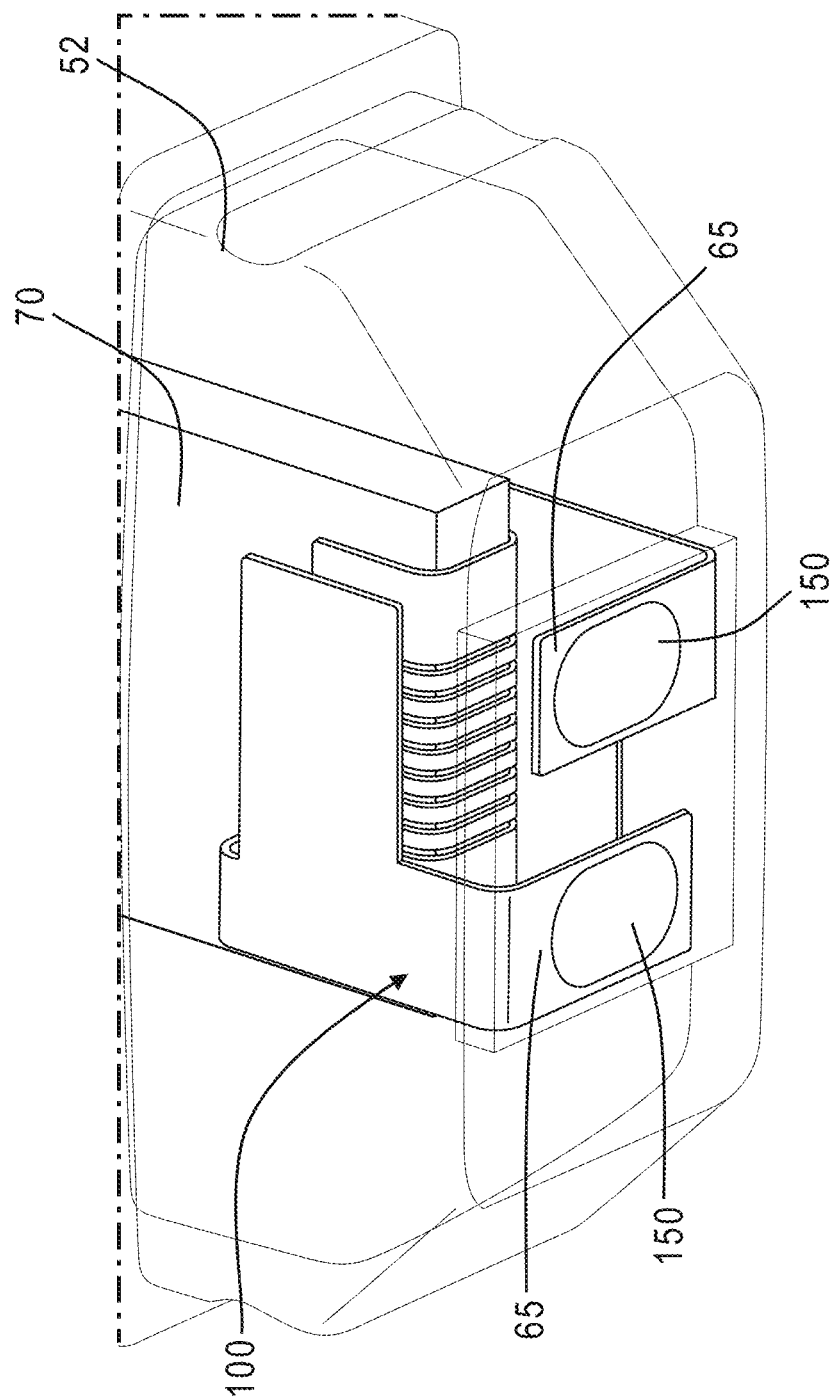
FIG. 38 shows a heating element having a plated portion positioned within a vaporizer cartridge consistent with implementations of the current subject matter.

In some implementations, in order for the low resistance outer plating material to be secured to the heating element 100, a surface of the heating element 100 may be plated with an adhering plating material. In such configurations, the adhering plating material may be deposited onto the surface of the heating element 100 and the outer plating material may be deposited onto the adhering plating material, defining first and second plating layers, respectively. The adhering plating material includes a material with adhesive properties when the outer plating material is deposited onto the adhering plating material. For example, the adhering plating material may include nickel, zinc, aluminum, iron, alloys thereof, or the like. FIGS. 36-38 illustrate examples of the heating element 100 in which the cartridge contacts 65 have been selectively plated with the adhering plating material and/or the outer plating material.

In some implementations, the surface of the heating element 100 may be primed for the outer plating material to be deposited onto the heating element 100 using non-plating priming, rather than by plating the surface of the heating element 100 with the adhering plating material. For example, the surface of the heating element 100 may be primed using etching rather than by depositing the adhering plating material.

In some implementations, all or a portion of the legs 106 and the cartridge contacts 65 may be plated with the adhering plating material and/or the outer plating material. In some examples, the cartridge contacts 65 may include at least a portion that has an outer plating material having a greater thickness relative to the remaining portions of the cartridge contacts 65 and/or the legs 106 of the heating element 100. In some implementations, the cartridge contacts 65 and/or the legs 106 may have a greater thickness relative to the tines 102 and/or the heating portion 104.

In some implementations, rather than forming the heating element 100 of a single substrate material and plating the substrate material, the heating element 100 may be formed of various materials that are coupled together (e.g., via laser welding, diffusion processes, etc.). The materials of each portion of the heating element 100 that is coupled together may be selected to provide a low or no resistance at the cartridge contacts 65 and a high resistance at the tines 102 or heating portion 104 relative to the other portions of the heating element 100.

In some implementations, the heating element 100 may be electroplated with silver ink and/or spray coated with one or more plating materials, such as the adhering plating material and the outer plating material.

As mentioned above, the heating element 100 may include various shapes, sizes, and geometries to more efficiently heat the heating portion 104 of the heating element 100 and more efficiently vaporize the vaporizable material.

FIGS. 6-10 illustrate an example of a heating element 100 consistent with implementations of the current subject matter. As shown, the heating element 100 includes the one or more tines 102 located in the heating portion 104, the one or more legs 106 extending from the tines 102, the cartridge contacts 65 formed at the end portion of each of the one or more legs 106, and the heat shields 118 extending from the one or more legs 106. In this example, each of the tines 102 have the same or similar shape and size. The tines 102 have a squared and/or flat outer edge 103. In FIGS. 6-9, the tines 102 have been crimped about a wicking element 70 (e.g., a flat pad) to secure the wicking element 70 within the pocket of the tines 102.

FIGS. 11-12 illustrate another example of a heating element 100 consistent with implementations of the current subject matter in an unbent position (FIG. 11) and a bent position (FIG. 12). As shown, the heating element 100 includes the one or more tines 102 located in the heating portion 104, the one or more legs 106 extending from the tines 102, the cartridge contacts 65 formed at the end portion of each of the one or more legs 106, and the heat shields 118 extending from the one or more legs 106. In this example, each of the tines 102 have the same or similar shape and size and the tines 102 have a rounded and/or semi-circular outer edge 103.

Figure 13:
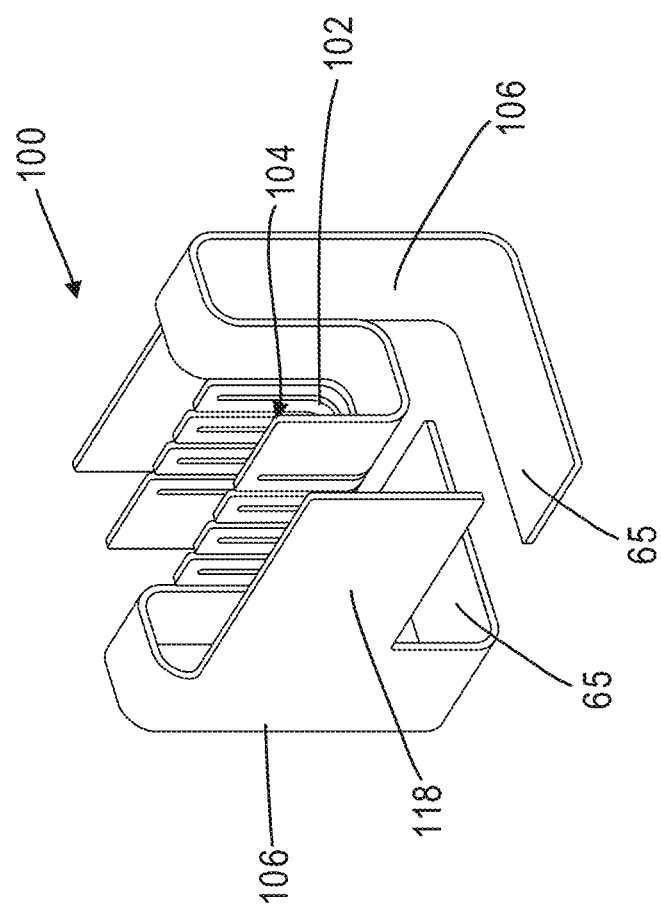
FIG. 13 shows a heating element in a bent position consistent with implementations of the current subject matter.

FIG. 13 illustrates another example of a heating element 100 in a bent position consistent with implementations of the current subject matter that is similar to the example heating element 100 shown in FIGS. 11-12, but in this example, each of the tines 102 have the same or similar shape and size and the tines 102 have a squared and/or flat outer edge 103.

FIGS. 14-19 illustrate other examples of the heating element 100 in which at least one of the tines 102 has a size, shape, or position that is different from the remaining tines 102. For example, as shown in FIGS. 14-15, the heating element 100 includes the one or more tines 102 located in the heating portion 104, the one or more legs 106 extending from the tines 102, and the cartridge contacts 65 formed at the end portion of each of the one or more legs 106. In this example, the tines 102 include a first set of tines 105A and a second set of tines 105B. The first and second sets of tines 105A, 105B are offset from one another. For example, the outer edges 103 of the first and second sets of tines 105A, 105B are not aligned with one another. As shown in FIG. 15, when the heating portion 104 is in the bent position, the first set of tines 105A appear to be shorter than the second set of tines 105B in the first portion of the heating element 100, and the first set of tines 105A appear to be longer than the second set of tines 105B in the second portion of the heating element 100.

Figure 17:
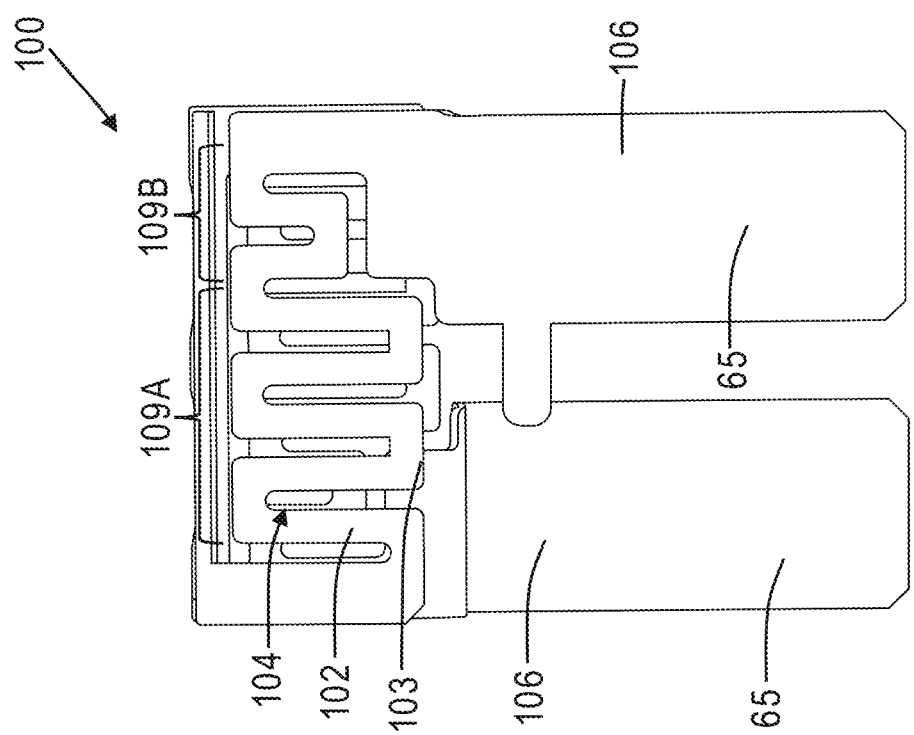
FIG. 17 shows a heating element in a partially bent position consistent with implementations of the current subject matter.
Figure 16:
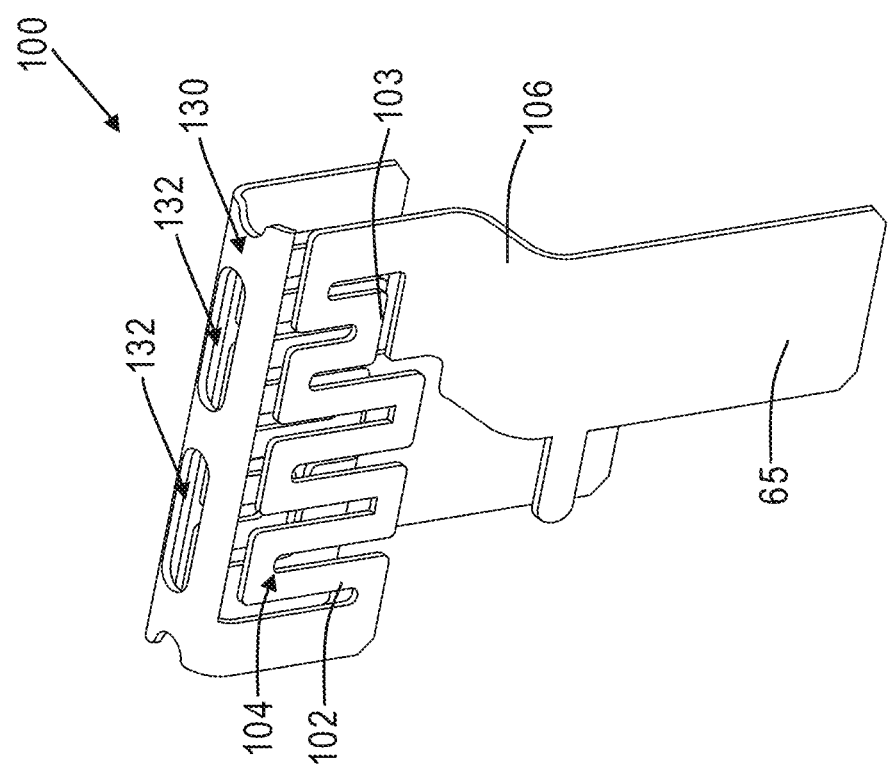
FIG. 16 shows a heating element in a partially bent position consistent with implementations of the current subject matter.

As shown in FIGS. 16-17, the heating element 100 includes the one or more tines 102 located in the heating portion 104, the one or more legs 106 extending from the tines 102, and the cartridge contacts 65 formed at the end portion of each of the one or more legs 106. In this example, the tines 102 include a first set of tines 109A and a second set of tines 109B. The first and second sets of tines 109A, 109B are offset from one another. For example, the outer edges 103 of the first and second sets of tines 109A, 109B are not aligned with one another. Here, the second set of tines 109B includes a single outermost tine 102A. As shown in FIGS. 16-17, when the heating portion 104 is in the bent position, the first set of tines 109A appear to be longer than the second set of tines 109B. In addition, in FIGS. 16-17, the tines 102 are not bent. Rather, the tines 102 are located on a first portion and a second portion of the heating element 100 that is positioned approximately parallel to and opposite the first portion. The first set of tines positioned on the first portion of the heating element 100 are separated from the second set of tines positioned on the second portion of the heating element 100 by a platform portion 130 that is positioned between and spaced from both of the first and second set of tines. The platform portion 130 is configured to contact an end of the wicking element 70. The platform portion 130 includes a cutout portion 132. The cutout portion 132 may provide additional edges along which the vaporizable material can vaporize from when the heating element 100 is activated.

Figure 19:
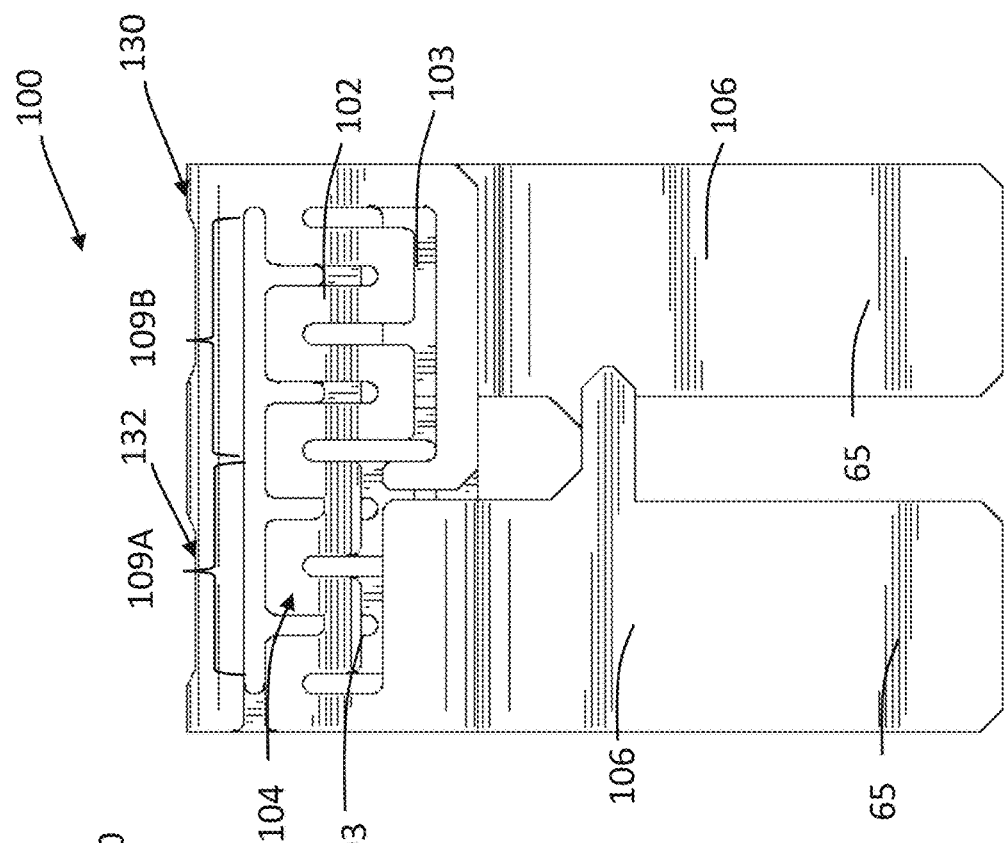
FIG. 19 shows a heating element in a partially bent position consistent with implementations of the current subject matter.
Figure 18:
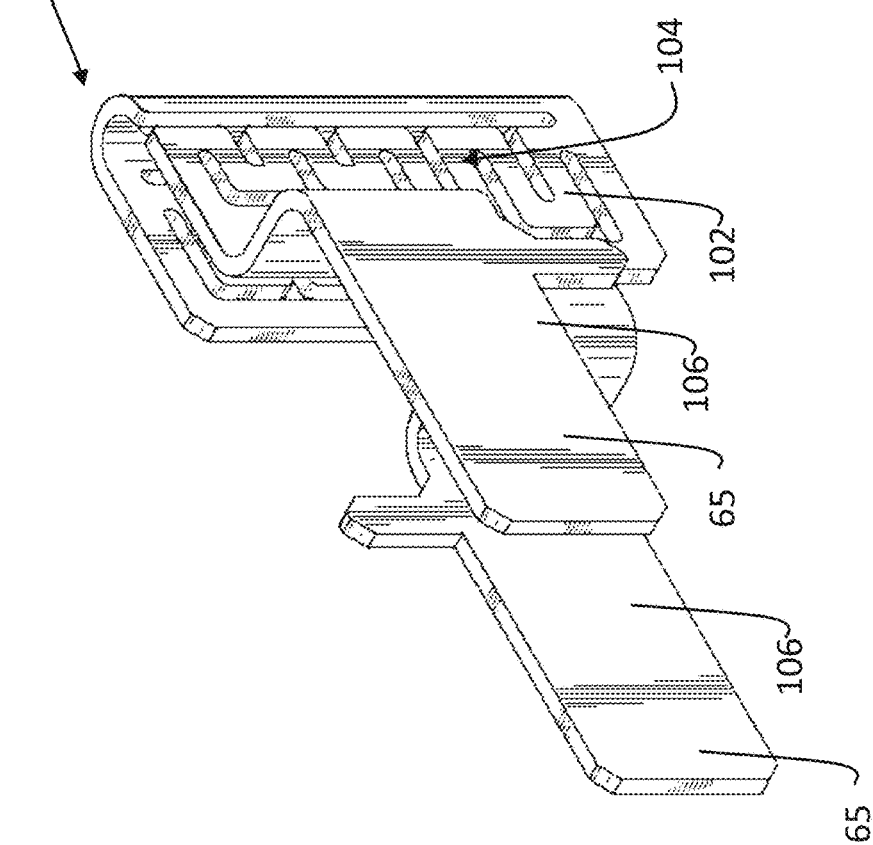
FIG. 18 shows a heating element in a partially bent position consistent with implementations of the current subject matter.

As shown in FIGS. 18-19, the heating element 100 includes the one or more tines 102 located in the heating portion 104, the one or more legs 106 extending from the tines 102, and the cartridge contacts 65 formed at the end portion of each of the one or more legs 106. In this example, the tines 102 include a first set of tines 109A and a second set of tines 109B. The first and second sets of tines 109A, 109B are offset from one another. For example, the outer edges 103 of the first and second sets of tines 109A, 109B are not aligned with one another. Here, each of the first and the second set of tines 109A, 109B includes two tines 102. As shown in FIGS. 18-19, when the heating portion 104 is in the bent position, the first set of tines 109A appear to be shorter than the second set of tines 109B. In addition, in FIGS. 18-19, the tines 102 are not bent. Rather, the tines 102 are located on a first portion and a second portion (that is parallel and opposite the first portion) of the heating element 100. The first set of tines positioned on the first portion are separated from the second set of tines positioned on the second portion by a platform portion that is positioned between and spaced from both of the first and second set of tines. The platform portion is configured to contact an end of the wicking element 70. The platform portion includes a cutout portion. The cutout portion may provide additional edges along which the vaporizable material can vaporize from when the heating element 100 is activated.

FIGS. 20-25 illustrate another example of a heating element 100 consistent with implementations of the current subject matter in an unbent position (FIG. 20) and a bent position (FIGS. 21-25). As shown, the heating element 100 includes the one or more tines 102 located in the heating portion 104, the one or more legs 106 extending from the tines 102, the cartridge contacts 65 formed at the end portion of each of the one or more legs 106, and the heat shields 118 extending from the one or more legs 106. In this example, the heating element 100 is configured to be crimped around and/or bent to receive a cylindrical-shaped wicking element 70 or a wicking element 70 having a circular cross-section. Each of the tines 102 include apertures 140. The apertures 140 may provide additional edges along which the vaporizable material can vaporize from when the heating element 100 is activated. The apertures 140 also reduce the amount of material used to form the heating element 100, reducing the weight of the heating element 100 and the amount of material used for the heating element 100, thereby reducing material costs.

FIGS. 26-35 illustrate a heating element 100 consistent with implementations of the current subject matter in which the heating element 100 is pressed against one side of the wicking element 70. As shown, the heating element 100 includes the one or more tines 102 located in the heating portion 104, the one or more legs 106 extending from the tines 102, and the cartridge contacts 65 formed at the end portion of each of the one or more legs 106. In these examples, the legs 106 and the cartridge contacts 65 are configured to bend in a third direction, rather than in a first-second direction that is perpendicular to the third direction. In such a configuration, the tines 102 of the heating portion 104 form a planar platform that faces outwardly from the heating element 100 and is configured to be pressed against the wicking element 70 (e.g., on one side of the wicking element 70).

FIGS. 28-31 illustrate several examples of the heating element 100 consistent with implementations of the current subject matter including tines 102 configured in various geometries. As mentioned above, the tines 102 form a planar platform that is pressed against one side of the wicking element 70 in use. The legs 106, rather than the tines 102, bend in the bent position.

Figure 33:
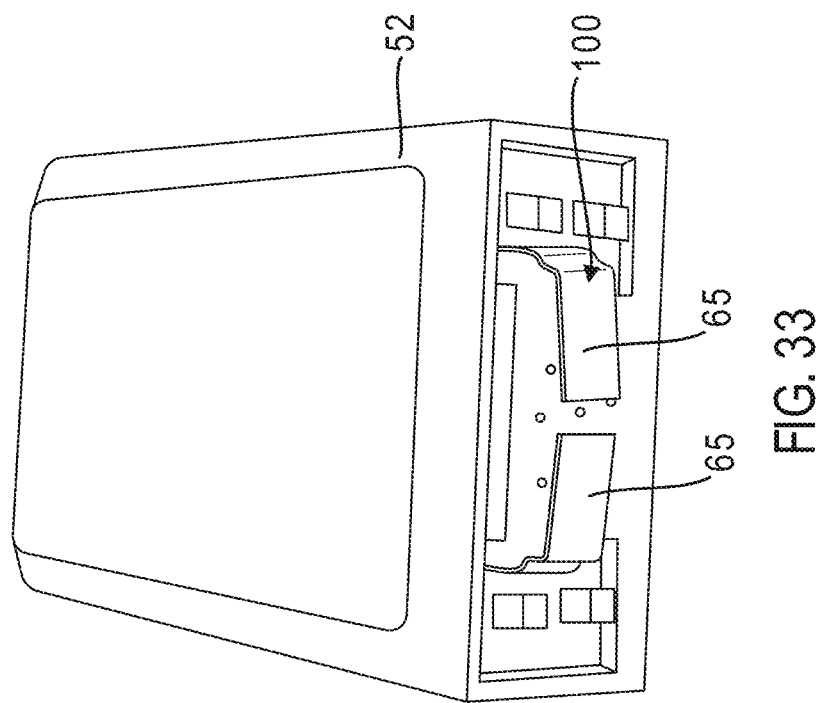
FIG. 33 shows a heating element and a wicking element positioned within a vaporizer cartridge consistent with implementations of the current subject matter.
Figure 32:
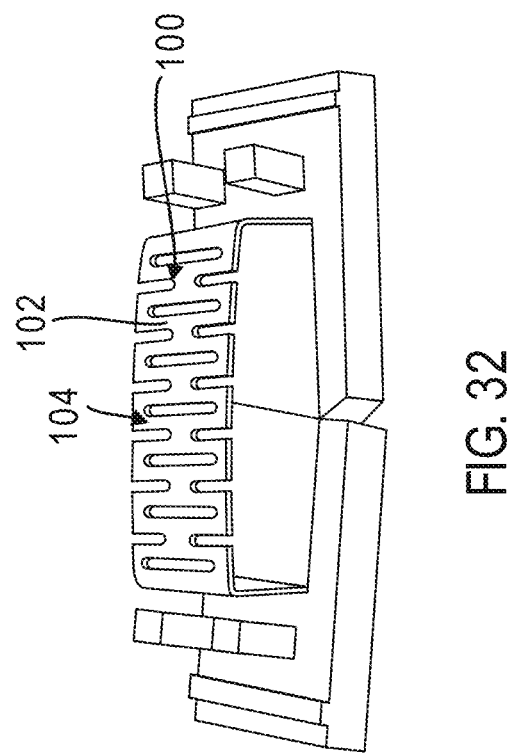
FIG. 32 shows a heating element coupled with a portion of a vaporizer cartridge consistent with implementations of the current subject matter.

FIG. 32 illustrates an example of the heating element 100 shown in FIG. 28 assembled with a component of the vaporizer cartridge 52, such as a wick housing (e.g., the wick housing 98) that houses the wicking element 70 and the heating element 100 and FIG. 33 illustrates the heating element 100 assembled with an example vaporizer cartridge 52 consistent with implementations of the current subject matter. As shown the cartridge contacts 65 are bent towards one another in a lateral direction.

Figure 34:
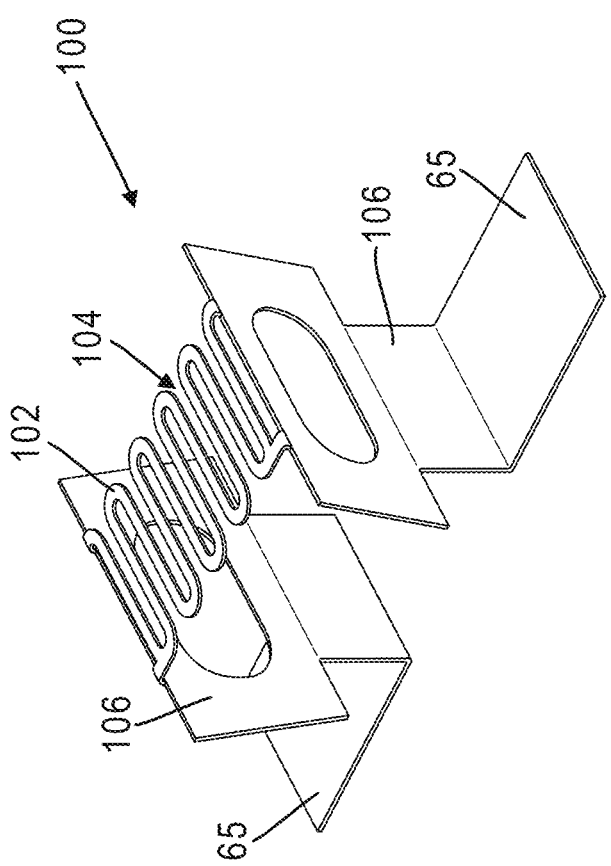
FIG. 34 shows a heating element in a partially bent position consistent with implementations of the current subject matter.
Figure 35:
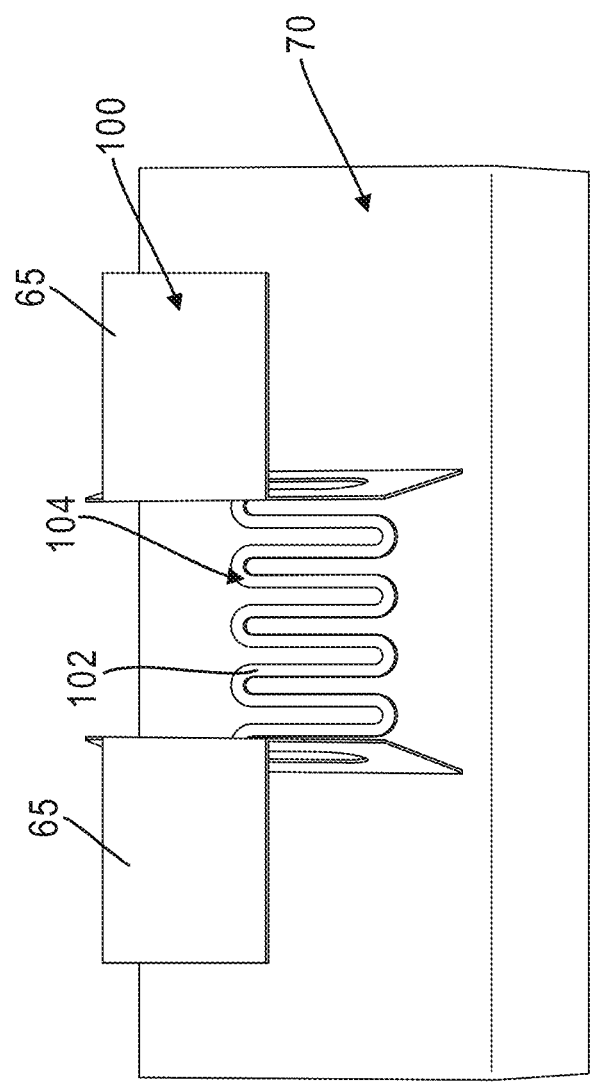
FIG. 35 shows a heating element in a partially bent position and a wicking element consistent with implementations of the current subject matter.

FIGS. 34 and 35 illustrate another example of the heating element 100 in which the tines 102 form a platform that is configured to be pressed against the wicking element 70. Here, the legs 106 may form spring-like structures that force the tines 102 to be pressed against the wicking element 70 when a lateral inward force is applied to each of the legs 106. For example, FIG. 35 illustrates an example of the tines 102 being pressed against the wicking element 70 when power (e.g., a current) is supplied to the heating element 100, such as via the cartridge contacts 65.

FIGS. 39-43 illustrate another example of a heating element 100 consistent with implementations of the current subject matter. As shown, the heating element 100 includes the one or more tines 102 located in the heating portion 104, the one or more legs 106 extending from the tines 102, and the cartridge contacts 65 formed at the end portion and/or as part of each of the one or more legs 106. In this example, each of the tines 102 have the same or similar shape and size, and are spaced apart from one another at equal distances. The tines 102 have a rounded outer edge 103.

Figure 42:
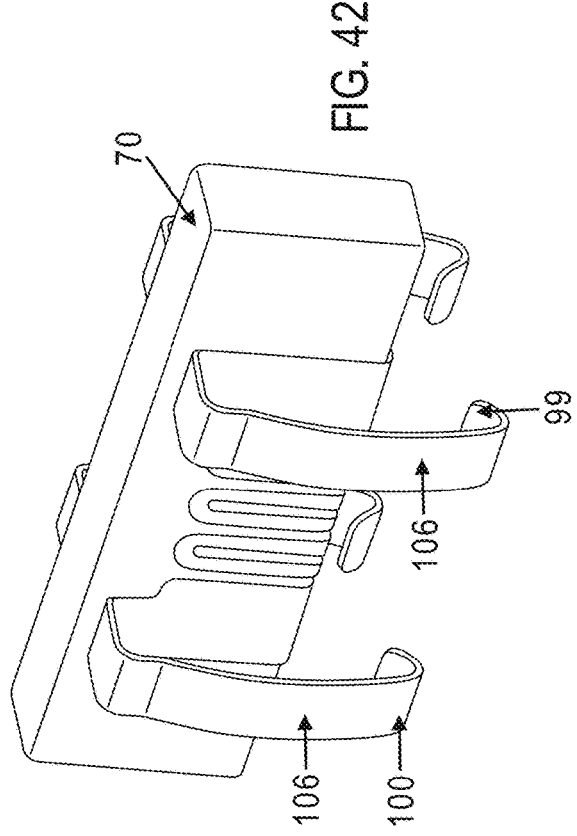
FIG. 42 shows a perspective view of a heating element in a bent position and a wicking element consistent with implementations of the current subject matter.
Figure 43:
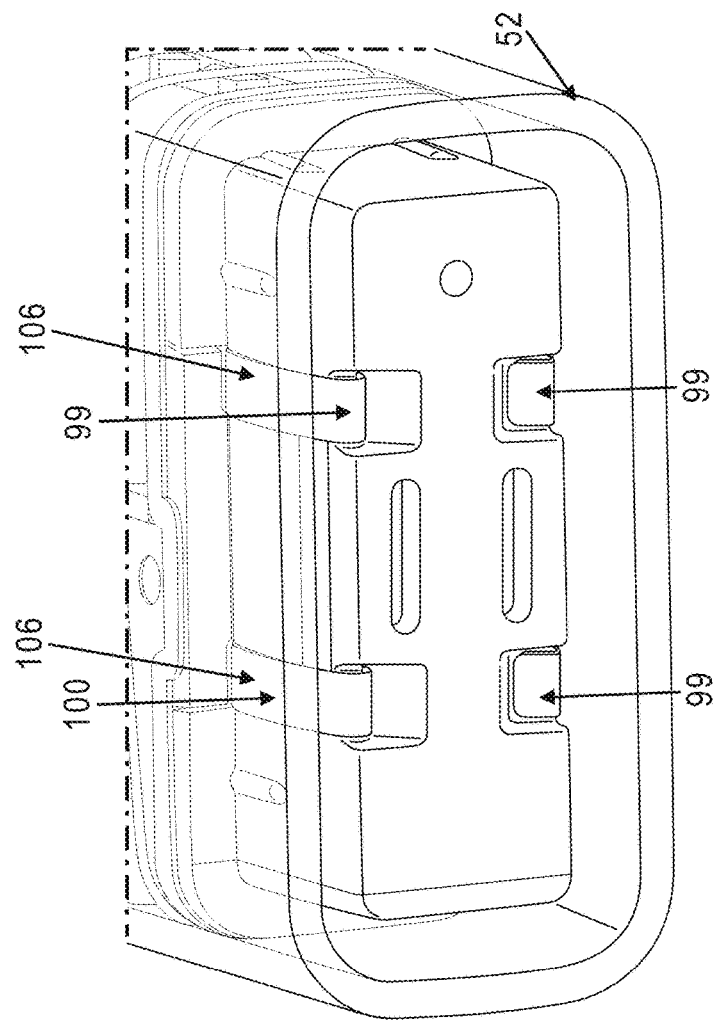
FIG. 43 shows a heating element positioned within a vaporizer cartridge consistent with implementations of the current subject matter.
Figure 44:
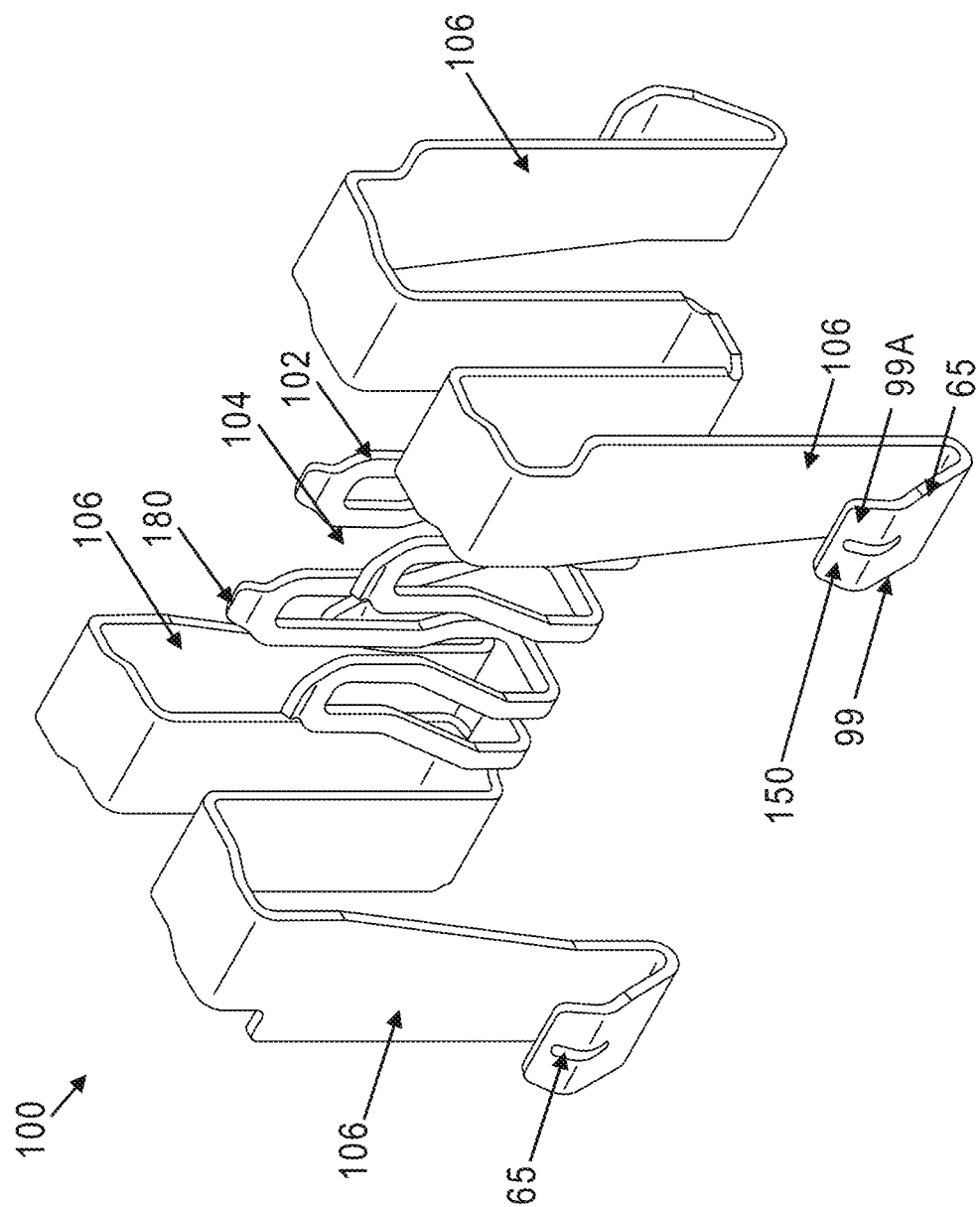
FIG. 44 shows a perspective view of a heating element in a bent position consistent with implementations of the current subject matter.
Figure 50A:
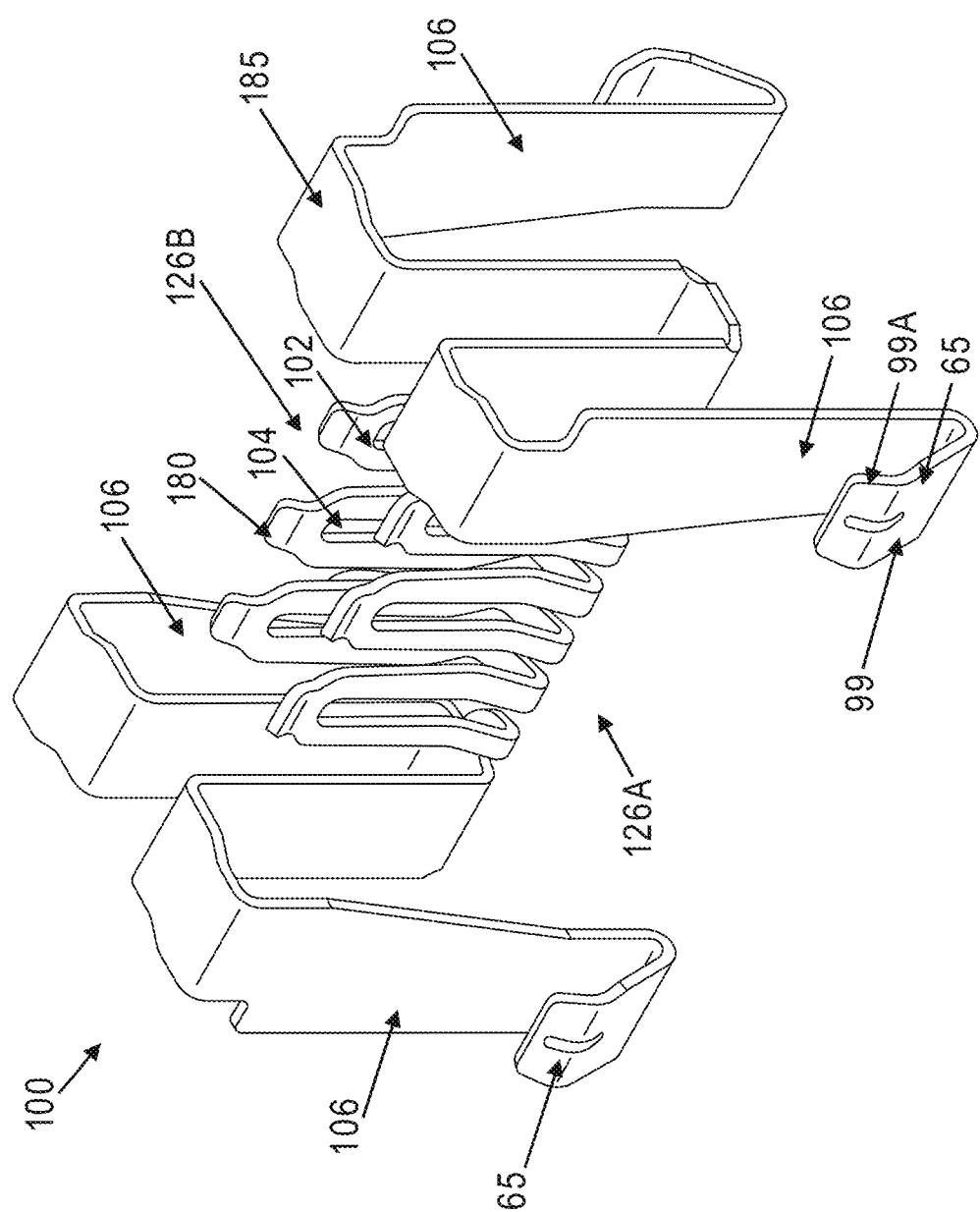
FIG. 50A shows a perspective view of a heating element in a bent position consistent with implementations of the current subject matter.
Figure 50B:
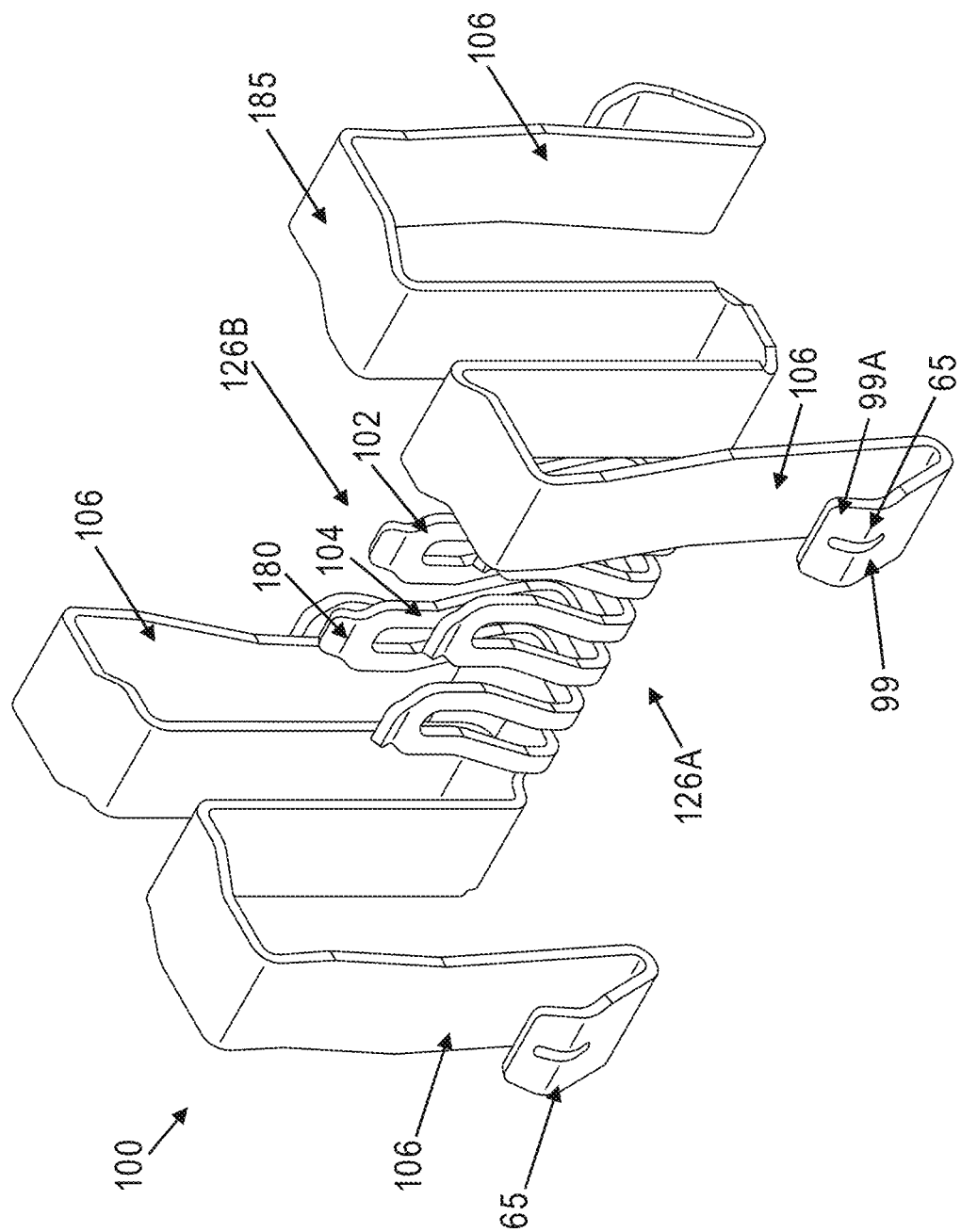
FIG. 50B shows a perspective view of a heating element in a bent position consistent with implementations of the current subject matter.
Figure 54B:
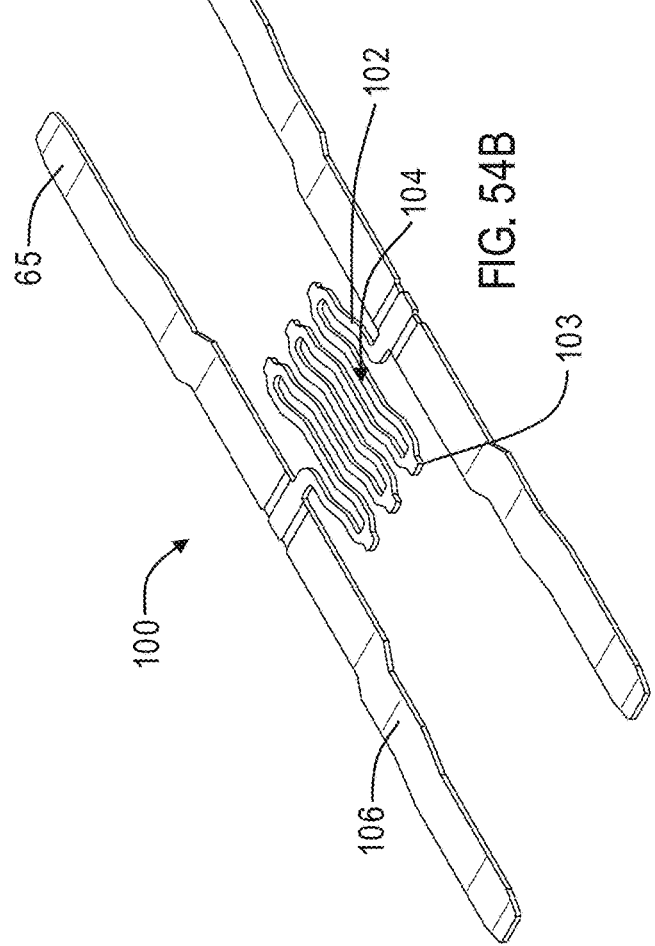
FIG. 54B shows a perspective view of a heating element in an unbent position consistent with implementations of the current subject matter.
Figure 55B:
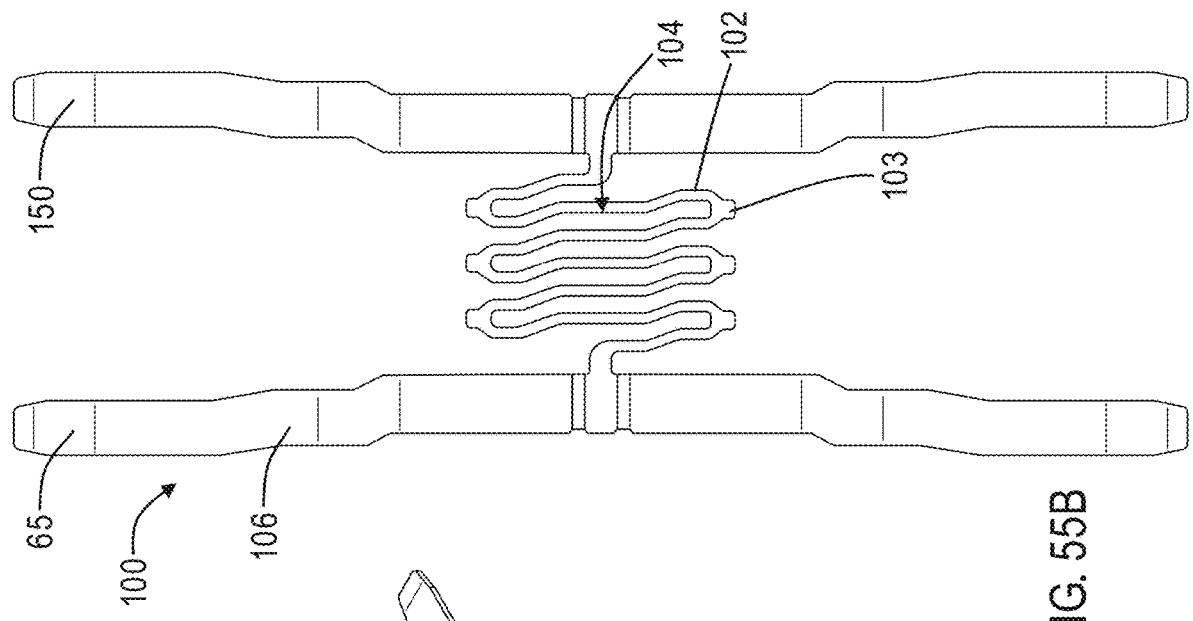
FIG. 55B shows a top view of a heating element in an unbent position consistent with implementations of the current subject matter.

As shown in FIG. 42, the tines 102 have been crimped about a wicking element 70 (e.g., a flat pad) to secure the wicking element 70 within the pocket formed by the tines 102. For example, the tines 102 may be folded and/or crimped to define the pocket in which the wicking element 70 resides. The tines 102 include a platform tine portion 124 and side tine portions 126. The platform tine portion 124 is configured to contact one side of the wicking element 70 and the side tine portions 126 are configured to contact other opposite sides of the wicking element 70. The platform tine portion 124 and the side tine portions 126 form the pocket that is shaped to receive the wicking element 70 and/or conform to the shape of at least a portion of the wicking element 70. The pocket allows the wicking element 70 to be secured and retained by the heating element 100 within the pocket.

In some implementations, the side tine portions 126 and the platform tine portion 124 retain the wicking element 70 via compression (e.g., at least a portion of the wicking element 70 is compressed between the opposing side tine portions 126 and/or the platform tine portion 124). The platform tine portion 124 and the side tine portions 126 contact the wicking element 70 to provide a multi-dimensional contact between the heating element 100 and the wicking element 70. Multi-dimensional contact between the heating element 100 and the wicking element 70 provides for a more efficient and/or faster transfer of the vaporizable material from the reservoir 55 of the vaporizer cartridge 52 to the heating portion 104 (via the wicking element 70) to be vaporized.

The one or more legs 106 of the example heating element 100 shown in FIGS. 39-43 includes four legs 106. Each of the legs 106 may include and/or define a cartridge contact 65 that is configured to contact a corresponding receptacle contact 62 of the vaporizer 10. In some implementations, each pair of legs 106 (and the cartridge contacts 65) may contact a single receptacle contact 62. The legs 106 may be spring-loaded to allow the legs 106 to maintain contact with the receptacle contacts 62. The legs 106 may include a portion that extends along a length of the legs 106 that is curved to help to maintain contact with the receptacle contacts 62. Spring-loading the legs 106 and/or the curvature of the legs 106 may help to increase and/or maintain consistent pressure between the legs 106 and the receptacle contacts 62. In some implementations, the legs 106 are coupled with a support 97 that helps to increase and/or maintain consistent pressure between the legs 106 and the receptacle contacts 62. The support 97 may include plastic, rubber, or other materials to help maintain contact between the legs 106 and the receptacle contacts 62. In some implementations, the support 97 is formed as a part of the legs 106.

The legs 106 may contact one or more wiping contacts that are configured to clean the connection between the cartridge contacts 65 and other contacts or power source. For example, the wiping contacts would include at least two parallel, but offset, bosses that frictionally engage and slide against one another in a direction that is parallel or perpendicular to the insertion direction.

As shown in FIGS. 39-55, the one or more legs 106 of the heating element 100 includes four legs 106. FIGS. 48-49, 54A-55B, and 66-67 show examples of the heating element 100 in the unbent position. As shown, the heating element 100 has an H-shape, defined by the four legs 106 and the tines 102. This configuration allows for resistance across the heater to be measured more accurately, and reduces variability in the resistance measurements, thereby allowing for more efficiency aerosol generation and higher quality aerosol generation. The heating element 100 includes two pairs of opposing legs 106. The tines 102 are coupled (e.g., intersect) with each of the pairs of opposing legs 106 at or near a center of each of the pairs of opposing legs 106. The heating portion 104 is positioned between the pairs of opposing legs 106.

Figure 66:
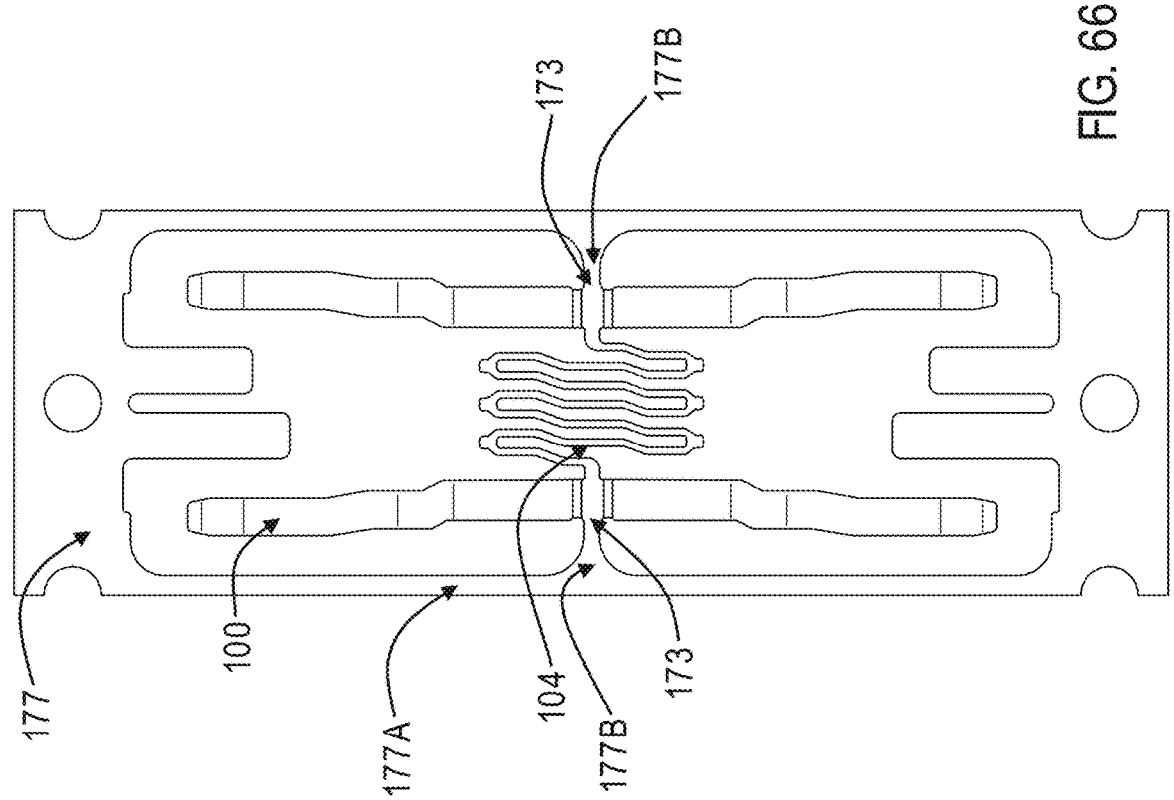
FIG. 66 shows a top view of a substrate material with a heating element consistent with implementations of the current subject matter.

FIG. 66 illustrates an example of the heating element 100 before the heating element 100 has been stamped and/or otherwise formed from a substrate material 177. Excess substrate material 177A may be coupled with the heating element 100 at one, two, or more coupling locations 177B. For example, as shown, the excess substrate material 177A may be coupled with the heating element 100 at two coupling locations 177B, near opposing lateral ends 173 of the platform portion of the heating element and/or heating portion 104 of the heating element 100. In some implementations, the heating element 100 may be first be stamped from the substrate material 177, and then removed from the excess substrate material 177A at the coupling locations 177B (e.g., by twisting, pulling, stamping, cutting, etc., the heating element 100).

As noted above, to crimp the heating element 100, the heating element 100 may be bent or otherwise folded along fold lines 123, 122A, 122B, 120 towards or away from one another (see, for example, FIG. 55A). Though the fold lines are illustrated in FIG. 55A, the example heating elements 100 described and shown in FIGS. 1D-72C may also be crimped, folded, or otherwise bent along the fold lines. Folding the heating element 100 along fold lines 120 forms a platform tine portion 124 defined by the region between the fold lines 120 and/or between side tine portions 126 defined by the region between the fold lines 120 and the outer edges 103 of the tines 102. The platform tine portion 124 may contact one end and/or support one end of the wicking element 70. The side tine portions 126 may contact opposite sides of the wicking element 70. The platform tine portion 124 and the side tine portions 126 define an interior volume of the heating element that forms a pocket shaped to receive the wicking element 70 and/or conform to the shape of at least a portion of the wicking element 70. The interior volume allows the wicking element 70 to be secured and retained by the heating element 100 within the pocket. The platform tine portion 124 and the side tine portions 126 contact the wicking element 70 to provide a multi-dimensional contact between the heating element 100 and the wicking element 70. Multi-dimensional contact between the heating element 100 and the wicking element 70 provides for a more efficient and/or faster transfer of the vaporizable material from the reservoir 55 of the vaporizer cartridge 52 to the heating portion 104 (via the wicking element 70) to be vaporized.

In some implementations, portions of the legs 106 of the heating element 100 may also be bent along fold lines 122A, 122B. Folding the portions of the legs 106 of the heating element 100 along fold lines 122 away from one another locates the legs 106 at a position spaced away from the heating portion 104 (and tines 102) of the heating element 100 in a first and/or second direction opposite the first direction (e.g., in the same plane). Thus, folding the portions of the legs 106 of the heating element 100 along fold lines 122 away from one another spaces the heating portion 104 from the body of the vaporizer cartridge 52. Folding the portions of the legs 106 along the fold lines 122A, 122B forms a bridge 185. In some implementations, the bridge 185 helps to reduce or eliminate overflow of vaporizable material from the heating portion 104, such as due to capillary action. The bridge 185 also helps to isolate the heating portion 104 from the legs 106, so that the heat generated at the heating portion 104 does not reach the legs 106. This also helps to localize heating of the heating element 100 to within the heating portion 104.

In some implementations, the heating element 100 may also be bent along fold lines 123 to define the cartridge contacts 65. The cartridge contacts 65 may be exposed to the environment or may otherwise be accessible (and may be positioned within an interior of a portion of the cartridge, such as the outer shell) to contact the receptacle contacts, while other portions, such as the heating portion 104 of the heating element 100, are positioned within an inaccessible part of the vaporizer cartridge 52, such as the wick housing.

In some implementations, the legs 106 include retainer portions 99 that are configured to be bent around at least a portion of a wick housing 98 that surrounds at least a portion of the wicking element 70 and heating element 100 (such as the heating portion 104). The retainer portions 99 form an end of the legs 106. The retainer portions 99 help to secure the heating element 100 and wicking element 70 to the wick housing 98 (and the vaporizer cartridge 52). The retainer portions 99 may alternatively be bent away from at least a portion of the wick housing 98.

FIGS. 44-49 illustrate another example of a heating element 100 consistent with implementations of the current subject matter. As shown, the heating element 100 includes the one or more tines 102 located in the heating portion 104, the one or more legs 106 extending from the tines 102, and the cartridge contacts 65 formed at the end portion and/or as part of each of the one or more legs 106.

The tines 102 may be folded and/or crimped to define the pocket in which a wicking element 70 (e.g., a flat pad) resides. The tines 102 include a platform tine portion 124 and side tine portions 126. The platform tine portion 124 is configured to contact one side of the wicking element 70 and the side tine portions 126 are configured to contact other opposite sides of the wicking element 70. The platform tine portion 124 and the side tine portions 126 form the pocket that is shaped to receive the wicking element 70 and/or conform to the shape of at least a portion of the wicking element 70. The pocket allows the wicking element 70 to be secured and retained by the heating element 100 within the pocket.

In this example, the tines 102 have various shapes and size, and are spaced apart from one another at the same or varying distances. For example, as shown, each of the side tine portions 126 includes at least four tines 102. In a first pair 170 of adjacent tines 102, each of the adjacent tines 102 is spaced apart at an equal distance from an inner region 176 positioned near the platform tine portion 124 to an outer region 178 positioned near the outer edge 103. In a second pair 172 of adjacent tines 102, the adjacent tines 102 are spaced apart by a varying distance from the inner region 176 to the outer region 178. For example, the adjacent tines 102 of the second pair 172 are spaced apart by a width that is greater at the inner region 176 than at the outer region 178. These configurations may help to maintain a constant and uniform temperature along the length of the tines 102 of the heating portion 104. Maintaining a constant temperature along the length of the tines 102 may provide higher quality aerosol, as the maximum temperature is more uniformly maintainable across the entire heating portion 104.

As noted above, each of the legs 106 may include and/or define a cartridge contact 65 that is configured to contact a corresponding receptacle contact 62 of the vaporizer 10. In some implementations, each pair of legs 106 (and the cartridge contacts 65) may contact a single receptacle contact 62. In some implementations, the legs 106 include retainer portions 99 that are configured to be bent and generally extend away from the heating portion 104. The retainer portions 99 are configured to be positioned within a corresponding recess in the wick housing 98. The retainer portions 99 form an end of the legs 106. The retainer portions 99 help to secure the heating element 100 and wicking element 70 to the wick housing 98 (and the vaporizer cartridge 52). The retainer portions 99 may have a tip portion 99A that extends from an end of the retainer portion 99 towards the heating portion 104 of the heating element 100. This configuration reduces the likelihood that the retainer portion will contact another portion of the vaporizer cartridge 52, or a cleaning device for cleaning the vaporizer cartridge 52.

The outer edge 103 of the tines 102 in the heating portion 104 may include a tab 180. The tab 180 may include one, two, three, four, or more tabs 180. The tab 180 may extend outwardly from the outer edge 103 and extend away from a center of the heating element 100. For example, the tab 180 may be positioned along an edge of the heating element 100 surrounding an internal volume defined by at least the side tine portions 126 for receiving the wicking element 70. The tab 180 may extend outwardly away from the internal volume of the wicking element 70. The tab 180 may also extend away in a direction opposite the platform tine portion 124. In some implementations, tabs 180 positioned on opposing sides of the internal volume of the wicking element 70 may extend away from one another. This configuration helps to widen the opening leading to the internal volume of the wicking element 70, thereby helping to reduce the likelihood that the wicking element 70 will catch, tear, and/or become damaged when assembled with the heating element 100. Due to the material of the wicking element 70, the wicking element 70 may easily catch, tear, and/or otherwise become damaged when assembled (e.g., positioned within or inserted into) with the heating element 100. Contact between the wicking element 70 and the outer edge 103 of the tines 102 may also cause damage to the heating element. The shape and/or positioning of the tab 180 may allow the wicking element 70 to more easily be positioned within or into the pocket (e.g., the internal volume of the heating element 100) formed by the tines 102, thereby preventing or reducing the likelihood that the wicking element 70 and/or the heating element will be damaged. Thus, the tabs 180 help to reduce or prevent damage caused to the heating element 100 and/or the wicking element 70 upon entry of the wicking element 70 into thermal contact with the heating element 100. The shape of the tab 180 also helps to minimize impact on the resistance of the heating portion 104.

In some implementations, at least a portion of the cartridge contacts 65 and/or at least a portion of the legs 106 may be plated with one or more outer plating materials 150 to reduce contact resistance at the point where the heating element 100 contacts the receptacle contacts 62.

FIGS. 50A-55B illustrate another example of a heating element 100 consistent with implementations of the current subject matter. As shown, the heating element 100 includes the one or more tines 102 located in the heating portion 104, the one or more legs 106 extending from the tines 102, and the cartridge contacts 65 formed at the end portion and/or as part of each of the one or more legs 106.

The tines 102 may be folded and/or crimped to define the pocket in which a wicking element 70 (e.g., flat pad) resides. The tines 102 include a platform tine portion 124 and side tine portions 126. The platform tine portion 124 is configured to contact one side of the wicking element 70 and the side tine portions 126 are configured to contact other opposite sides of the wicking element 70. The platform tine portion 124 and the side tine portions 126 form the pocket that is shaped to receive the wicking element 70 and/or conform to the shape of at least a portion of the wicking element 70. The pocket allows the wicking element 70 to be secured and retained by the heating element 100 within the pocket.

In this example, the tines 102 have the same shape and size and are spaced apart from one another at equal distances. Here, the tines 102 include a first side tine portion 126A and a second side tine portion 126B that are spaced apart by the platform tine portion 124. Each of the first and second side tine portions 126A, 126B include an inner region 176 positioned near the platform tine portion 124 to an outer region 178 positioned near the outer edge 103. At the outer region 178, the first side tine portion 126A is positioned approximately parallel to the second tine portion 126B. At the inner region 176, the first side tine portion 126A is positioned offset from the second tine portion 126B and the first and second side tine portions 126A, 126B are not parallel. This configuration may help to maintain a constant and uniform temperature along the length of the tines 102 of the heating portion 104. Maintaining a constant temperature along the length of the tines 102 may provide higher quality aerosol, as the maximum temperature is more uniformly maintainable across the entire heating portion 104.

As noted above, each of the legs 106 may include and/or define a cartridge contact 65 that is configured to contact a corresponding receptacle contact 62 of the vaporizer 10. In some implementations, each pair of legs 106 (and the cartridge contacts 65) may contact a single receptacle contact 62. In some implementations, the legs 106 include retainer portions 99 that are configured to be bent and generally extend away from the heating portion 104. The retainer portions 99 are configured to be positioned within a corresponding recess in the wick housing 98. The retainer portions 99 form an end of the legs 106. The retainer portions 99 help to secure the heating element 100 and wicking element 70 to the wick housing 98 (and the vaporizer cartridge 52). The retainer portions 99 may have a tip portion 99A that extends from an end of the retainer portion 99 towards the heating portion 104 of the heating element 100. This configuration reduces the likelihood that the retainer portion will contact another portion of the vaporizer cartridge 52, or a cleaning device for cleaning the vaporizer cartridge 52.

The outer edge 103 of the tines 102 in the heating portion 104 may include a tab 180. The tab 180 may extend outwardly from the outer edge 103 and extend away from a center of the heating element 100. The tab 180 may be shaped to allow the wicking element 70 to more easily be positioned within the pocket formed by the tines 102, thereby preventing or reducing the likelihood that the wicking element 70 will get caught on the outer edge 103. The shape of the tab 180 helps to minimize impact on the resistance of the heating portion 104.

In some implementations, at least a portion of the cartridge contacts 65 and/or at least a portion of the legs 106 may be plated with one or more outer plating materials 150 to reduce contact resistance at the point where the heating element 100 contacts the receptacle contacts 65.

Figure 56:
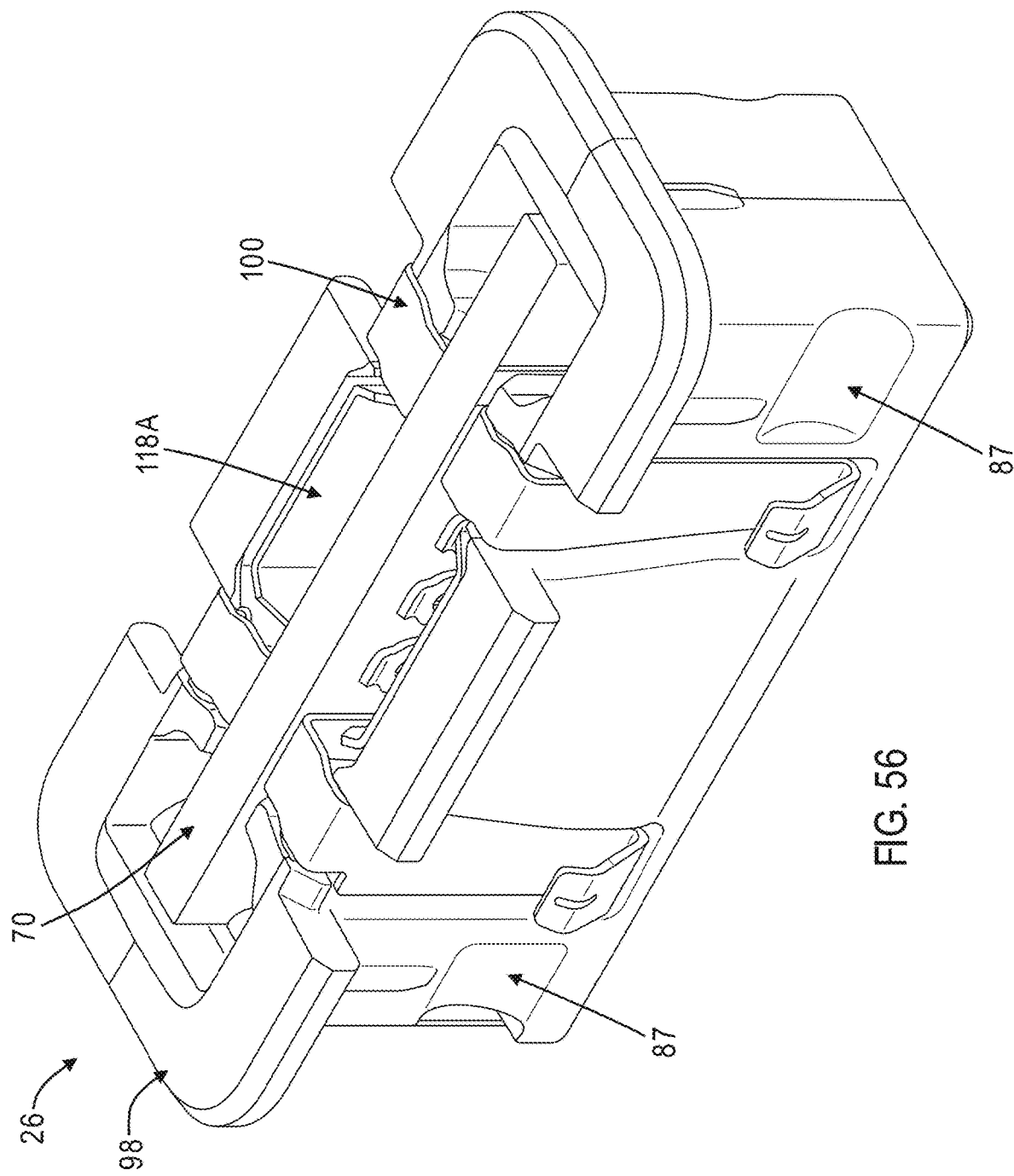
FIG. 56 shows a top perspective view of an atomizer assembly consistent with implementations of the current subject matter.
Figure 57:
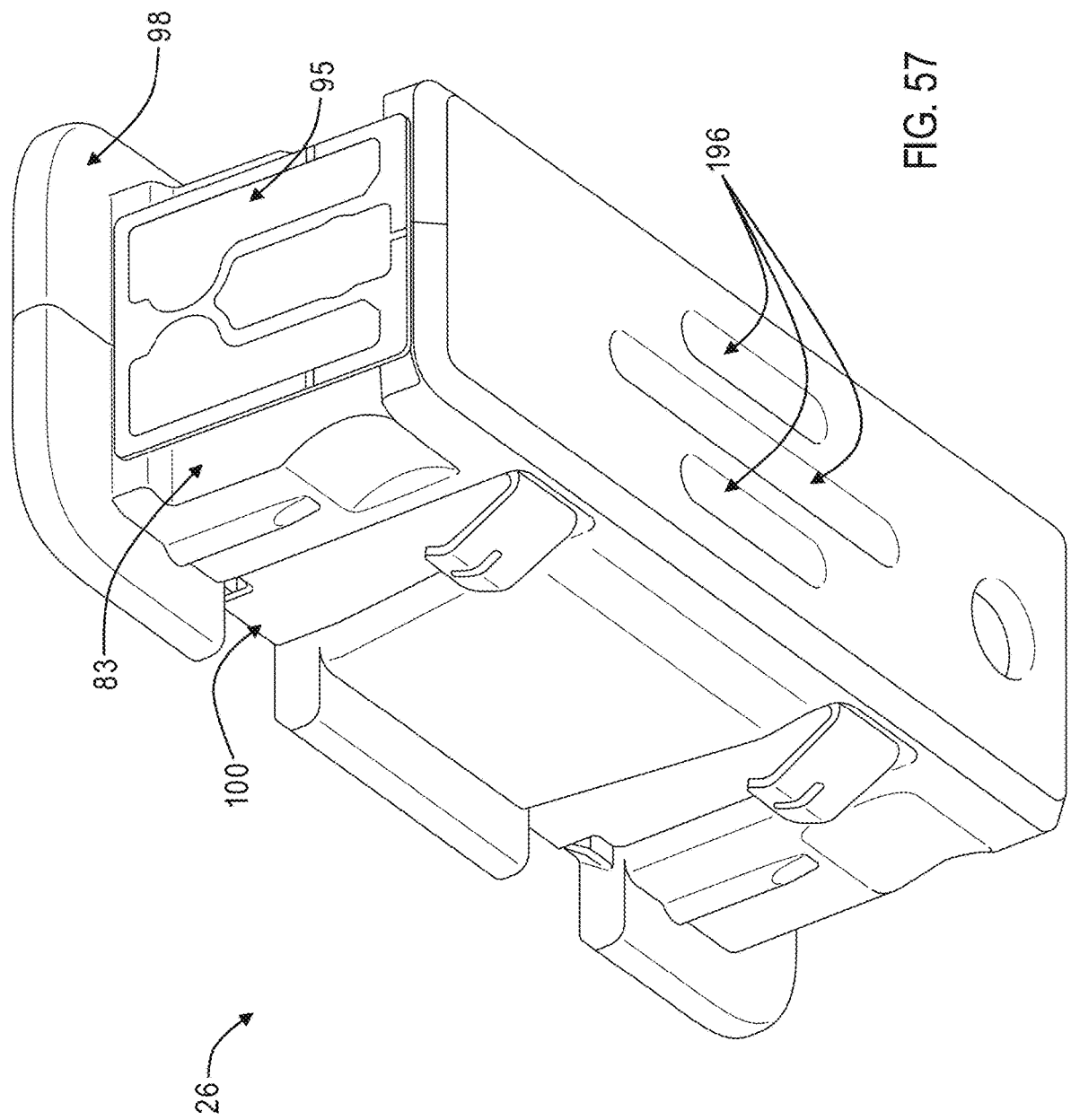
FIG. 57 shows a bottom perspective view of an atomizer assembly consistent with implementations of the current subject matter.

FIGS. 56-57 illustrate an example of the atomizer assembly 26, with the heating element 100 assembled with the wick housing 98, and FIG. 58 illustrates an exploded view of the atomizer assembly 26, consistent with implementations of the current subject matter. The wick housing 98 may be made of plastic, polypropylene, and the like. The wick housing 98 includes four recesses 192 in which at least a portion of each of the legs 106 of the heating element 100 may be positioned and secured. As shown, the wick housing 98 also includes an opening 193 providing access to an internal volume 194, in which at least the heating portion 104 of the heating element 100 and the wicking element 70 are positioned.

The wick housing 98 may also include a separate heat shield 118A, which is shown in FIG. 59. The heat shield 118A is positioned within the internal volume 194 within the wick housing 98 between the walls of the wick housing 98 and the heating element 100. The heat shield 118A is shaped to at least partially surround the heating portion 104 of the heating element 100 and to space the heating element 100 from the side walls of the wick housing 98. The heat shield 118A can help to insulate the heating portion 104 from the body of the vaporizer cartridge 52 and/or the wick housing 98. The heat shield 118A helps to minimize the effects of the heat emanating from the heating portion 104 on the body of the vaporizer cartridge 52 and/or the wick housing 98 to protect the structural integrity of the body of the vaporizer cartridge 52 and/or the wick housing 98 and to prevent melting or other deformation of the vaporizer cartridge 52 and/or the wick housing 98. The heat shield 118A may also help to maintain a consistent temperature at the heating portion 104 by retaining heat within the heating portion 104, thereby preventing or limiting heat losses.

The heat shield 118A includes one or more slots 190 (e.g., three slots) at one end that align with one or more slots (e.g., one, two, three, four, five, six, or seven or more slots) 196 formed in a portion of the wick housing 98 opposite the opening 193, such as a base of the wick housing 98 (see FIGS. 57 and 69). The one or more slots 190, 196 allow for the escape of pressure caused by the flow of liquid vaporizable material within the heater portion 104 and vaporization of vaporizable material, without affecting liquid flow of the vaporizable material.

In some implementations, flooding may occur between the heating element 100 (e.g., the legs 106) and an outer wall of the wick housing 98 (or between portions of the heating element 100). For example, liquid vaporizable material may build up due to capillary pressure between the legs 106 of the heating element 100 and the outer wall of the wick housing 98, as indicated by liquid path 199. In such cases, there may be sufficient capillary pressure to draw the liquid vaporizable material out of the reservoir and/or the heating portion 104. To help limit and/or prevent liquid vaporizable material from escaping the internal volume of the wick housing 98 (or the heating portion 104), the wick housing 98 and/or the heating element 100 may include a capillary feature that causes an abrupt change in capillary pressure, thereby forming a liquid barrier that prevents the liquid vaporizable material from passing the feature without the use of an additional seal (e.g., a hermetic seal). The capillary feature may define a capillary break, formed by a sharp point, a bend, a curved surface, or other surface in the wick housing 98 and/or the heating element 100. The capillary feature allows a conductive element (e.g., the heating element 100) to be positioned within both a wet and dry region.

The capillary feature may be positioned on and/or form a part of the heating element 100 and/or the wick housing 98 and causes an abrupt change in capillary pressure. For example, the capillary feature may include a bend, sharp point, curved surface, angled surface, or other surface feature that causes an abrupt change in capillary pressure between the heating element and the wick housing, along a length of the heating element, or another component of the vaporizer cartridge. The capillary feature may also include a protrusion or other portion of the heating element and/or wick housing that widens a capillary channel, such as a capillary channel formed between portions of the heating element, between the heating element and the wick housing, and the like, that is sufficient to reduce the capillary pressure within the capillary channel (e.g., the capillary feature spaces the heating element from the wick housing) such that the capillary channel does not draw liquid into the capillary channel. Thus, the capillary feature prevents or limits liquid from flowing along a liquid path beyond the capillary feature, due at least in part to the abrupt change and/or reduction in capillary pressure. The size and/or shape of the capillary feature (e.g., the bend, sharp point, curved surface, angled surface, protrusion, and the like) may be a function of a wetting angle formed between materials, such as the heating element and wick housing, or other walls of a capillary channel formed between components, may be a function of a material of the heating element and/or the wick housing or other component, and/or may be a function of a size of a gap formed between two components, such as the heating element and/or wick housing defining the capillary channel, among other properties.

Figure 60B:
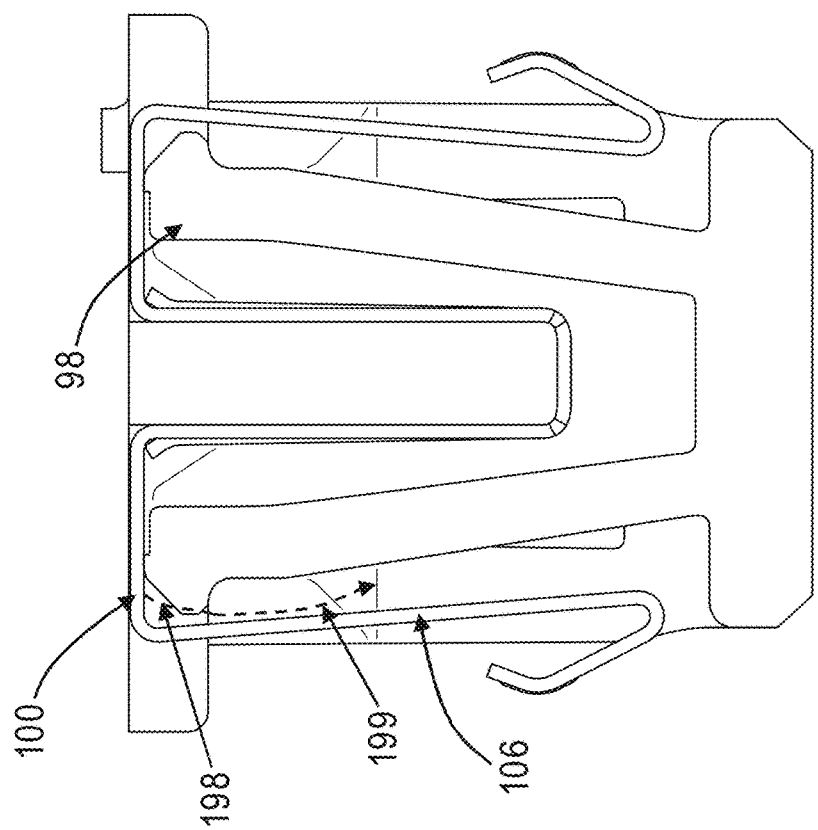
FIG. 60B shows another side cross-sectional view of an atomizer assembly consistent with implementations of the current subject matter.
Figure 60A:
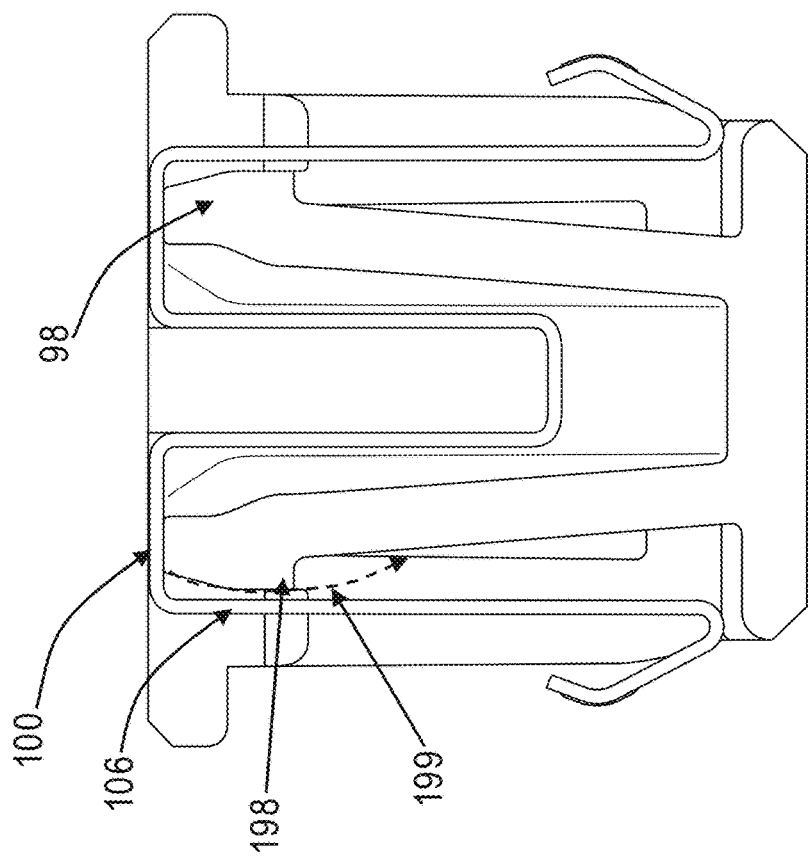
FIG. 60A shows a side cross-sectional view of an atomizer assembly consistent with implementations of the current subject matter.

As an example, FIGS. 60A and 60B illustrate the wick housing 98 having a capillary feature 198 that causes an abrupt change in capillary pressure. The capillary feature 198 prevents or limits liquid from flowing along the liquid path 199 beyond the capillary feature 198, and helps to prevent liquid from pooling between the legs 106 and the wick housing 98. The capillary feature 198 on the wick housing 98 spaces the heating element 100 (e.g., a component made of metal, etc.) away from the wick housing 98 (e.g., a component made of plastic, etc.), thereby reducing the capillary strength between the two components. The capillary feature 198 shown in FIGS. 60A and 60B also includes a sharp edge at an end of an angled surface of the wick housing that limits or prevents liquid from flowing beyond the capillary feature 198.

As shown in FIG. 60B, the legs 106 of the heating element 100 may also be angled inwardly towards the interior volume of the heating element 100 and/or wick housing 98. The angled legs 106 may form a capillary feature that helps to limit or prevent liquid from flowing over an outer surface of the heating element and along the legs 106 of the heating element 100.

As another example, the heating element 100 may include a capillary feature (e.g., a bridge 185) that is formed with the one or more legs 106 and spaces the legs 106 away from the heating portion 104 (See FIGS. 39-55). The bridge 185 may be formed by folding the heating element 100 along the fold lines 120, 122. In some implementations, the bridge 185 helps to reduce or eliminate overflow of vaporizable material from the heating portion 104, such as due to capillary action. In some examples, such as the example heating elements 100 shown in FIGS. 50A-55B, the bridge 185 is angled and/or includes a bend to help limit fluid flow out of the heating portion 104.

Figure 61:
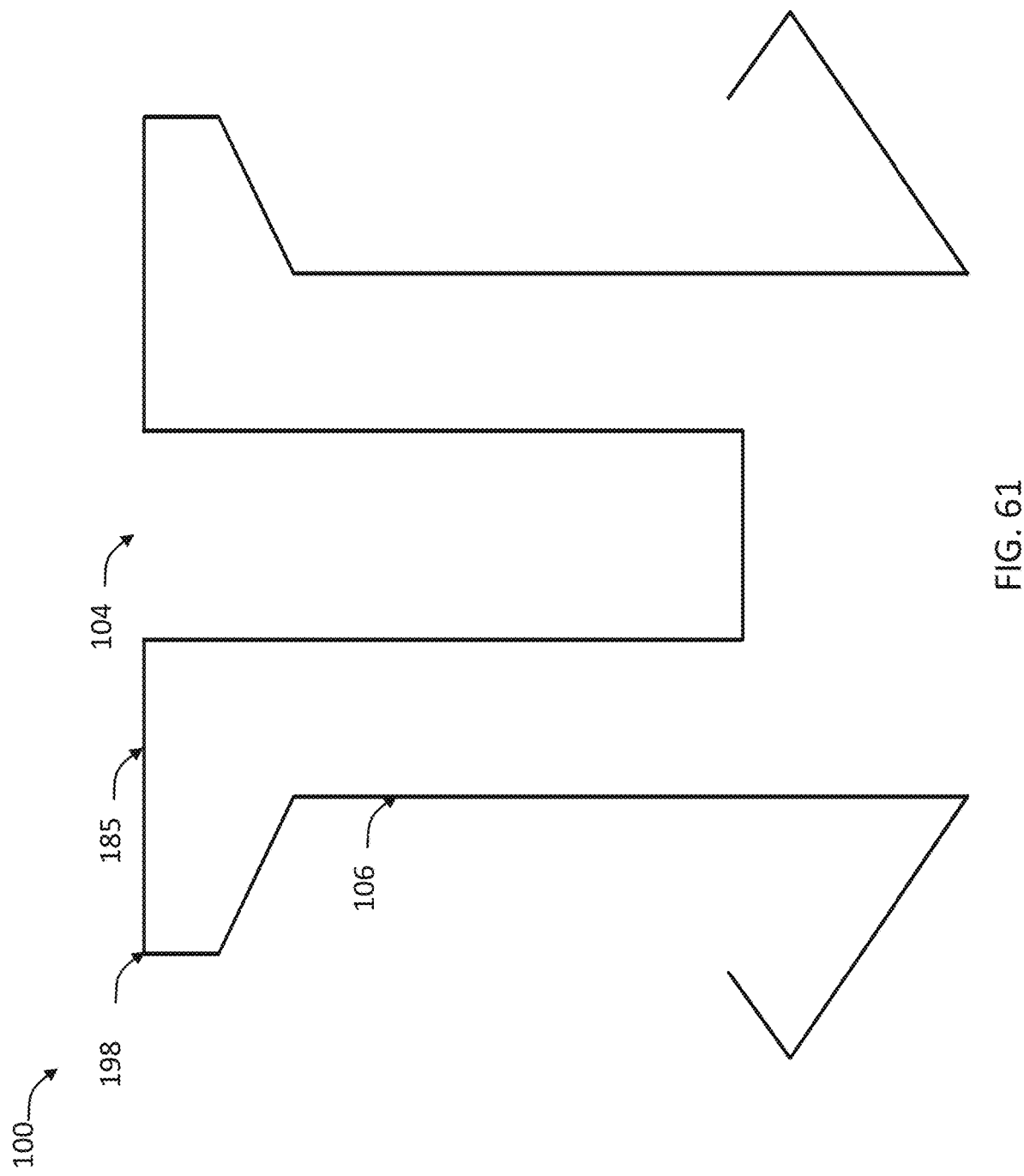
FIG. 61 schematically shows a heating element consistent with implementations of the current subject matter.
Figure 67:
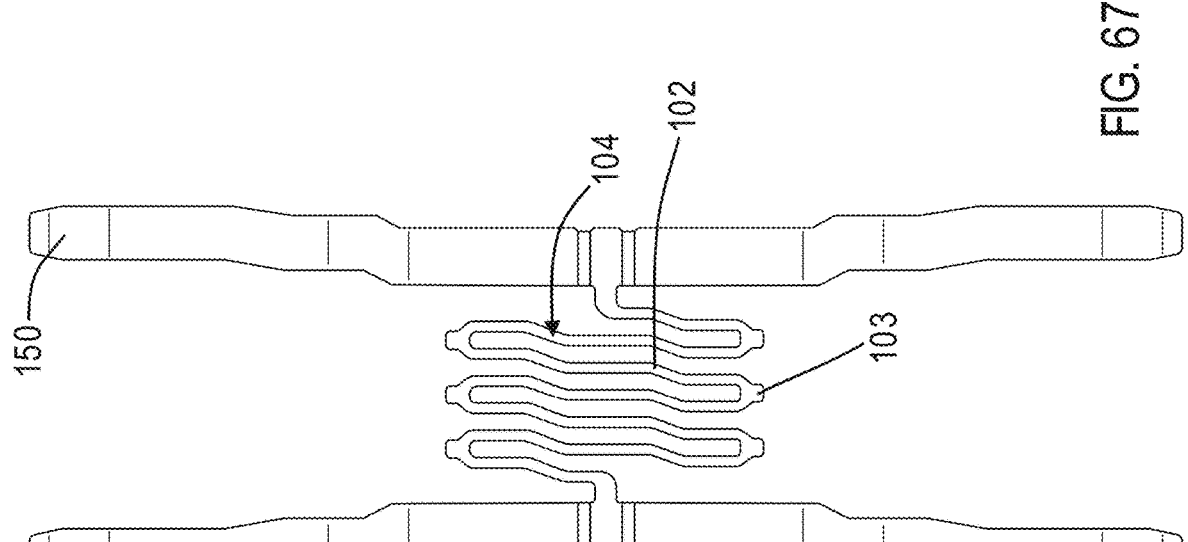
FIG. 67 shows a top view of a heating element in an unbent position consistent with implementations of the current subject matter.

As another example, the heating element 100 may include a capillary feature 198 that defines a sharp point to causes an abrupt change in capillary pressure, thereby preventing liquid vaporizable material from flowing beyond the capillary feature 198. FIG. 61 shows an example of the heating element 100 having the capillary feature 198, consistent with implementations of the current subject matter. As shown in FIG. 61, the capillary feature 198 may form an end of the bridge 185 that extends outwardly away from the heating portion by a distance that is greater than a distance between the legs 106 and the heating portion 104. The end of the bridge 185 may be a sharp edge to further help prevent liquid vaporizable material from passing to the legs 106 and/or out of the heating portion 104, thereby reducing leaking and increasing the amount of vaporizable material that remains within the heating portion 104.

FIGS. 62-63 illustrate a variation of the heating element 100 shown in FIGS. 44-49. In this variation of the heating element 100, the legs 106 of the heating element 100 include a bend at an inflection region 111. The bend in the legs 106 may form a capillary feature 198, which helps to prevent liquid vaporizable material from flowing beyond the capillary feature 198. For example, the bend may create an abrupt change in capillary pressure, which may also help to limit or prevent liquid vaporizable material from flowing beyond the bend and/or from pooling between the legs 106 and the wick housing 98, and may help to limit or prevent liquid vaporizable material from flowing out of the heating portion 104.

FIGS. 64-65 illustrate a variation of the heating elements 100 shown in FIGS. 50A-55B. In this variation of the heating element 100, the legs 106 of the heating element 100 include a bend at an inflection region 111. The bend in the legs 106 may form a capillary feature 198, which helps to prevent liquid vaporizable material from flowing beyond the capillary feature 198. For example, the bend may create an abrupt change in capillary pressure, which also helps to limit or prevent liquid vaporizable material from flowing beyond the bend and/or from pooling between the legs 106 and the wick housing 98, and may help to limit or prevent liquid vaporizable material from flowing out of the heating portion 104.

Figure 68B:
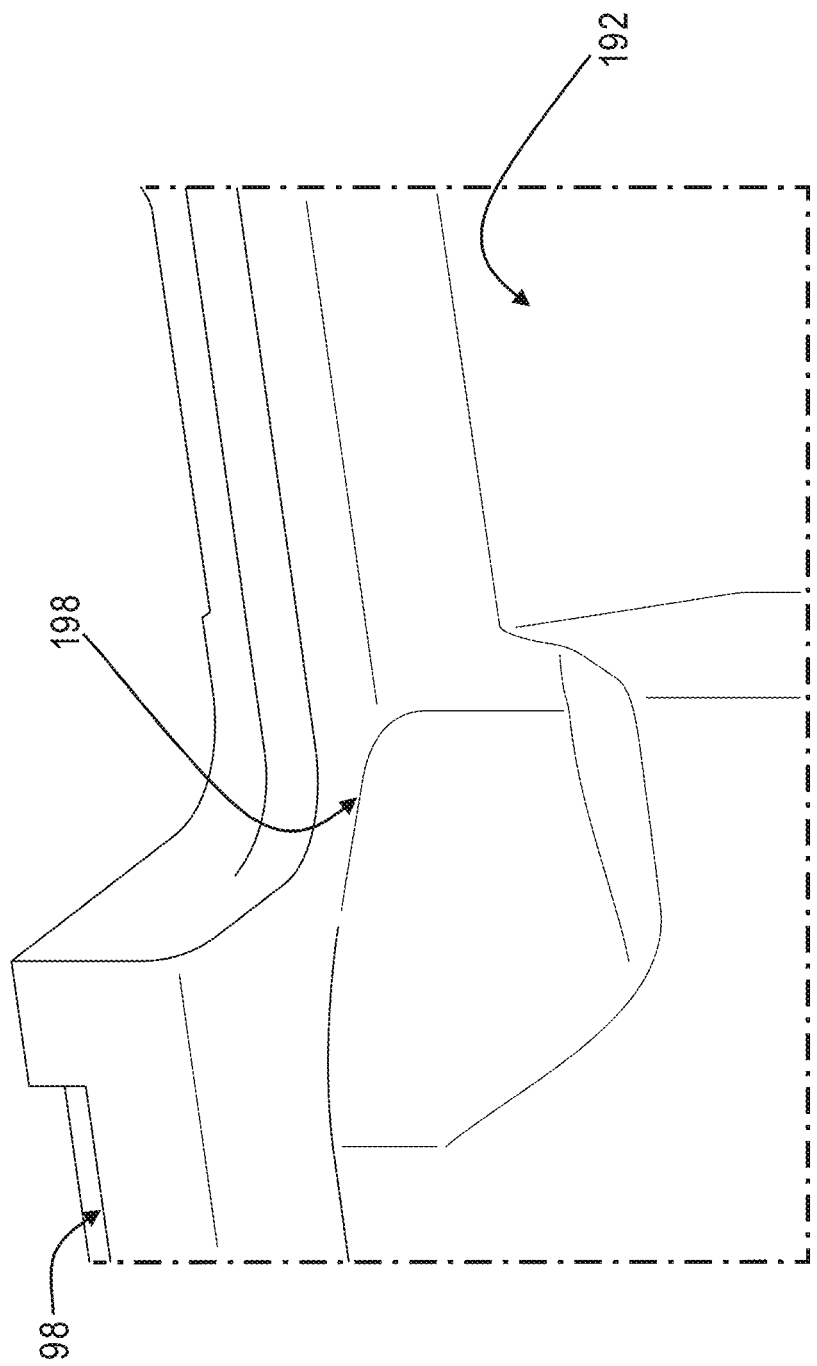
FIG. 68B shows a close-up view of a portion of a wick housing of an atomizer assembly consistent with implementations of the current subject matter.

FIGS. 68A-69 illustrate another example of the atomizer assembly 26, with the heating element 100 assembled with the wick housing 98 and the heat shield 118A, and FIG. 70 illustrates an exploded view of the atomizer assembly 26, consistent with implementations of the current subject matter. The wick housing 98 may be made of plastic, polypropylene, and the like. The wick housing 98 includes four recesses 192 in which at least a portion of each of the legs 106 of the heating element 100 may be positioned and secured. Within the recesses 192, the wick housing 98 may include one or more wick housing retention features 93 (see FIG. 72A) that help to secure the heating element 100 to the wick housing 98, such as, for example, via a snap-fit arrangement between at least a portion of the legs 106 of the heating element 100 and the wick housing retention features 93. The wick housing retention features 93 may also help to space the heating element 100 from a surface of the wick housing 98, to help prevent heat from acting on the wick housing and melting a portion of the wick housing 98.

As shown, the wick housing 98 also includes an opening 193 providing access to an internal volume 194, in which at least the heating portion 104 of the heating element 100 and the wicking element 70 are positioned.

The wick housing 98 may also include one or more other cutouts that help to space the heating element 100 from a surface of the wick housing 98 to reduce the amount of heat that contacts the surface of the wick housing 98. For example, the wick housing 98 may include cutouts 91. The cutouts 91 may be formed along an outer surface of the wick housing 98 proximate to the opening 193. The cutouts 91 may also include a capillary feature, such as the capillary feature 198. The capillary feature of the cutouts 91 may define a surface (e.g., curved surface 198) that breaks tangency points between adjacent (or intersecting) walls (such as the walls of the wick housing). The curved surface 198 may have a radius that is sufficient to reduce or eliminate the capillary formed between the adjacent outer walls of the wick housing.

Referring to FIGS. 68A-69, the wick housing 98 may include a tab 89. The tab 89 may help to properly position and/or orient the wick housing during assembly of the vaporizer cartridge, with respect to one or more other components of the vaporizer cartridge. For example, added material forming the tab 89 shifts the center of mass of the wick housing 98. Due to the shifted center of mass, the wick housing 98 may rotate or slide in a certain orientation to align with a corresponding feature of another component of the vaporizer cartridge during assembly.

Figure 71C:
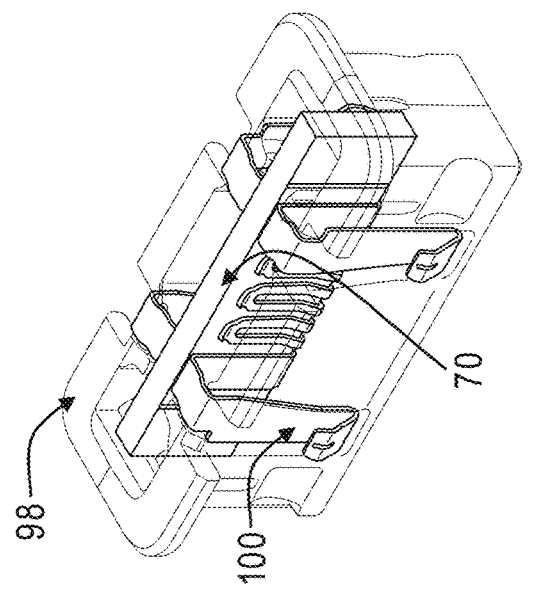
FIGS. 71A-71C show a process of assembling an atomizer consistent with implementations of the current subject matter.
Figure 71B:
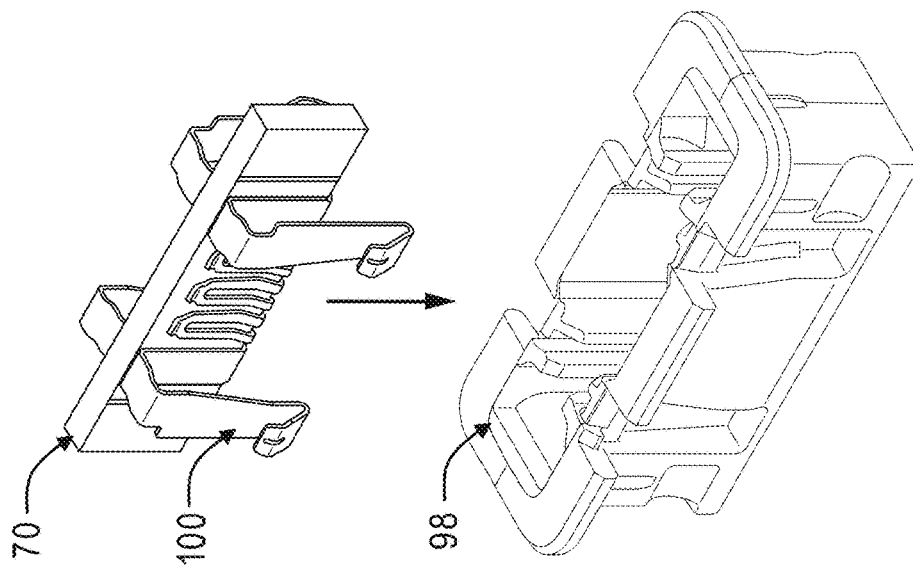
Figure 71A:
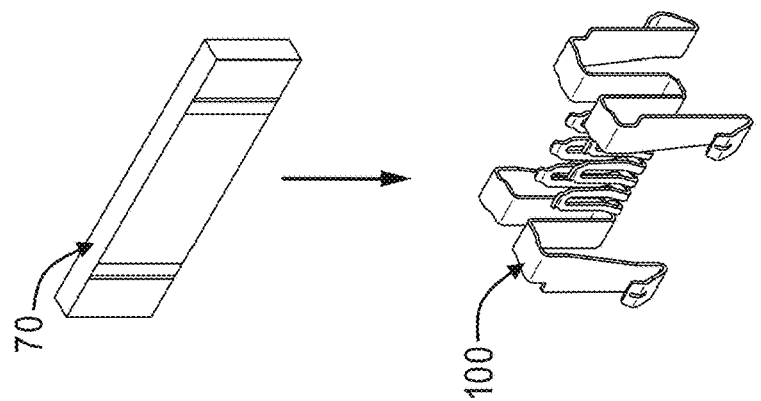

FIGS. 71A-71C illustrate an example method of forming the atomizer assembly 26 of the vaporizer cartridge 52, including the wick housing 98, the wicking element 70, and the heating element 100, consistent with implementations of the current subject matter. As shown in FIG. 71A, the wicking element 70 may be inserted into the pocket formed in the heating element 100 (e.g., formed by the side tine portions 126 and the platform tine portion 124. In some implementations, the wicking element 70 expands after being secured to the heating element 100, when vaporizable material is introduced to the wicking element 70.

FIG. 71B shows the wicking element 70 and the heating element 100 being coupled to the wick housing 98 and FIG. 71C shows an example of the wicking element 70 and the heating element 100 assembled with the wick housing 98. At least a portion of the heating element 100, such as the heating portion 104 may be positioned within the internal volume of the wick housing 98. The legs 106 (e.g., the retainer portions 99) of the heating element 100 may couple with the outer walls of the wick housing 98 via, for example, a snap-fit arrangement. In particular, the retainer portions 99 of the legs 106 may couple with and be positioned at least partially within the recesses in the wick housing 98.

Figure 72C:
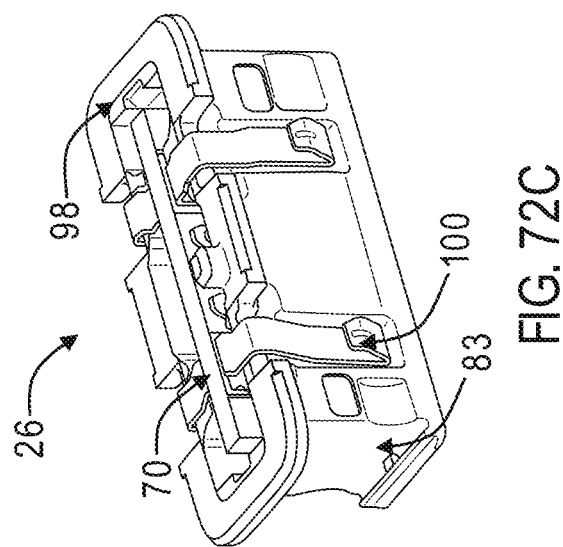
FIGS. 72A-72C show a process of assembling an atomizer consistent with implementations of the current subject matter.
Figure 72B:
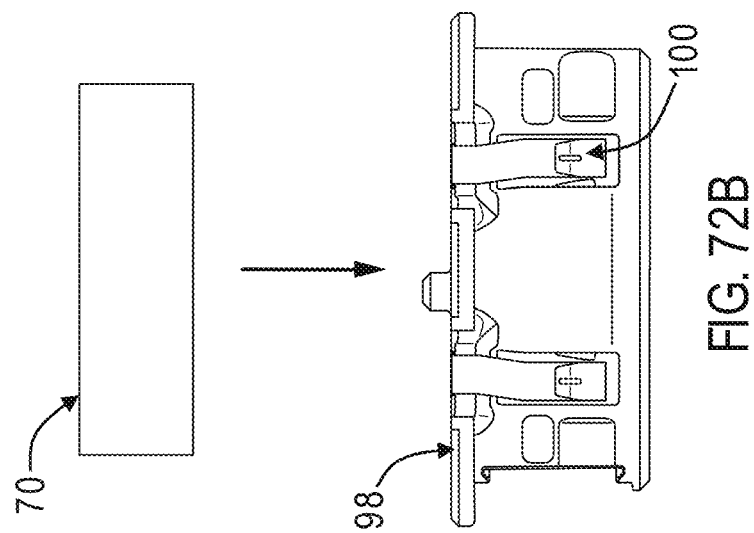
Figure 72A:
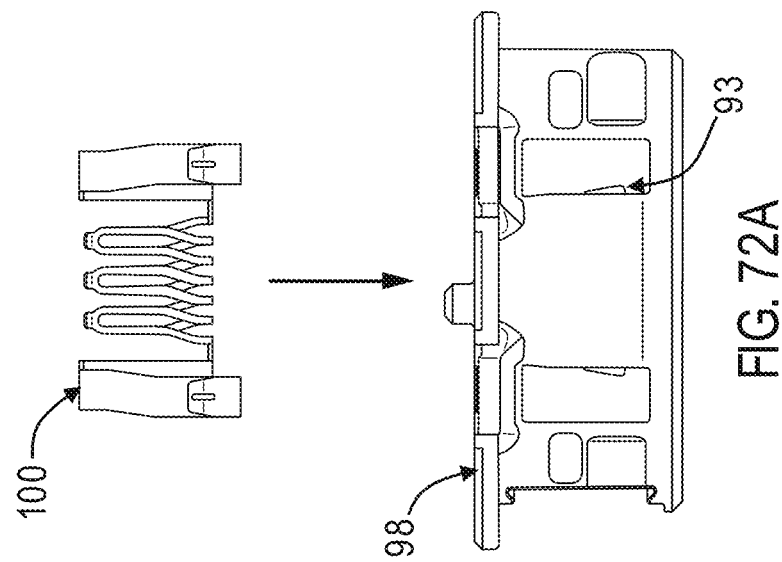

FIGS. 72A-72C illustrate another example method of forming the atomizer assembly 26 of the vaporizer cartridge 52, including the wick housing 98, the wicking element 70, and the heating element 100, consistent with implementations of the current subject matter. As shown in FIG. 72A, the heating element 100 may be coupled to the wick housing 98, for example, by inserting or otherwise positioning the at least a portion of the heating element 100, such as the heating portion 104 within the internal volume of the wick housing 98. The legs 106 (e.g., the retainer portions 99) of the heating element 100 may couple with the outer walls of the wick housing 98 via, for example, a snap-fit arrangement. In particular, the retainer portions 99 or another portion of the legs 106 may couple with and be positioned at least partially within the recesses in the wick housing 98, for example, by coupling with the wick housing retention features 93.

As shown in FIG. 72B, the wicking element 70 may be inserted into the pocket formed in the heating element 100 (e.g., formed by the side tine portions 126 and the platform tine portion 124. In some implementations, the wicking element 70 is compressed as the wicking element 70 is coupled with the heating element 70. In some implementations, the wicking element 70 fits within the heating element 70 and expands after being secured to the heating element 100, when vaporizable material is introduced to the wicking element 70.

FIG. 72C shows an example of the wicking element 70 and the heating element 100 assembled with the wick housing 98 to form the atomizer assembly 26.

Figure 73:
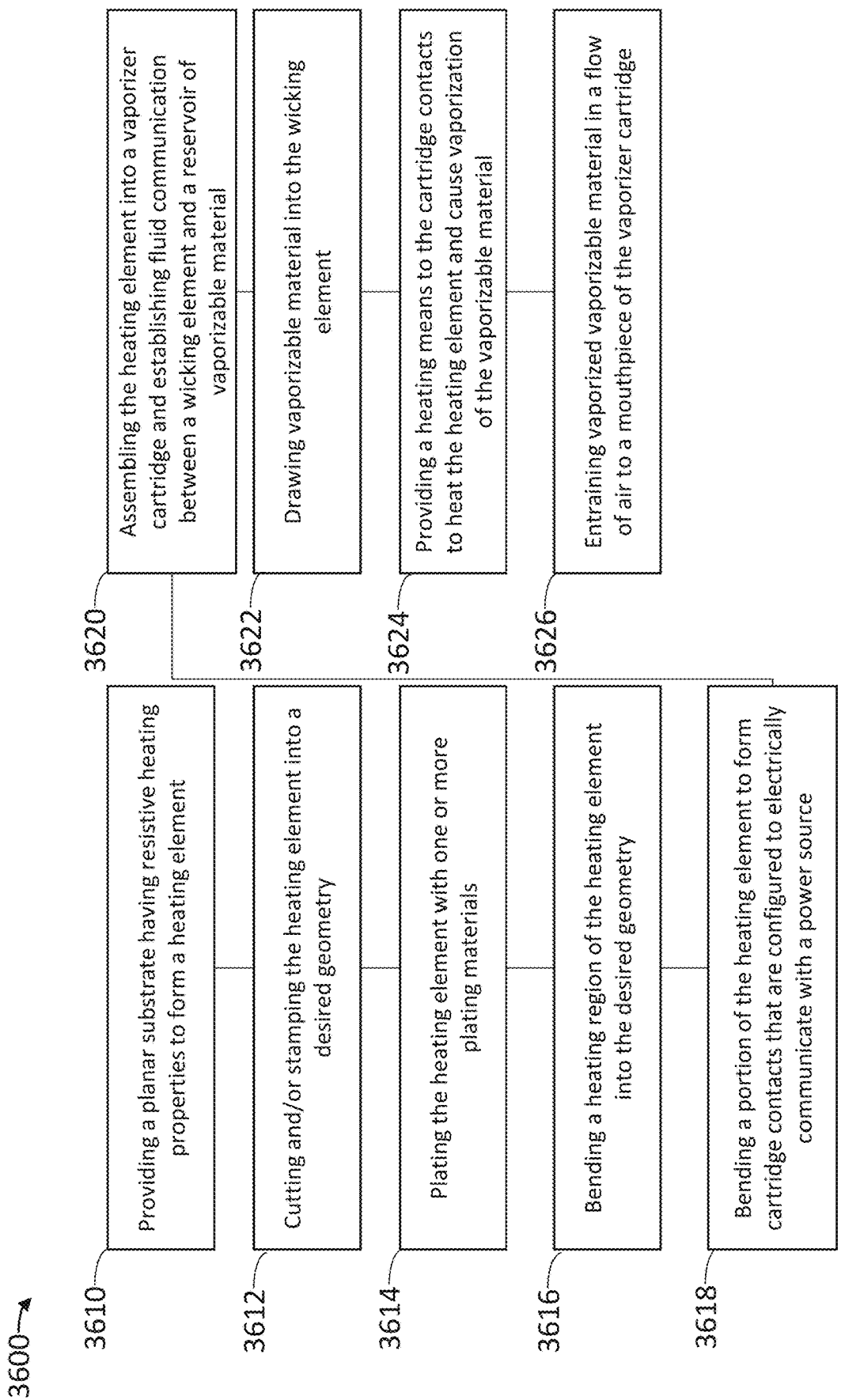
FIG. 73 shows a process flow chart illustrating features of a method of forming and implementing a heating element consistent with implementations of the current subject matter.

FIG. 73 illustrates an example process 3600 for assembling the heating element 100 consistent with implementations of the current subject matter. The process flow chart 3600 illustrates features of a method, which may optionally include some or all of the following. At block 3610, a planar substrate having resistive heating properties is provided. At block 3612, the planar substrate may be cut and/or stamped into the desired geometry. At block 3614, at least a portion of the heating element 100 may be plated. For example, as mentioned above, one or more layers of a plating material (e.g., an adhering plating material and/or an outer plating material) may be deposited onto at least a portion of an outer surface of the heating element 100. At block 3616, the heating portion 104 (e.g., the tines 102) may be bent and/or otherwise crimped about a wicking element to match the shape of the wicking element and to secure the wicking element to the heating element. At block 3618, the cartridge contacts 65, which in some implementations form an end portion of the legs 106 of the heating element 100, may be bent in a first or second direction along a plane or a third direction that is perpendicular to the first or second direction. At block 3620, the heating element 100 may be assembled into a vaporizer cartridge 52 and fluid communication between the wicking element 70 and a reservoir of vaporizable material may be caused. At 3622, the vaporizable material may be drawn into the wicking element 70, which may be positioned in contact with at least two surfaces of the heating portion 104 of the heating element 100. At block 3624, a heating means may be provided to the cartridge contacts 65 of the heating element to heat the heating element 100 at least the heating portion 104. The heating causes vaporization of the vaporizable material. At block 3626, the vaporized vaporizable material is entrained in a flow of air to a mouthpiece of the vaporization cartridge in which the heating element is positioned.

Terminology

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present.

Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments and implementations only and is not intended to be limiting. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

Spatially relative terms, such as "forward", "rearward", "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings provided herein.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the teachings herein. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the claims.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An atomizer assembly for a vaporizer cartridge, the vaporizer cartridge configured to be coupled to a vaporizer body of a vaporizer device, the atomizer assembly comprising:
    a wick housing comprising an opening, an outer rim surrounding and extending away from the opening, and an outer wall at least partially defining an internal volume configured to receive a wicking element and at least a heating portion of a heating element, the heating element also comprising a connecting portion configured to extend out of the internal volume and over the outer wall such that the outer wall is positioned between the heating portion and the connecting portion, the outer wall comprising two opposing short sides and two opposing long sides, each of the two opposing long sides having formed therein a recess configured to releasably couple the vaporizer cartridge to a corresponding feature of the vaporizer body;
    wherein the outer rim includes an aperture through which the connecting portion of the heating element is configured to pass through.

2. The atomizer assembly of claim 1, wherein the outer wall further comprises a base positioned approximately perpendicular to the two opposing short sides and the two opposing long sides, the base at least partially defining the internal volume.

3. The atomizer assembly of claim 2, wherein the base comprises one or more slots, wherein air pressure caused by a flow of vaporizable material within the heating portion is configured to escape through the one or more slots.

4. The atomizer assembly of claim 2, wherein the connecting portion includes a retainer portion configured to bend around the base to secure the heating element to the wick housing, and wherein the base includes an aperture configured to receive the retainer portion of the connecting portion.

5. The atomizer assembly of claim 2,
    wherein the connecting portion extends out of the opening and over the outer wall, and wherein the wicking element is configured to pass through the opening.

6. The atomizer assembly of claim 1, wherein an outer surface of the wick housing includes a recessed channel for securing the connecting portion of the heating element, the recess channel aligning with the aperture.

7. An atomizer assembly for a vaporizer cartridge, the vaporizer cartridge configured to be coupled to a vaporizer body of a vaporizer device, the atomizer assembly comprising:
    a wick housing comprising a base, an opening, an outer rim surrounding and extending away from the opening, and an outer wall at least partially defining an internal volume configured to receive a wicking element and at least a heating portion of a heating element, the heating element also comprising a connecting portion configured to extend out of the internal volume and over the outer wall such that the outer wall is positioned between the heating portion and the connecting portion, the outer wall comprising two opposing short sides and two opposing long sides, each of the two opposing long sides having formed therein a recess configured to releasably couple the vaporizer cartridge to a corresponding feature of the vaporizer body;

wherein the outer wall comprises a capillary feature, the capillary feature comprises a curved surface formed at an intersection between the outer rim and at least one of two opposing long sides of the base.

8. The atomizer assembly of claim 7, wherein the curved surface has a radius that is sufficient to break tangency points between an outer surface and the outer rim.

9. The atomizer assembly of claim 7, wherein the capillary feature is configured to cause an abrupt change in capillary pressure between the heating element and the wick housing to thereby prevent a vaporizable material from flowing beyond the capillary feature.

10. The atomizer assembly of claim 7, wherein the capillary feature is positioned within a cutout in the outer wall, the cutout configured to space the heating element from the outer wall, thereby preventing excess heat from contacting the outer wall.

11. The atomizer assembly of claim 1, wherein at least one of the two opposing short sides comprises a chip recess configured to receive an identification chip.

12. The atomizer assembly of claim 11, wherein the chip recess comprises at least two walls configured to surround and retain the identification chip.

13. The atomizer assembly of claim 1, wherein the recess is positioned proximate to an intersection between a long side of the two opposing long sides and a short side of the two opposing short sides.

14. The atomizer assembly of claim 1, wherein each of the two opposing long sides includes two recesses.

15. A method of forming an atomizer assembly for a vaporizer device, the method comprising:

coupling a heating element to a wick housing configured to surround a heating portion of the heating element, the wick housing comprising:

an outer wall comprising two opposing short sides and two opposing long sides, the two opposing long sides having formed therein a recessed channel configured to receive a connecting portion of the heating element, a base positioned approximately perpendicular to the two opposing short sides and the two opposing long sides, an internal volume formed by the outer wall and the base, the internal volume surrounding the heating portion of the heating element, and an opening opposite the base, and an outer rim surrounding and extending away from the opening, wherein the outer rim includes an aperture through which the connecting portion of the heating element passes though.

16. The method of claim 15, wherein the coupling includes sliding the connecting portion of the heating element in the recessed channel formed in the outer wall of the wick housing.

17. An atomizer assembly for a vaporizer cartridge, the atomizer assembly comprising:

a wick housing comprising an opening, an outer rim surrounding and extending away from the opening, and an outer wall at least partially defining an internal volume configured to receive a wicking element and at least a heating portion of a heating element, the heating element also comprising a connecting portion configured to extend out of the internal volume and over the outer wall such that the outer wall is positioned between the heating portion and the connecting portion, the outer wall comprising two opposing short sides and two opposing long sides;

wherein the outer rim includes an aperture through which the connecting portion of the heating element is configured to pass through.

18. The atomizer assembly of claim 17, wherein each of the two opposing long sides having formed therein a recess configured to releasably couple the vaporizer cartridge to a corresponding feature of a vaporizer body.

* * * * *